(12) United States Patent
Chandrasekaran et al.

(10) Patent No.: US 12,077,807 B2
(45) Date of Patent: Sep. 3, 2024

(54) COMPOSITIONS AND METHODS FOR ANALYTE DETECTION USING NANOSWITCHES

(71) Applicants: The Research Foundation for The State University of New York, Albany, NY (US); Children's Medical Center Corporation, Boston, MA (US)

(72) Inventors: Arun Richard Chandrasekaran, Albany, NY (US); Clinton H. Hansen, Cambridge, MA (US); Mounir Ahmad Koussa, Somerville, MA (US); Kenneth Anders Halvorsen, Glenmont, NY (US); Wesley Philip Wong, Cambridge, MA (US)

(73) Assignees: The Research Foundation for The State University of New York, Albany, NY (US); Children's Medical Center Corporation, Boston, MA (US)

( * ) Notice: Subject to any disclaimer, the term of this patent is extended or adjusted under 35 U.S.C. 154(b) by 51 days.

(21) Appl. No.: 15/738,982

(22) PCT Filed: Jun. 27, 2016

(86) PCT No.: PCT/US2016/039654
§ 371 (c)(1),
(2) Date: Dec. 21, 2017

(87) PCT Pub. No.: WO2017/003950
PCT Pub. Date: Jan. 5, 2017

(65) Prior Publication Data
US 2018/0223344 A1 Aug. 9, 2018

Related U.S. Application Data

(60) Provisional application No. 62/185,582, filed on Jun. 27, 2015.

(51) Int. Cl.
| | |
|---|---|
| *C12Q 1/6816* | (2018.01) |
| *C12Q 1/6818* | (2018.01) |
| *C12Q 1/6839* | (2018.01) |
| *G01N 27/447* | (2006.01) |
| *G01N 30/86* | (2006.01) |
| *G01N 30/02* | (2006.01) |

(52) U.S. Cl.
CPC ......... *C12Q 1/6816* (2013.01); *C12Q 1/6818* (2013.01); *C12Q 1/6839* (2013.01); *G01N 27/447* (2013.01); *G01N 30/8675* (2013.01); *G01N 2030/027* (2013.01)

(58) Field of Classification Search
None
See application file for complete search history.

(56) References Cited

U.S. PATENT DOCUMENTS

| | | | |
|---|---|---|---|
| 4,599,303 A | * | 7/1986 | Yabusaki ............. C12Q 1/6816 435/6.12 |
| 5,571,677 A | | 11/1996 | Gryaznov |
| 5,635,352 A | | 6/1997 | Urdea et al. |
| 5,888,731 A | | 5/1999 | Yager et al. |
| 5,902,724 A | | 5/1999 | Lane et al. |
| 6,143,504 A | | 11/2000 | Das et al. |
| 6,232,066 B1 | * | 5/2001 | Felder .................... C40B 30/04 435/6.11 |
| 6,251,660 B1 | | 6/2001 | Muir et al. |
| 6,569,306 B1 | | 5/2003 | Read et al. |
| 6,770,698 B1 | | 8/2004 | Chu et al. |
| 8,129,119 B2 | | 3/2012 | Jarrell et al. |
| 8,491,454 B2 | | 7/2013 | Wong et al. |
| 8,795,143 B2 | | 8/2014 | Wong et al. |
| 9,255,905 B1 | | 2/2016 | Mellors et al. |
| 9,914,958 B2 | | 3/2018 | Wong et al. |
| 9,994,839 B2 | | 6/2018 | Lo et al. |
| 10,919,037 B2 | | 2/2021 | Wong et al. |
| 10,948,401 B2 | | 3/2021 | Yang et al. |
| 11,198,900 B2 | | 12/2021 | Koussa et al. |
| 11,396,650 B2 | | 7/2022 | Wong et al. |
| 11,591,636 B2 | | 2/2023 | Wong et al. |
| 2002/0081744 A1 | | 6/2002 | Chan et al. |
| 2002/0177144 A1 | | 11/2002 | Remacle et al. |

(Continued)

FOREIGN PATENT DOCUMENTS

| | | |
|---|---|---|
| JP | H06-508753 A | 10/1994 |
| JP | 2000-312589 A | 8/2000 |

(Continued)

OTHER PUBLICATIONS

Koussa et al., "Protocol for sortase-mediated construction of DNA-protein hybrids and functional nanostructures", Methods, vol. 67, Feb. 22, 2014, pp. 134-141. (Year: 2014).*
U.S. Appl. No. 15/888,941, filed Feb. 5, 2018, Published, 2018-0291434.
U.S. Appl. No. 16/087,500, filed Sep. 21, 2018, Published, 2019-0070604.
U.S. Appl. No. 16/088,006, filed Sep. 24, 2018, Pending.
PCT/US2018/062141, Nov. 20, 2018, Published, WO 2019/100080.
Invitation to Pay Additional Fees for Application No. PCT/US2016/039654 mailed Aug. 30, 2016.
International Search Report and Written Opinion for Application No. PCT/US2016/039654 mailed Feb. 7, 2017.

(Continued)

*Primary Examiner* — Bradley L. Sisson
(74) *Attorney, Agent, or Firm* — Wolf, Greenfield & Sacks, P.C.

(57) ABSTRACT

Provided herein are nucleic acid-based nanoswitches that can detect specific nucleic acids and other analytes types by for example a simple gel electrophoresis readout. Binding of the target to the nanoswitches induces a conformation change from a linear, open conformation to a looped, closed conformation. These nanoswitches may be used in diagnostic assays such as nucleic acid-based diagnostic assays, to detect, measure and/or purify a variety of targets including low abundance targets.

9 Claims, 36 Drawing Sheets

Specification includes a Sequence Listing.

(56) References Cited

U.S. PATENT DOCUMENTS

| | | |
|---|---|---|
| 2002/0182717 A1 | 12/2002 | Karlsson et al. |
| 2003/0143549 A1 | 7/2003 | Yang et al. |
| 2003/0186301 A1* | 10/2003 | Christian et al. ............................ C12Q 2525/143 435/6.11 |
| 2006/0194240 A1 | 8/2006 | Arnold et al. |
| 2006/0257958 A1* | 11/2006 | Bruno ..................... B82Y 5/00 435/7.93 |
| 2007/0026423 A1 | 2/2007 | Koehler et al. |
| 2007/0037152 A1 | 2/2007 | Drmanac |
| 2007/0117109 A1 | 5/2007 | Rothemund |
| 2007/0154899 A1 | 7/2007 | Coull et al. |
| 2007/0155017 A1 | 7/2007 | Wyatt |
| 2008/0038725 A1 | 2/2008 | Luo et al. |
| 2008/0131870 A1 | 6/2008 | Allawi et al. |
| 2008/0312103 A1 | 12/2008 | Nemoto et al. |
| 2009/0087838 A1 | 4/2009 | Reif et al. |
| 2009/0286694 A1 | 11/2009 | Zainiev et al. |
| 2010/0015608 A1 | 1/2010 | Kolpashchikov |
| 2010/0035247 A1 | 2/2010 | Burton |
| 2010/0137120 A1 | 6/2010 | Wong et al. |
| 2010/0206730 A1 | 8/2010 | Hunkapiller et al. |
| 2010/0216658 A1 | 8/2010 | Chaput et al. |
| 2011/0086774 A1 | 4/2011 | Dunaway |
| 2011/0268654 A1 | 11/2011 | Hilderbrand et al. |
| 2012/0058008 A1 | 3/2012 | Corbett et al. |
| 2013/0004523 A1 | 1/2013 | Zubarev et al. |
| 2013/0130884 A1 | 5/2013 | Wong et al. |
| 2013/0196341 A1 | 8/2013 | Neely et al. |
| 2013/0225429 A1 | 8/2013 | Curry |
| 2013/0310260 A1 | 11/2013 | Kim et al. |
| 2013/0344508 A1 | 12/2013 | Schwartz et al. |
| 2014/0255939 A1* | 9/2014 | Wong et al. ......... C12Q 1/6804 435/6.11 |
| 2014/0284213 A1 | 9/2014 | Sabin et al. |
| 2014/0302532 A1 | 10/2014 | Wilson et al. |
| 2015/0027894 A1 | 1/2015 | Puleo et al. |
| 2015/0093836 A1 | 4/2015 | Suzuki et al. |
| 2015/0099650 A1 | 4/2015 | Sood et al. |
| 2015/0292007 A1 | 10/2015 | Church et al. |
| 2015/0361422 A1 | 12/2015 | Sampson et al. |
| 2016/0186238 A1 | 6/2016 | Liu et al. |
| 2017/0369935 A1 | 12/2017 | Koussa et al. |
| 2018/0135043 A1 | 5/2018 | Wong et al. |
| 2018/0291434 A1 | 10/2018 | Wong et al. |
| 2019/0048409 A1 | 2/2019 | Wong et al. |
| 2019/0064056 A1 | 2/2019 | Yang et al. |
| 2019/0070604 A1 | 3/2019 | Wong et al. |
| 2020/0116712 A1 | 4/2020 | Hansen et al. |
| 2020/0340033 A1 | 10/2020 | Wong et al. |
| 2021/0239602 A1 | 8/2021 | Yang et al. |
| 2023/0045556 A1 | 2/2023 | Wong et al. |
| 2023/0146476 A1 | 5/2023 | MacDonald et al. |

FOREIGN PATENT DOCUMENTS

| | | |
|---|---|---|
| JP | 2003-219897 A | 8/2003 |
| JP | 2005-536234 A | 12/2005 |
| JP | 2008-259453 A | 10/2008 |
| JP | 2009-521230 | 6/2009 |
| WO | WO 93/01313 A1 | 1/1993 |
| WO | WO 98/18961 A1 | 5/1998 |
| WO | WO 00/40751 A2 | 7/2000 |
| WO | WO 2004/016767 A2 | 2/2004 |
| WO | WO 2007/076128 A2 | 7/2007 |
| WO | WO 2011/005221 A1 | 1/2011 |
| WO | WO 2011/153211 A1 | 12/2011 |
| WO | WO 2012/058638 A2 | 5/2012 |
| WO | WO 2013/010023 A2 | 1/2013 |
| WO | WO 2013/067489 A1 | 5/2013 |
| WO | WO 2014/011800 A1 | 1/2014 |
| WO | WO 2015/006626 A1 | 1/2015 |
| WO | WO 2015/040009 A1 | 3/2015 |
| WO | WO 2015/164602 A2 | 10/2015 |
| WO | WO 2016/089588 A1 | 6/2016 |
| WO | WO 2016/164866 A1 | 10/2016 |
| WO | WO 2016/196824 A1 | 12/2016 |
| WO | WO 2017/003950 A2 | 1/2017 |
| WO | WO 2017/139409 A1 | 8/2017 |
| WO | WO 2017/147398 A1 | 8/2017 |
| WO | WO 2018/106721 A1 | 6/2018 |
| WO | WO 2019/100080 A1 | 5/2019 |

OTHER PUBLICATIONS

International Preliminary Report on Patentability mailed Jan. 11, 2018 for Application No. PCT/US2016/039654.

[No Author Listed], Wikipedia Entry, "Xhol." May 14, 2014. Retrieved from the internet. <https://en.wikipedia.org/w/index/php?title=Xhol&oldid=608536958>. Retrieved on Oct. 18, 2016.

Aaij et al., The gel electrophoresis of DNA. Biochim Biophys Acta. May 10, 1972;269(2):192-200.

Baumann et al., Ionic effects on the elasticity of single DNA molecules. Proc Natl Acad Sci U S A. Jun. 10, 1997;94(12):6185-90.

Bellot et al., Recovery of intact DNA nanostructures after agarose gel-based separation. Nat Methods. Mar. 2011;8(3):192-4. doi: 10.1038/nmeth0311-192.

Bishop et al., Electrophoretic separation of viral nucleic acids on polyacrylamide gels. J Mol Biol. Jun. 28, 1967;26(3):373-87.

Bustamante et al., Entropic elasticity of lambda-phage DNA. Science. Sep. 9, 1994;265(5178):1599-600.

Bustamante et al., Ten years of tension: single-molecule DNA mechanics. Nature. Jan. 23, 2003;421(6921):423-7.

Chandrasekaran et al., Label-free Detection of Specific Nucleic Acid Sequences using DNA Nanoswitches. The RNA Institute, University at Albany, State University of New York.

Chandrasekaran et al., Programmable DNA Nanoswitches for Detection of Nucleic Acid Sequences. ACS Sens., 2016, 1 (2), pp. 120-123.

Cheng et al., Early pregnancy factor in cervical mucus of pregnant women. Am J Reprod Immunol. Feb. 2004;51(2):102-5.

Chilkoti et al., Molecular Origins of the Slow Streptavidin-Biotin Dissociation Kinetics. J Am Chem Soc. 1995;117(43):10622-8.

Chivers et al., A streptavidin variant with slower biotin dissociation and increased mechanostability. Nat Methods. May 2010;7(5):391-3. doi: 10.1038/nmeth.1450. Epub Apr. 11, 2010.

Cho et al., A genomic-scale view of the cAMP response element-enhancer decoy: a tumor target-based genetic tool. Proc Natl Acad Sci U S A. Nov. 26, 2002;99(24):15626-31. Epub Nov. 18, 2002.

Conde et al., Implantable hydrogel embedded dark-gold nanoswitch as a theranostic probe to sense and overcome cancer multidrug resistance. Proc Natl Acad Sci U S A. Mar. 17, 2015;112(11):E1278-87. doi: 10.1073/pnas.1421229112. Epub Mar. 2, 2015.

Deniz et al., Single-molecule biophysics: at the interface of biology, physics and chemistry. J R Soc Interface. Jan. 6, 2008;5(18):15-45.

Doshi et al., In vitro nanobody discovery for integral membrane protein targets. Sci Rep. Oct. 24, 2014;4:6760. doi: 10.1038/srep06760.

Douglas et al., A logic-gated nanorobot for targeted transport of molecular payloads. Science. Feb. 17, 2012;335(6070):831-4. doi: 10.1126/science.1214081.

Douglas et al., Self-assembly of DNA into nanoscale three-dimensional shapes. Nature. May 21, 2009;459(7245):414-8. doi: 10.1038/nature08016.

Evans et al., Dynamic strength of molecular adhesion bonds. Biophys J. Apr. 1997;72(4):1541-55.

Evans et al., Forces and bond dynamics in cell adhesion. Science. May 25, 2007;316(5828):1148-53.

Evans, Probing the relation between force—lifetime—and chemistry in single molecular bonds. Annu Rev Biophys Biomol Struct. 2001;30:105-28.

Fazio et al., DNA curtains and nanoscale curtain rods: high-throughput tools for single molecule imaging. Langmuir. Sep. 16, 2008;24(18):10524-31. doi: 10.1021/la801762h. Epub Aug. 7, 2008.

França et al., A review of DNA sequencing techniques. Q Rev Biophys. May 2002;35(2):169-200.

Green, Avidin and streptavidin. Methods Enzymol. 1990;184:51-67.

(56) References Cited

OTHER PUBLICATIONS

Greenleaf et al., High-resolution, single-molecule measurements of biomolecular motion. Annu Rev Biophys Biomol Struct. 2007;36:171-90.
Halvorsen et al., Binary DNA nanostructures for data encryption. PLoS One. 2012;7(9):e44212. doi: 10.1371/journal.pone.0044212. Epub Sep. 11, 2012.
Halvorsen et al., Cross-platform comparison of nucleic acid hybridization: toward quantitative reference standards. Anal Biochem. Nov. 15, 2014;465:127-33. doi: 10.1016/j.ab.2014.08.001. Epub Aug. 12, 2014.
Halvorsen et al., Massively Parallel Single-Molecule Manipulation Using Centrifugal Force. Biophys J. Jun. 2, 2010;98(11):L53-5.
Halvorsen et al., Nanoengineering a single-molecule mechanical switch using DNA self-assembly. Nanotechnology. Dec. 9, 2011;22(49):494005. doi:10.1088/0957-4484/22/49/494005. Epub Nov. 21, 2011.
Halvorsen, Probing Weak Single-Molecule Interactions: Development and Demonstration of a New Instrument. Boston University, College of Engineering dissertation. 2007: 102 pages.
Hanke et al., Entropy loss in long-distance DNA looping. Biophys J. Jul. 2003;85(1):167-73.
Hansen et al., Nanoswitch-linked immunosorbent assay (NLISA) for fast, sensitive, and specific protein detection. PNAS. Sep. 26, 2017;114(39):10367-10372. Supporting Information, 4 pages.
Hassur et al., UV shadowing—a new and convenient method for the location of ultraviolet-absorbing species in polyacrylamide gels. Anal Biochem. May 1974;59(1):162-4.
Hellman et al., Electrophoretic mobility shift assay (EMSA) for detecting protein-nucleic acid interactions. Nat Protoc. 2007;2(8):1849-61.
Idili et al., Programmable pH-triggered DNA nanoswitches. J Am Chem Soc. Apr. 23, 2014;136(16):5836-9. doi: 10.1021/ja500619w. Epub Apr. 9, 2014. Abstract only.
Jones et al., Nanomaterials. Programmable materials and the nature of the DNA bond. Science. Feb. 20, 2015;347(6224):1260901. doi: 10.1126/science.1260901.
Jung et al., Binding and Dissociation Kinetics of Wild-Type and Mutant Streptavidins on Mixed Biotin-Containing Alkylthiolate Monolayers. Langmuir. Nov. 28, 2000;16(24): 9421-32.
Khalil et al., Single M13 bacteriophage tethering and stretching. Proc Natl Acad Sci U S A. Mar. 20, 2007;104(12):4892-7. Epub Mar. 13, 2007.
Kim et al., A mechanically stabilized receptor-ligand flex-bond important in the vasculature. Nature. Aug. 19, 2010;466(7309):992-5. doi: 10.1038/nature09295.
Kim et al., Multiplexed single-molecule assay for enzymatic activity on flow-stretched DNA. Nat Methods. May 2007;4(5):397-9. Epub Apr. 15, 2007.
Klumb et al., Energetic roles of hydrogen bonds at the ureido oxygen binding pocket in the streptavidin-biotin complex. Biochemistry. May 26, 1998;37(21):7657-63.
Koch et al., Prospects and limitations of the rosette inhibition test to detect activity of early pregnancy factor in the pig. J Reprod Fertil. May 1985;74(1):29-38.
Koussa et al., DNA nanoswitches: a quantitative platform for gel-based biomolecular interaction analysis. Nat Methods. Feb. 2015;12(2):123-6. doi: 10.1038/nmeth.3209. Epub Dec. 8, 2014.
Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.
Kufer et al., Single-molecule cut-and-paste surface assembly. Science. Feb. 1, 2008;319(5863):594-6. doi:10.1126/science.1151424.
Leier et al., Cryptography with DNA binary strands. Biosystems. Jun. 2000;57(1):13-22.
Mcdonell et al., Analysis of restriction fragments of T7 Dna and determination of molecular weights by electrophoresis in neutral and alkaline gels. J Mol Biol. Feb. 15, 1977;110(1):119-46.
Modi et al., A DNA nanomachine that maps spatial and temporal pH changes inside living cells. Nat Nanotechnol. May 2009;4(5):325-30. doi: 10.1038/nnano.2009.83. Epub Apr. 6, 2009. Abstract only.
Morton et al., Rosette inhibition test: A multicentre investigation of early pregnancy factor in humans. J Reprod Immunol. Sep. 1982;4(5):251-61.
Morton et al., Early pregnancy factor. Semin Reprod Endocrinol. May 1992;10:72-82.
Nelson et al., Tethered particle motion as a diagnostic of DNA tether length. J Phys Chem B. Aug. 31, 2006;110(34):17260-7. Abstract only.
Neuman et al., Single-molecule force spectroscopy: optical tweezers, magnetic tweezers and atomic force microscopy. Nat Methods. Jun. 2008;5(6):491-505. doi: 10.1038/nmeth.1218.
Park et al., Dual blockade of cyclic AMP response element-(CRE) and AP-1-directed transcription by CRE-transcription factor decoy oligonucleotide. gene-specific inhibition of tumor growth. J Biol Chem. Jan. 15, 1999;274(3):1573-80.
Pei et al, A DNA nanostructure-based biomolecular probe carrier platform for electrochemical biosensing. Adv Mater. Nov. 9, 2010;22(42):4754-8. doi: 10.1002/adma.201002767.
Quek et al., Mechanically controlled binary conductance switching of a single-molecule junction. Nat Nanotechnol. Apr. 2009;4(4):230-4. doi: 10.1038/nnano.2009.10. Epub Mar. 1, 2009.
Rief et al., Sequence-dependent mechanics of single DNA molecules. Nat Struct Biol. Apr. 1999;6(4):346-9.
Ritort, Single-molecule experiments in biological physics: methods and applications. J Phys Condens Matter. Aug. 16, 2006;18(32):R531-83. doi:10.1088/0953-8984/18/32/R01. Epub Jul. 25, 2006.
Rothemund, Folding DNA to create nanoscale shapes and patterns. Nature. Mar. 16, 2006;440(7082):297-302.
Sacca et al., DNA origami: the art of folding DNA. Angew Chem Int Ed Engl. Jan. 2, 2012;51(1):58-66. doi: 10.1002/anie. 201105846. Epub Dec. 7, 2011.
Seeman, DNA in a material world. Nature. Jan. 23, 2003;421(6921):427-31.
Seeman, Nanomaterials based on DNA. Annu Rev Biochem. 2010;79:65-87. doi: 10.1146/annurev-biochem-060308-102244.
Shroff et al., Biocompatible force sensor with optical readout and dimensions of 6 nm3. Nano Lett. Jul. 2005;5(7):1509-14.
Shroff et al., Optical measurement of mechanical forces inside short DNA loops. Biophys J. Mar. 15, 2008;94(6):2179-86. Epub Dec. 7, 2007.
Smith et al., Overstretching B-DNA: the elastic response of individual double-stranded and single-stranded DNA molecules. Science. Feb. 9, 1996;271(5250):795-9.
Strunz et al., Dynamic force spectroscopy of single DNA molecules. Proc Natl Acad Sci U S A. Sep. 28, 1999;96(20):11277-82.
Svoboda et al., Direct observation of kinesin stepping by optical trapping interferometry. Nature. Oct. 21, 1993;365(6448):721-7.
Thorne, Electrophoretic separation of polyoma virus DNA from host cell DNA. Virology. Jun. 1966;29(2):234-9.
Thuring et al., A freeze-squeeze method for recovering long DNA from agarose gels. Anal Biochem. May 26, 1975;66(1):213-20.
Wiita et al., Force-dependent chemical kinetics of disulfide bond reduction observed with single-molecule techniques. Proc Natl Acad Sci U S A. May 9, 2006;103(19):7222-7. Epub Apr. 27, 2006.
Williams et al., Entropy and heat capacity of DNA melting from temperature dependence of single molecule stretching. Biophys J. Apr. 2001;80(4):1932-9.
Winfree et al., Design and self-assembly of two-dimensional DNA crystals. Nature. Aug. 6, 1998;394(6693):539-44.
Wong et al., The effect of integration time on fluctuation measurements: calibrating an optical trap in the presence of motion blur. Opt Express. Dec. 11, 2006;14(25):12517-31.
Zadeh et al., Nupack: Analysis and design of nucleic acid systems. J Comput Chem. Jan. 15, 2011;32(1):170-3. doi: 10.1002/jcc.21596.
Zhang et al., Mechanoenzymatic cleavage of the ultralarge vascular protein, von Willebrand Factor. Science. Jun. 5, 2009;324(5932):1330-4.
Zheng et al., From molecular to macroscopic via the rational design of a self-assembled 3D DNA crystal. Nature. Sep. 3, 2009;461(7260):74-7. doi: 10.1038/nature08274.

(56) References Cited

OTHER PUBLICATIONS

Butko et al., Detection of Ligand-Induced Conformational Changes in Oligonucleotides by Second-Harmonic Generation at a Supported Lipid Bilayer Interface. Anal Chem. Nov. 1, 2016;88(21):10482-10489. Epub Oct. 12, 2016. Accepted Manuscript, 23 pages.
Devaraj et al., Biomedical applications of tetrazine cycloadditions. Acc Chem Res. Sep. 20, 2011;44(9):816-27. doi: 10.1021/ar200037t. Epub May 31, 2011.
Kleiner et al., Small-molecule discovery from DNA-encoded chemical libraries. Chem Soc Rev. Dec. 2011;40(12):5707-17. doi: 10.1039/c1cs15076f. Epub Jun. 14, 2011.
Su et al., Nucleic acid fluorescent probes for biological sensing. Appl Spectrosc. Nov. 2012;66(11):1249-62. doi: 10.1366/12-06803. Review.
Yang et al., Multiplexed single-molecule force spectroscopy using a centrifuge. Nat Commun. Mar. 17, 2016;7:11026(1-7). doi:10.1038/ncomms11026. PubMed PMID: 26984516; PubMed Central PMCID: PMC4800429.
U.S. Appl. No. 15/888,941, filed Feb. 5, 2018, Pending.
U.S. Appl. No. 15/578,962, filed Dec. 1, 2017, Published, 2018-0135043.
U.S. Appl. No. 15/533,473, filed Jun. 6, 2017, Published, 2017-0369935.
U.S. Appl. No. 16/074,952, filed Aug. 2, 2018, Pending.
PCT/US2016/039654, Aug. 30, 2016, Invitation to Pay Additional Fees.
PCT/US2016/039654, Feb. 7, 2017, International Search Report and Written Opinion.
PCT/US2016/039654, Jan. 11, 2018, International Preliminary Report on Patentability.
U.S. Appl. No. 16/765,375, filed May 19, 2020, Pending.
Hopwood et al., Integrated microfluidic system for rapid forensic DNA analysis: sample collection to DNA profile. Anal Chem. Aug. 15, 2010;82(16):6991-9. doi: 10.1021/ac101355r.
Yang et al., An integratable microfluidic cartridge for forensic swab samples lysis. Forensic Sci Int Genet. Jan. 2014;8(1):147-58. doi: 10.1016/j.fsigen.2013.08.012. Epub Sep. 8, 2013.
Fang et al., Tuning surface states to achieve the modulated fluorescence of carbon dots for probing the activity of alkaline phosphatase and immunoassay of alpha-fetoprotein. Sensors and Actuators B: Chemical. 2018;257:620-628.
Lubken et al., Multiplexed Continuous Biosensing by Single-Molecule Encoded Nanoswitches. Nano Lett. Apr. 8, 2020;20(4):2296-2302. doi: 10.1021/acs.nanolett.9b04561. Epub Mar. 12, 2020.
Papadakis et al., Acoustic characterization of nanoswitch structures: application to the DNA Holliday Junction. Nano Lett. Dec. 8, 2010;10(12):5093-7. doi: 10.1021/nl103491v. Epub Nov. 1, 2010.
Ping, High Performing assay using antibody-conjugated DNA nanoswitches detects proteins. MRS Bulletin. 2017;42:780. 1 page.
Porchetta et al., Programmable Nucleic Acid Nanoswitches for the Rapid, Single-Step Detection of Antibodies in Bodily Fluids. J Am Chem Soc. Jan. 24, 2018;140(3):947-953. doi: 10.1021/jacs.7b09347. Epub Jan. 9, 2018.
U.S. Appl. No. 15/578,962, filed Dec. 1, 2017, Allowed, 2018-0135043.
U.S. Appl. No. 17/845,914, filed Jun. 21, 2022, Pending.
U.S. Appl. No. 16/074,952, filed Aug. 2, 2018, Published, 2019-0048409.
U.S. Appl. No. 16/765,375, filed May 19, 2020, Published, 2020-0340033.
Ando et al., Single-nanoparticle tracking with angstrom localization precision and microsecond time resolution. Biophys J. Dec. 18, 2018;115(12):2413-2427. Epub Nov. 17, 2018.
Baslé et al., Protein chemical modification on endogenous amino acids. Chem Biol. Mar. 26, 2010;17(3):213-27.
Cheezum et al., Quantitative comparison of algorithms for tracking single fluorescent particles. Biophys J. Oct. 2001;81(4):2378-88.
Fu et al., Flow-induced elongation of von Willebrand factor precedes tension-dependent activation. Nat Commun. Aug. 23, 2017;8(1):324.
Horn et al., Forks and combs and DNA: the synthesis of branched oligodeoxyribonucleotides. Nucleic Acids Res. Sep. 12, 1989;17(17):6959-67.
Jiang et al., Electrostatic steering enables flow-activated von willebrand factor to bind platelet glycoprotein, revealed by single-molecule stretching and imaging. J Mol Biol. Mar. 29, 2019;431(7):1380-1396. Epub Feb. 22, 2019.
Jiang et al., Stretching DNA to twice the normal length with single-molecule hydrodynamic trapping. Lab Chip. May 19, 2020;20(10):1780-1791.
Mendoza et al., Probing protein structure by amino acid-specific covalent labeling and mass spectrometry. Mass Spectrom Rev. Sep.-Oct. 2009;28;(5):785-815.
Pinheiro et al., Challenges and opportunities for structural DNA nanotechnology. Nat Nanotechnol. Nov. 6, 2011;6(12):763-72.
Silver et al., Tethered-bead, immune sandwich assay. Biosens Bioelectron. Jan. 15, 2015;63:117-123. Epub Jul. 11, 2014.
Thompson et al., Precise nanometer localization analysis for individual fluorescent probes. Biophys J. May 2002;82(5):2775-83.
Ueno et al., Simple dark-field microscopy with nanometer spatial precision and microsecond temporal resolution. Biophys J. May 19, 2010;98(9):2014-23.
Van Oijen et al., Single-molecule kinetics of lambda exonuclease reveal base dependence and dynamic disorder. Science. Aug. 29, 2003;301(5637):1235-8.
Yang et al., Repurposing a Benchtop Centrifuge for High-Throughput Single-Molecule Force Spectroscopy. Methods Mol Biol. 2018;1665:353-366.
U.S. Appl. No. 15/578,962, filed Dec. 1, 2017, Granted, U.S. Pat. No. 11,396,650.
U.S. Appl. No. 17/845,914, filed Jun. 21, 2022, Published, 2023-0045556.
U.S. Appl. No. 15/533,473, filed Jun. 6, 2017, Granted, U.S. Pat. No. 11,198,900.
U.S. Appl. No. 16/074,952, filed Aug. 2, 2018, Allowed, 2019-0048409.
U.S. Appl. No. 16/087,500, filed Sep. 21, 2018, Granted, U.S. Pat. No. 10,919,037.
U.S. Appl. No. 16/088,006, filed Sep. 24, 2018, Published, 2020-0116712.
U.S. Appl. No. 16/765,375, filed May 19, 2020, Granted, U.S. Pat. No. 11,591,636.
U.S. Appl. No. 18/168,131, filed Feb. 13, 2023, Pending.
U.S. Appl. No. 14/356,282, filed May 5, 2014, Granted, U.S. Pat. No. 9,914,958.
U.S. Appl. No. 15/888,941, filed Feb. 5, 2018, Abandoned, 2018-0291434.
U.S. Appl. No. 17/907,763, filed Aug. 29, 2022, Published, 2023-0146476.

* cited by examiner

Latched Complex bound to the two complementary regions on the M13 scaffold

COMPOSITIONS AND METHODS FOR ANALYTE DETECTION USING NANOSWITCHES

RELATED APPLICATIONS

This application is a national stage filing under 35 U.S.C. § 371 of International Application No. PCT/US2016/039654, filed Jun. 27, 2016, which was published under PCT Article 21(2) in English, and which claims the benefit under 35 U.S.C. § 119(e) of U.S. provisional application Ser. No. 62/185,582, filed Jun. 27, 2015, each of which is incorporated by reference herein in its entirety.

BACKGROUND OF INVENTION

DNA has been used in the construction of dynamic nanostructures and devices that are based on the specific interactions between complementary base pairs. DNA-based molecular devices have previously been used for reporting transient molecular events and as probes to follow cellular pathways. These devices are based on conformational changes induced by changes in environment (e.g., pH, ionic strength) or by signaling (e.g., strand displacement).

SUMMARY OF INVENTION

This disclosure provides nucleic acid-based nanoswitches that bind to and thus can be used to detect and quantify specific nucleic acids, such as may be required for a nucleic acid based diagnostic assay. The nucleic acids may be detecting using a gel electrophoresis readout. Recognition of specific targets is reported by a conformational change between two different states of the nanoswitch. The 'open' state of the switch is a linear duplex formed by a single-stranded scaffold and a set of oligonucleotides. Typically at least two of the oligonucleotides contain single stranded extensions each of which bind to a region of the target. Target recognition and binding reconfigures the nanoswitch to form a loop thus changing it to the 'closed' state. The open and closed nanoswitches migrate differently on an agarose gel, indicating their relative quantity in the two possible states. These molecular switches are low-cost approaches for detection, quantification and purification of specific nucleic acids including for example RNAs in small quantities. Thus, provided herein are compositions and methods for detecting targets such as nucleic acids using nucleic acid-based nanoswitches.

Also provided herein are a collection of methods for holding a variety of nanoswitches in the closed or looped state, thereby facilitating detection and optionally quantitation and/or purification of a variety of targets including but not limited to target nucleic acids, target proteins, and the like. The ability to "freeze" a nanoswitch in such a conformation can facilitate the detection and characterization of a wide range of molecular interactions and thus a wide range of targets. In some instances, the conformation is maintained or stabilized through the use of a latch. The latches of this disclosure are designed to "close" when a transient interaction occurs between two moieties that are in close proximity on a nanoswitch as the latch moieties. When no transient interaction occurs between the other moieties, then the latch remains open. The latches can be used in instances in which the binding interaction occurring within the nanoswitch is not strong enough to keep the nanoswitch closed during later analysis such as gel electrophoresis. Such weak binding interactions are difficult to measure and detect. A latch that is capable of keeping a nanoswitch shut even if the primary binding interaction is weak, expands the range of targets and binding interactions that can be studied using such nanoswitches. This disclosure contemplates using the latches to detect weak interactions between two moieties attached to the nanoswitch, to detect targets by stabilizing a loop formed, for example by a sandwiching assay with two detection antibodies attached to the nanoswitch, to stabilize interactions between members of a compound library and target molecules for drug discovery/screening, and/or to purify targets using a nanoswitch separation assay. These applications and the required latch designs are described in greater detail herein.

This disclosure provides, in one aspect, a nucleic acid complex comprising a scaffold nucleic acid hybridized to a plurality of oligonucleotides, wherein a first and a second oligonucleotide in the plurality are partially hybridized to the scaffold nucleic acid, wherein the first oligonucleotide comprises a 3' overhang and the second oligonucleotide comprises a 5' overhang, wherein the 3' overhang is not complementary to the 5' overhang, and wherein if the 3' overhang and the 5' overhang are brought into close proximity to each other, a loop is formed in the nucleic acid complex, in the presence of a target nucleic acid that is complementary to both the 3' overhang and the 5' overhang.

In some embodiments, the 3' and 5' overhangs each has a length of 5 or more nucleotides, or 6 or more nucleotides, or 7 or more nucleotides. In some embodiments, the 3' and 5' overhangs are of the same length. In some embodiments, the 3' and 5' overhangs are of the different lengths. In some embodiments, the 3' overhang comprises a 3' hydroxyl and the 5' overhang comprises a 5' phosphate.

In some embodiments, the nucleic acid complex is hybridized to a target nucleic acid that is partially complementary to the 3' overhang and partially complementary to the 5' overhang.

In some embodiments, the target nucleic acid is a miRNA, mRNA or non-coding RNA.

In some embodiments, the complex comprises N pairs of target-specific oligonucleotides, wherein each pair of target-specific oligonucleotides hybridizes specifically to its respective target nucleic acid.

In some embodiments, a third and a fourth oligonucleotide in the plurality are partially hybridized to the scaffold nucleic acid, wherein the third oligonucleotide comprises a 3' overhang and the fourth oligonucleotide comprises a 5' overhang. In some embodiments, the third and fourth oligonucleotides are both upstream of the first oligonucleotide or downstream of the second oligonucleotide. In some embodiments, the first and second oligonucleotides are partially complementary to a first target nucleic acid, and the third and fourth oligonucleotides are partially complementary to a second target nucleic acid.

In some embodiments, the third and fourth oligonucleotides together flank the first and second oligonucleotides together (i.e., the third oligonucleotide is upstream of the first oligonucleotide and the fourth oligonucleotide is downstream of the second oligonucleotide). In some embodiments, the third and fourth oligonucleotides are nested between the first and second oligonucleotides (i.e., the first oligonucleotide is upstream of the third oligonucleotide and the second oligonucleotide is downstream of the fourth oligonucleotide). The third and fourth oligonucleotides may be latch oligonucleotides that bind to a trigger or latch nucleic acid once they are brought into close proximity with each other as a result of the occurrence of the first binding interaction.

In some embodiments, the 3' overhang of the third oligonucleotide and/or the 5' overhang of the fourth oligonucleotide adopt a hairpin conformation or other secondary structure or are capable of adopting a hairpin conformation or other secondary structure.

In some embodiments, the nucleic acid complex comprises a scaffold nucleic acid that is about 1000-10,000 nucleotides in length. In some embodiments, the nucleic acid complex comprises a scaffold nucleic acid that is about 5000-10,000 nucleotides in length. In some embodiments, the nucleic acid complex comprises a scaffold nucleic acid that is about 7000-7500 nucleotides in length.

In some embodiments, the nucleic acid complex comprises a plurality of oligonucleotides hybridized to a scaffold nucleic acid, wherein the oligonucleotides are each about 20-100 nucleotides in length. In some embodiments, the nucleic acid complex comprises a plurality of oligonucleotides hybridized to a scaffold nucleic acid, wherein the oligonucleotides are each about 40-80 nucleotides in length. In some embodiments, the nucleic acid complex comprises a plurality of oligonucleotides hybridized to a scaffold nucleic acid, wherein the oligonucleotides are each about 60 nucleotides in length.

The disclosure provides, in another aspect, a composition comprising one or more of any of the foregoing nucleic acid complexes. In some embodiments, the composition comprises a plurality of any of the foregoing nucleic acid complexes. In some embodiments, the nucleic acid complexes of the plurality are identical to each other. In some embodiments, the nucleic acid complexes of the plurality are different from each other. In some embodiments, the nucleic acid complexes of the plurality differ from each other in the sequence of the 3' overhang, and/or the sequence of the 5' overhang, and/or the distance between the 3' overhang and the 5' overhang along the length of the scaffold nucleic acid.

In some embodiments, the composition further comprises a nucleic acid sample. The nucleic acid sample may be or may have been derived from a bodily sample, such as but not limited to a blood sample.

In some embodiments, the composition comprises a target nucleic acid. In some embodiments, the composition comprises a first and a second target nucleic acid. In some embodiments, the composition comprises a plurality of different nanoswitches and a plurality of target nucleic acids.

In some embodiments, the composition comprises a ligase.

The disclosure provides, in yet another aspect, a method for detecting a target nucleic acid comprising providing any one of the foregoing nucleic acid complexes wherein the complex is hybridized to a bridge oligonucleotide that is partially complementary to the 3' and 5' overhangs, and the complex is thereby in a looped conformation, contacting the complex with a nucleic acid sample under conditions that allow a target nucleic acid, if present in the nucleic acid sample, to hybridize to the 3' overhang, or the 5' overhang, or the bridge oligonucleotides, thereby displacing the bridge oligonucleotide from the complex, and inducing the complex to adopt a linear conformation, and detecting the conformation of the nucleic acid complex, wherein a linear conformation indicates presence of the target nucleic acid in the sample.

The disclosure provides, in yet another aspect, a method for detecting a target nucleic acid comprising contacting any one of the foregoing nucleic acid complexes with a nucleic acid sample under conditions that allow a target nucleic acid, if present in the nucleic acid sample, to hybridize to the 3' overhang and the 5' overhang of the nucleic acid complex, and detecting conformation of the nucleic acid complex, wherein a looped conformation indicates presence of the target nucleic acid in the sample.

In some embodiments, the conformation of the nucleic acid complex is detected using gel electrophoresis. In some embodiments, the gel electrophoresis is bufferless gel electrophoresis. In some embodiments, the conformation of the nucleic acid complex is detected using liquid chromatography.

In some embodiments, the method further comprises measuring an absolute or relative amount of target nucleic acid. In some embodiments, the method further comprises isolating the target nucleic acid from sample or the nucleic acid complex.

In some embodiments, the conditions that allow a target nucleic acid to hybridize to the 3' overhang and the 5' overhang comprise a constant annealing temperature. In some embodiments, the conditions that allow a target nucleic acid to hybridize to the 3' overhang and the 5' overhang comprise a constant annealing temperature of about 25° C. In some embodiments, the conditions that allow a target nucleic acid to hybridize to the 3' overhang and the 5' overhang comprise a decreasing annealing temperature. In some embodiments, the conditions that allow a target nucleic acid to hybridize to the 3' overhang and the 5' overhang comprise a decreasing annealing temperature that spans about 46° C. to about 4° C.

In some embodiments, the nucleic acid sample is not an in vitro amplified nucleic acid sample. In some embodiments, the nucleic acid sample comprises nucleic acid that is non-target nucleic acid. In some embodiments, the nucleic acid sample comprises about 100 µM total or non-target nucleic acid. In some embodiments, the target nucleic acid is present in the sample at a pM concentration. In some embodiments, the nucleic acid sample comprises target nucleic acid in the nanomolar concentration. In some embodiments, the target nucleic acid is present in the sample at a concentration in the range of about 1 nM to 25 nM.

In some embodiments, the nucleic acid sample comprises target nucleic acid and non-target nucleic acid. In some embodiments, the target nucleic acid and non-target nucleic acid are present in the sample at a ratio of $1:10^2$, $1:10^3$, $1:10^4$, $1:10^5$, $1:10^6$, $1:10^7$, or $1:10^8$.

In some embodiments, the target nucleic acid is a DNA. In some embodiments, the target nucleic acid is a RNA. In some embodiments, the target nucleic acid is miRNA, mRNA or non-coding RNA, or a fragment thereof. In some embodiments, the target nucleic acid is a tumor-specific nucleic acid.

In some embodiments, the nucleic acid sample is derived from a bodily sample. In some embodiments, the bodily sample is a blood sample, a urine sample, a sputum sample, or a stool sample. In some embodiments, the target nucleic acid is an allelic variant. In some embodiments, the 3' overhang and 5' overhang each or together comprise 1 or 2 mismatch nucleotides relative to a wild-type sequence. In some embodiments, at least 1 of the mismatch nucleotides is located in the middle of the 3' or 5' overhang (i.e., at a position that is not an end nucleotide of the overhang).

In some embodiments, the combined length of the 3' overhang and the 5' overhang is the same length of the target nucleic acid. In some embodiments, the combined length of the 3' overhang and the 5' overhang is shorter than the length of the target nucleic acid. In some embodiments, the combined length of the 3' overhang and the 5' overhang is longer than the length of the target nucleic acid.

In some embodiments, the 3' overhang and the 5' overhang are of equal length. In some embodiments, the 3' overhang and the 5' overhang are of different lengths. In some embodiments, the 3' overhang and the 5' overhang are each about or at least 7, 8, 9, or 10 nucleotides in length. In some embodiments, the 3' overhang and the 5' overhangs have a combined length of about or at least 14 nucleotides. In some embodiments, the 3' overhang and the 5' overhangs have a combined length of 15, 16, 17, 18, 19, 20, 21 or 22 or more nucleotides. Some nanoswitches comprise 5' and 3' overhang combinations of 9 and 9 nucleotides, 10 and 10 nucleotides, 15 and 15 nucleotides, up to and including 20 and 20 nucleotides. A specific example comprises a 15 and 7 nucleotide overhang combination, yielding a 22 nucleotide overall detector length.

In some embodiments, the target nucleic acid is about 7-50 nucleotides in length.

In some embodiments, the target nucleic acid has more sequence complementarity to the 3' overhang than to the 5' overhang. In some embodiments, the target nucleic acid has more sequence complementarity to the 5' overhang than to the 3' overhang.

In some embodiments, the target nucleic acid comprises a 5' and/or a 3' sequence that does not hybridize to the nucleic acid complex.

In some embodiments, the method further comprises hybridizing another nucleic acid to the target nucleic acid, thereby creating a triplex. In some embodiments, the target nucleic acid or a portion of the target nucleic acid is polypurine sequence, the 3' overhang and/or the 5' overhang has a polypyrimidine sequence, and the other nucleic acid has a polypyrimidine sequence. In some embodiments, the target nucleic acid is about 10-50 nucleotides in length. In some instances, the target nucleic acid is 10-22 nucleotides in length.

In some embodiments, the method is a method of detecting a first and/or a second target nucleic acid, wherein the nucleic acid complex adopts different conformations in the presence of the first target nucleic acid, in the presence of the second target nucleic acid, and in the combined presence of the first and second target nucleic acids. In some embodiments, the nucleic acid complex comprises a third oligonucleotide and a fourth oligonucleotide that are partially complementary to a second target nucleic acid.

In some embodiments, the method is used to genotype a sample. In some embodiments, the sample is fragmented genomic DNA. In some embodiments, the method further comprises harvesting the target nucleic acid from the nucleic acid complex.

The disclosure provides, in another aspect, a method for detecting a target nucleic acid comprising contacting any of the foregoing nucleic acid complexes with a target nucleic acid under conditions that allow the target nucleic acid to hybridize to the 3' overhang and the 5' overhang of the nucleic acid complex, wherein the 3' overhang comprises a 3' hydroxyl and the 5' overhang comprises a 5' phosphate, contacting the nucleic acid complex that is hybridized to the target nucleic acid with a ligase, thereby ligating the 3' overhang to the 5' overhang, and detecting a looped conformation of the nucleic acid complex.

The disclosure provides, in another aspect, a method for detecting a target nucleic acid comprising (1) contacting any one of the foregoing nucleic acid complexes with a target nucleic acid under conditions that allow the target nucleic acid to hybridize to the 3' overhang and the 5' overhang of the nucleic acid complex, wherein the 3' overhang comprises a 3' hydroxyl and the 5' overhang comprises a 5' phosphate, (2) contacting the nucleic acid complex that is hybridized to the target nucleic acid with a ligase, thereby ligating the 3' overhang to the 5' overhang, (3) dissociating the target nucleic acid from the nucleic acid complex, thereby allowing the target nucleic acid to contact another nucleic acid complex, (4) repeating steps (1) through (3) one or more times, and detecting a looped conformation of the nucleic acid complex.

The disclosure provides, in another aspect, a method for detecting a target nucleic acid in a sample comprising (1) contacting any one of the foregoing nucleic acid complexes with sample under conditions that allow a target nucleic acid, if present in the sample, to hybridize to the 3' overhang and the 5' overhang of the nucleic acid complex, wherein the 3' overhang comprises a 3' hydroxyl and the 5' overhang comprises a 5' phosphate, (2) contacting the nucleic acid complex with a ligase, thereby ligating the 3' overhang to the 5' overhang if the target nucleic acid is hybridized to the nucleic acid complex, (3) introducing conditions sufficient to dissociate a target nucleic acid from the nucleic acid complex, (4) introducing conditions that allow a target nucleic acid, if present, to hybridize to the 3' overhang and the 5' overhang of another, non-ligated, nucleic acid complex, (5) repeating steps (2) through (4) one or more times, and detecting conformations of the resultant nucleic acid complexes, wherein a looped conformation indicates presence of the target nucleic acid in the sample.

In some embodiments, the target nucleic acid is present in the sample at a concentration in the range of 1 zeptomolar to 1 nanomolar. In some embodiments, a single copy of the target nucleic acid is present in the sample.

In some embodiments, the conditions that allow a target nucleic acid to hybridize to the 3' and 5' overhangs of the nucleic acid complex comprise a temperature in the range of about 4° C. to 25° C. In some embodiments, conditions sufficient to dissociate a target nucleic acid from the nucleic acid complex comprise an increase in temperature. In some embodiments, conditions sufficient to dissociate a target nucleic acid from the nucleic acid complex comprise a temperature above 25° C. In some embodiments, the method is performed using a thermo-cycler.

In some embodiments, ligase is present during steps (1) through to (4) or steps (1) through (5).

In some embodiments, conformations of the resultant nucleic acid complexes are detected using gel electrophoresis.

In some embodiments, the hybridization of the target nucleic acid to the nucleic acid complex is stabilized in the presence of magnesium, and the gel electrophoresis is performed in the absence of magnesium. In some embodiments, the hybridization of the target nucleic acid to the nucleic acid complex is stabilized in the presence of magnesium, and the gel electrophoresis is performed in the presence of magnesium, and optionally in sub-optimal concentrations of magnesium.

In some embodiments, the target nucleic acid is weakly hybridized to the 3' overhang or the 5' overhang. In some embodiments, the binding interaction between the target nucleic acid and the 3' overhang or the 5' overhang or the 3' overhang and the 5' overhang combined has a Kd greater than 1 nM.

The disclosure provides, in another aspect, a method comprising (1) placing a nucleic acid complex comprising a first and a second binding partner under conditions that allow for binding of the first and second binding partners to each other, wherein the first and second binding partners are attached to first and second oligonucleotides respectively, (2) contacting the nucleic acid complex with a ligase and a trigger nucleic acid that is partially complementary to a third and a fourth oligonucleotide in the nucleic acid complex under conditions that allow ligation of a third and a fourth oligonucleotide, each comprising either a 3' hydroxyl or a 5' phosphate, (3) dissociating the trigger nucleic acid from the third and fourth oligonucleotides, (4) optionally repeating steps (1) through (3) one or more times, and detecting conformations of the resultant nucleic acid complexes, wherein a looped conformation indicates binding of the first binding partner to the second binding partner. The nucleic acid complex comprises a scaffold nucleic acid hybridized to a plurality of oligonucleotides, wherein a first oligonucleotide in the plurality is linked to the first binding partner, a second oligonucleotide in the plurality is linked to the second binding partner, a third oligonucleotide located upstream of the first oligonucleotide is partially hybridized to the scaffold nucleic acid and comprises the 3' overhang having a 3' hydroxyl, and a fourth oligonucleotide located downstream of the second oligonucleotide is partially hybridized to the scaffold nucleic acid and comprises a 5' overhang having a 5' phosphate.

In some embodiments, the first and second binding partners bind to each other directly. In some embodiments, the first and second binding partner bind to each other indirectly. In some embodiments, the conformations of the resultant nucleic acid complexes are determined using gel electrophoresis.

The disclosure provides, in another aspect, a method for stabilizing a first binding interaction in a nanoswitch, comprising providing a nucleic acid-based nanoswitch in a looped conformation as a result of a first binding interaction of the nanoswitch with a target, and inducing a latch binding interaction in the nanoswitch, thereby stabilizing nanoswitch in the looped conformation.

In some embodiments, the latch binding interaction is externally triggered via introduction of trigger moieties, and/or via photoactivation, force application, heating, change in solution conditions, change in concentration or presence of ions or atoms in solution.

In some embodiments, the latch binding interaction is a covalent. In some embodiments, the covalent latch binding interaction involves crosslinking, click chemistry bonds, and sortase mediated binding.

In some embodiments, the latch binding interaction is non-covalent. In some embodiments, the non-covalent latch binding interaction involves nucleic acid hybridization, receptor-ligand binding, biotin-avidin binding, biotin-streptavidin binding, or nucleic acid and protein binding.

In some embodiments, the nanoswitch comprises amine and sulfhydryl reactive groups or a pair of amine groups, and the latch binding interaction comprises contacting the nanoswitch with SMCC or glutaraldehyde. In some embodiments, the amine and sulfhydryl reactive groups or a pair of amine groups are naturally present in the moieties involved in the first binding interaction.

In some embodiments, the amine and sulfhydryl reactive groups or a pair of amine groups are attached to the nanoswitch at a position in close proximity to the location of the moieties involved in the first binding interaction.

In some embodiments, the latching binding interaction is reversible.

These and other aspects and embodiments of the invention will be described in greater detail herein.

BRIEF DESCRIPTION OF DRAWINGS

FIG. 2A is a scheme showing the construction of the DNA nanoswitch. FIG. 2B is an agarose gel image of the nanoswitch before and after purification.

FIG. 3A shows binding of the "symmetric" key oligonucleotides to the nanoswitch. Closure length was varied from 15-nt to 10-nt. FIG. 3B shows "asymmetric" key oligonucleotides with closure lengths varying from 15-nt to 5-nt (with a* being 15-nt). The top part shows details of the key binding and lower part shows agarose gel results from samples that were annealed and kept at room temperature.

FIG. 4A presents agarose gels showing the binding of different key oligonucleotides at four different concentrations (25 nM, 12.5 nM, 6.25 nM, 1.25 nM). FIG. 4B shows the looped intensity of the on-state switches measured in comparison to the reference band (indicated) from the pBR digest. The bars in FIG. 4B correspond to the same concentrations as shown in FIG. 4A, such that the first, second, third and fourth bars correspond to 25 nM, 12.5 nM, 6.25 nM, 1.25 nM.

FIG. 5A shows a view of two detector strands (det-1 and det-2) and binding of the key oligonucleotide. The length of the key oligonucleotide can be varied. FIG. 5B shows the temperature dependent binding of the detector strands on to the scaffold. FIG. 5C shows the UV melting profiles of the complete binding of the key oligonucleotides to both detectors. FIGS. 5D and 5E present UV melting profiles showing affinity of the key oligonucleotides to detector 1 and detector 2 respectively, with shorter keys having lower melting temperatures.

FIG. 6A is an agarose gel shows the sequence specificity of the nanoswitch. Switch X (blue) turns on only in the presence of key oligonucleotide X (blue) and switch Y turns on only in the presence of key oligonucleotide Y with no background detection of the incorrect strand. FIG. 6B shows that the DNA nanoswitch can successfully detect the target sequence, even when competing random sequences are present in large molar excess.

FIG. 7A shows that different concentrations of random oligo mixtures do not affect the nanoswitch. There is no false positive detection even at 50 µM of random sequence oligos, which is roughly 100,000 times higher molar concentration than the nanoswitches themselves. FIG. 7B shows that the DNA nanoswitch turns "on" only when the specific key oligonucleotide is added and the addition of a mixture of random oligos has little effect on the switch.

In FIG. 8A show the normalized fraction of nanoswitches in the on-state after specific time intervals. Gel results are shown within the graph at different time points. FIG. 8B shows a gel read-out at different gel running times. Separation of the on- and the off-state is clearly visible even after 20 minutes. The experiment was done both at 25° C. and 4° C. FIG. 8C is a scheme showing the fast, label-free detection strategy. Detection of the target sequence happens in 10 minutes and can be read-out using gel electrophoresis within 20 minutes.

FIG. 13A is a schematic illustrating the design strategy and FIG. 13B shows the distinct gel mobility of each target loop.

DETAILED DESCRIPTION

Figure 1A:
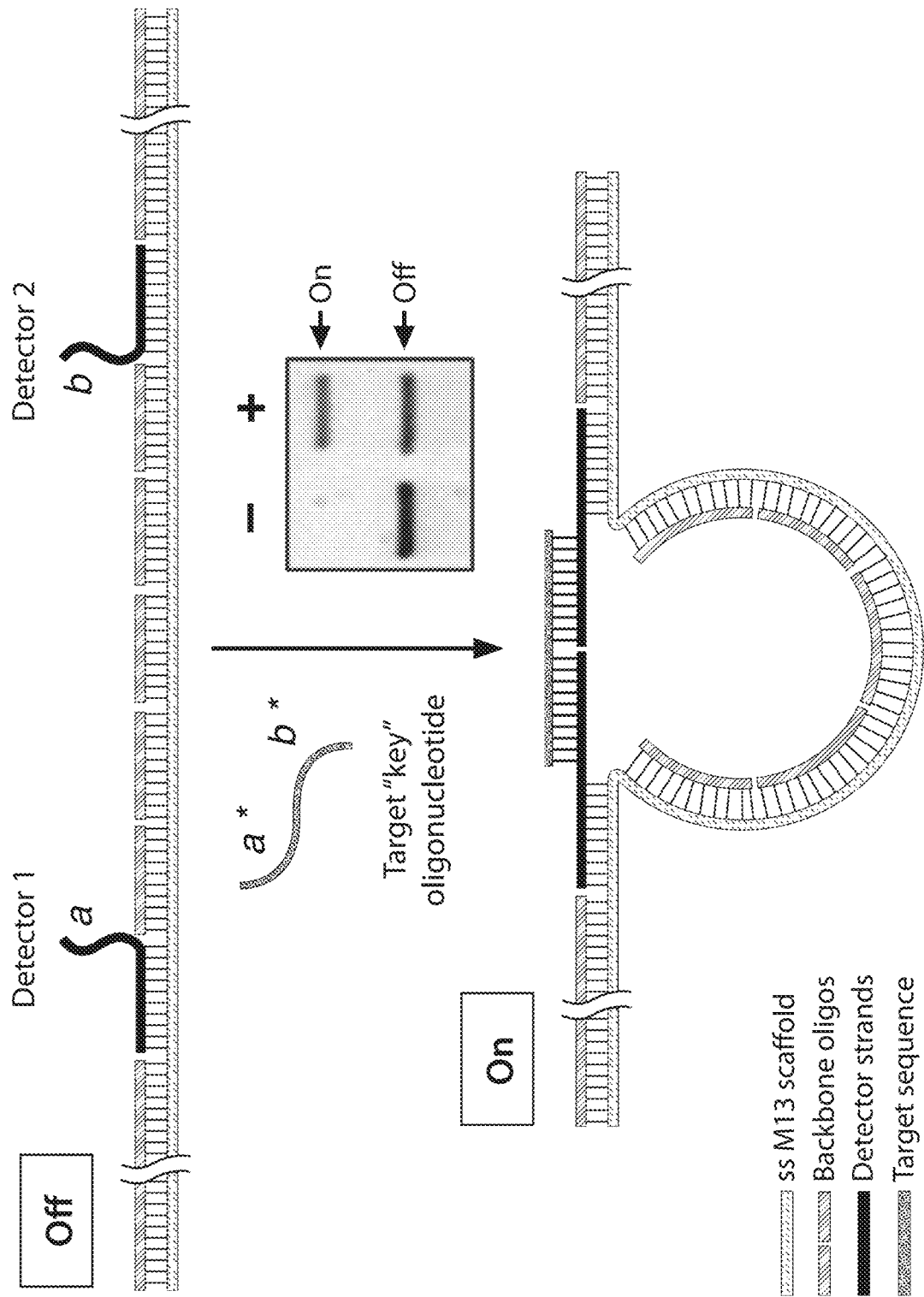
FIG. 1A shows the design and operation of the two-state DNA nanoswitch. A double stranded DNA is made with a single-stranded scaffold (pink), complementary backbone oligos (blue), and detector strands (yellow) that can be addressably inserted at different locations. Addition of the key oligonucleotide (red) binds the overhangs of the two detector regions 'a' and 'b' thereby forming a loop. This conformational change can be read out using gel electrophoresis (inset).
Figure 1B:
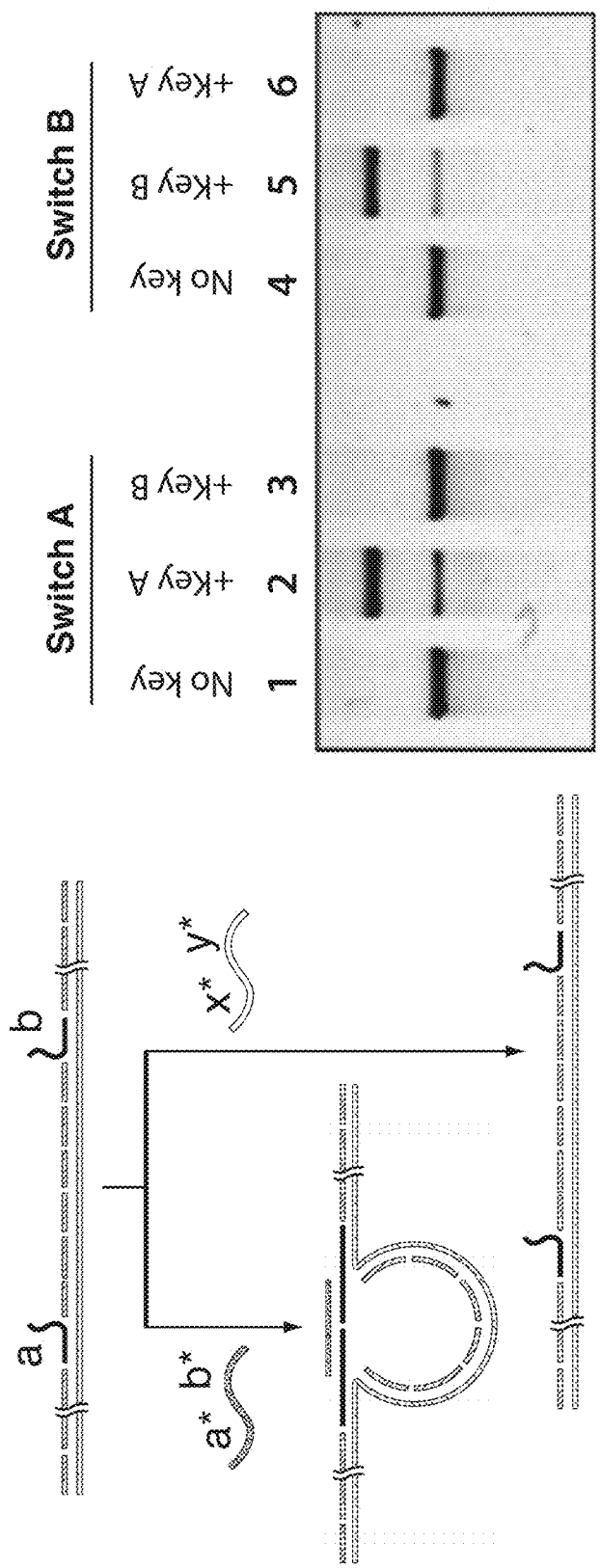
FIG. 1B shows the sequence specificity of DNA nanoswitches. An agarose gel showing the sequence specificity of the nanoswitch. Switch A turns on only in the presence of key oligonucleotide A and switch B turns on only in the presence of key oligonucleotide B with no background detection of the incorrect strand.

The disclosure provides nucleic acid complexes, also referred to herein as nanoswitches, for use in detecting targets. Targets are detected based on their binding interactions with the nanoswitches and the conformational changes that are induced in the nanoswitches as result of such binding. The nanoswitches are designed so that in the absence of the target they typically assume a linear (or open) conformation and in the presence of target they assume a looped (or closed) conformation. As will be discussed in greater detail herein, the nanoswitches can also be designed to maintain such closed conformations even in the absence of a bound target, through the use of a latching mechanism. These conformations are detected and physically separable from each other using various techniques including but not limited to gel electrophoresis. In the context of gel electrophoresis, the open and closed conformations migrate to different extents through a gel, and they can be excised from the gel in order to, in some instances, further study and/or isolate the target that is bound to the nanoswitch.

The nanoswitches are further designed to detect a variety of targets, including but not limited to targets that are nucleic acids or proteins or peptides. Typically, the nanoswitch comprises or is bound to a binding partner for a target of interest. The binding partner may be a nucleic acid that binds to a target that is a nucleic acid based on sequence complementarity. The binding partner may be an antibody or an antibody fragment that binds specifically to the target of interest.

Various aspects of this disclosure relate to the use of nanoswitches to detect targets that are nucleic acids, such targets being referred to herein as target nucleic acids. Detection of nucleic acids such as DNA is important for a variety of applications including for example in the fields of medicine and forensics. Many currently available detection strategies involve multiple time consuming steps and/or require expensive detection equipment. This disclosure provides a programmable nucleic acid-based nanoswitch that undergoes a pre-defined conformational change upon binding a target nucleic acid, thereby converting the nanoswitch from a linear "off" state (or conformation) to a looped "on" state (or conformation). The presence of the target nucleic acid is determined without enzyme-based amplification such as PCR and the like. Instead, the presence of the target nucleic acid can be detected using separation techniques such as standard gel electrophoresis, which are capable of physically separating the open and closed conformations from each other and from other components in a mixture, and in some instances also are capable of facilitating isolation of the nanoswitch and its bound target.

The disclosure demonstrates successful detection of a single target nucleic acid from a randomized pool of high concentration oligonucleotides with no false positive detection. The detection method can be accomplished quickly, including as demonstrated herein within 30 minutes from sample mixture to readout. The approach is a low cost and technically accessible, and thus well-suited for point-of-use detection.

In addition, the nucleic acid complexes may also be used to detect more than one target nucleic acid simultaneously or consecutively. For example, the nucleic acid complex may be designed to hybridize to one, two or more target nucleic acids, with a different, discernable structure resulting from each.

The disclosure further provides nanoswitches capable of maintaining a looped conformation even in the absence of a target. As used herein, such nanoswitches comprise a "latch". The latch is an additional binding interaction that occurs within a nanoswitch, only once the target-associated binding interaction occurs. The latch binding interaction can serve to stabilize, including to essentially "freeze", an existing looped conformation, regardless of whether the target continues to be bound to the nanoswitch. These latch binding interactions are contemplated for use, inter alia, in the detection of low or single copy targets. As will be understood in view of this disclosure, the nanoswitches comprising latches can be used in the detection (or simply binding) of a variety of targets and are not limited solely to use with target nucleic acids.

Nucleic Acid Complexes/Nanoswitches Generally

A nucleic acid complex, as described herein, minimally comprises a scaffold nucleic acid hybridized in a sequence specific manner to a plurality of oligonucleotides. The scaffold and the oligonucleotides may be referred to herein as being single-stranded. This intends that prior to hybridization to each other, both nucleic acid species are single-stranded. Upon hybridization, a double-stranded nucleic acid is formed, as should be understood. Typically, the oligonucleotides hybridize to the scaffold nucleic acid in a consecutive, non-overlapping, manner.

In some non-limiting embodiments, the nucleic acid complexes are formed by hybridizing a scaffold nucleic acid to one or more oligonucleotides. The disclosure contemplates any variety of means and methods for generating the nucleic acid complexes described herein. It is also to be understood that while for the sake of brevity the disclosure refers to oligonucleotides that are hybridized to a scaffold nucleic acid, such a complex may have been formed by hybridizing single stranded scaffold to single stranded oligonucleotides, but it is not intended that it was exclusively formed in this manner. Other ways of generating nucleic acid complexes having the same structure can be used and are contemplated by this disclosure.

The nucleic acid complexes may comprise double-stranded and single-stranded regions. As used herein, a double-stranded region is a region in which all nucleotides on the scaffold are hybridized to their complementary nucleotides on the oligonucleotide. Double-stranded regions may comprise "single-stranded nicks" as the hybridized oligonucleotides typically are not ligated to each other. The single-stranded regions are scaffold sequences that are not hybridized to oligonucleotides. Certain complexes may comprise one or more single-stranded regions in between double-stranded regions (typically as a result of unhybridized nucleotides in between adjacent hybridized oligonucleotides). The complexes may be at least 50%, at least 60%, at least 70%, at least 80%, at least 90%, at least 95%, at least 96%, at least 97%, at least 98%, at least 99%, or 100% double-stranded. In some embodiments, they are at least 80% double stranded.

As will be apparent based on this disclosure, the nucleic acid complexes are modular complexes to which can be attached one or more targets of interest, one or more binding pairs of interest, and the like. The nucleic acid complexes may be capable of detecting one or more nucleic acids, and may comprise one or more latches.

The terms attach, link and conjugate are used interchangeably throughout this disclosure unless otherwise stated.

The switches provided herein are stable in complex fluids such as but not limited to serum-containing samples, including up to 30% FBS. The ability of the switches to convert from unbound to bound forms in the presence of complex fluids (e.g., 30% FBS) has also been demonstrated (data not shown). This indicates that the switches are amenable to use with harvested primary samples (e.g., biopsy or fluid sample from a subject). Moreover, the switches are also stable for an extended period of time. Once synthesized, the switches may be dried and stored for days, weeks or months. If stored at −20° C., the switches are stable for at least 1 month (data not shown).

Synthesis

The nucleic acid complexes can be made using nucleic acid nanostructure techniques such as but not limited to DNA origami. (Rothemund P. W. K. (2006) Nature 440: 297-302; Douglas S. M. et al. (2009) Nature 459: 414-8). In DNA origami, a scaffold nucleic acid is hybridized in a one-pot synthesis scheme to a plurality of oligonucleotides, some or all of which bind to the scaffold in a non-contiguous, non-linear, manner. A similar hybridization approach is taken here for the synthesis of the nucleic acid complexes. However, in contrast to DNA origami, the nucleic acid complexes of this disclosure comprise oligonucleotides that hybridize to the scaffold in a contiguous, linear, manner along their entire length. The conformational change that occurs in the nucleic acid complexes of the invention result from a binding interaction between the nucleic acid complex and a moiety extrinsic to the complex such as a target.

The nanoswitches may be formed by hybridizing the scaffold nucleic acid and all the oligonucleotides at one time (e.g., in a one-pot synthesis method). Alternatively, the nanoswitches may be formed by first hybridizing the unmodified (or fixed) oligonucleotides to the scaffold nucleic acid to form a nucleic acid complex intermediate, and then hybridizing the modified (or variable) oligonucleotides to the scaffold nucleic acid to form the nucleic acid complex (or nanoswitch). The different types of modified oligonucleotides may be combined with (and typically hybridized to) the scaffold simultaneously or sequentially. As used herein, a nucleic acid complex intermediate refers to a scaffold hybridized to some but not the entire complement of oligonucleotides that is designed to bind to the entire length of the scaffold. Thus, in a nucleic acid complex intermediate, the scaffold will be partially single-stranded.

Scaffolds

The scaffold nucleic acid may be of any length sufficient to allow association (i.e., binding) and dissociation (i.e., unbinding) of binding partners to occur and to be distinguished from other association and/or dissociation events using the read out methods provided herein, including gel electrophoresis.

In some instances, the scaffold nucleic acid is at least 500 nucleotides in length, and it may be as long as 50,000 nucleotides in length (or it may be longer). The scaffold nucleic acid may therefore be 1000-20,000 nucleotides in length, 1000-15,000 nucleotides in length, 1000-10,000 in length, or any range therebetween. In some embodiments, the scaffold ranges in length from about 5,000-10,000 nucleotides, and may be about 7000-7500 nucleotides in length or about 7250 nucleotides in length.

The scaffold may be a naturally occurring nucleic acid (e.g., M13 scaffolds such as M13mp18). M13 scaffolds are disclosed by Rothemund 2006 Nature 440:297-302, the teachings of which are incorporated by reference herein. Such scaffolds are about 7249 nucleotides in length.

The scaffold nucleic acid may also be non-naturally occurring nucleic acids such as polymerase chain reaction (PCR)-generated nucleic acids, rolling circle amplification (RCA)-generated nucleic acids, etc. It is important that the scaffold nucleic acid is rendered single-stranded either during or post synthesis. Methods for generating a single-stranded scaffold include asymmetric PCR. Alternatively, double-stranded nucleic acids may be subjected to strand separation techniques in order to obtain the single-stranded scaffold nucleic acids. The scaffold nucleic acid may comprise DNA, RNA, DNA analogs, RNA analogs, or a combination thereof, provided it is able to hybridize in a sequence-specific and non-overlapping manner to the oligonucleotides. In some instances, the scaffold nucleic acid is a DNA.

Oligonucleotides

The scaffold nucleic acid is hybridized to a plurality of oligonucleotides. Each of the plurality of oligonucleotides is able to hybridize to the scaffold nucleic acid in a sequence-specific and non-overlapping manner (i.e., each oligonucleotide hybridizes to a distinct sequence in the scaffold).

The length and the number of oligonucleotides used may vary. In some instances, the length and sequence of the oligonucleotides is chosen so that each oligonucleotide is bound to the scaffold nucleic acid at a similar strength. This is important if a single condition is used to hybridize a plurality of oligonucleotides to the scaffold nucleic acid, such as for example in a one-pot synthesis scheme.

It will be understood that the number of oligonucleotides will depend in part on the application, the length of the scaffold, and the length of the oligonucleotides themselves. In some instances, the oligonucleotides are designed to be of approximately equal length. In some embodiments, the oligonucleotides may be about 20-100 nucleotides in length. The oligonucleotides may be, without limitation, about 20, about 30, about 40, about 50, about 60, about 70, about 80, about 90 or about 100 nucleotides in length. In some embodiments, the oligonucleotides may be about 40-80 nucleotides in length. In some embodiments, the oligonucleotides may be about 60 nucleotides in length.

The number of oligonucleotides in the plurality may be about 70, about 80, about 90, about 100, about 110, about 120, about 130, about 140, about 150, about 160, about 170, about 180, about 190, about 200, about 300, about 400, about 400, about 500, about 600, about 700, about 800, about 900, or about 1000, without limitation.

In some embodiments and as described in the Examples, the nucleic acid complex may comprise the M13 ssDNA as the scaffold and about 120 oligonucleotides each equal to or about 60 nucleotides in length.

Oligonucleotide Modifications

Typically, the majority of the oligonucleotides are unmodified, and these may be referred to herein as unmodified, fixed or backbone oligonucleotides. The fixed oligonucleotides typically hybridize to the scaffold throughout their length leaving no overhang and no single-base mismatch (i.e., they are typically fully complementary to a contiguous (linear) nucleotide sequence in the scaffold). Unmodified oligonucleotides include oligonucleotides that are not linked to binding partners (e.g., an antibody or an antigen) or linkers designed to attach the nanoswitch to a solid support such as but not limited to a bead (e.g., biotin).

A subset of the oligonucleotides may be modified, and these may be referred to herein as variable oligonucleotides. The variable oligonucleotides may be conjugated to reactive groups that are not normally present in a nucleic acid sequence, such as for example click chemistry reactive groups, or they may be conjugated to target-specific binding partners such as antibodies or antibody fragments, or they may comprise other moieties which are not typically present in an unmodified oligonucleotide. An example is a variable oligonucleotide comprising a phosphate at their 5' end (referred to herein as a 5' phosphate). Oligonucleotides having this latter modification are used herein in the detection of target nucleic acids, and in this context such oligonucleotides are referred to as "detector" strands since they detect the target nucleic acid via hybridization.

In some instances, the first and last oligonucleotides as well as "internal" oligonucleotides, typically at pre-defined positions along the length of the scaffold, may be modified oligonucleotides. The position of the variable oligonucleotides may be, but are not necessarily, evenly distributed along the length of the scaffold.

Binding Interactions and Looped Conformations

Figure 1C:
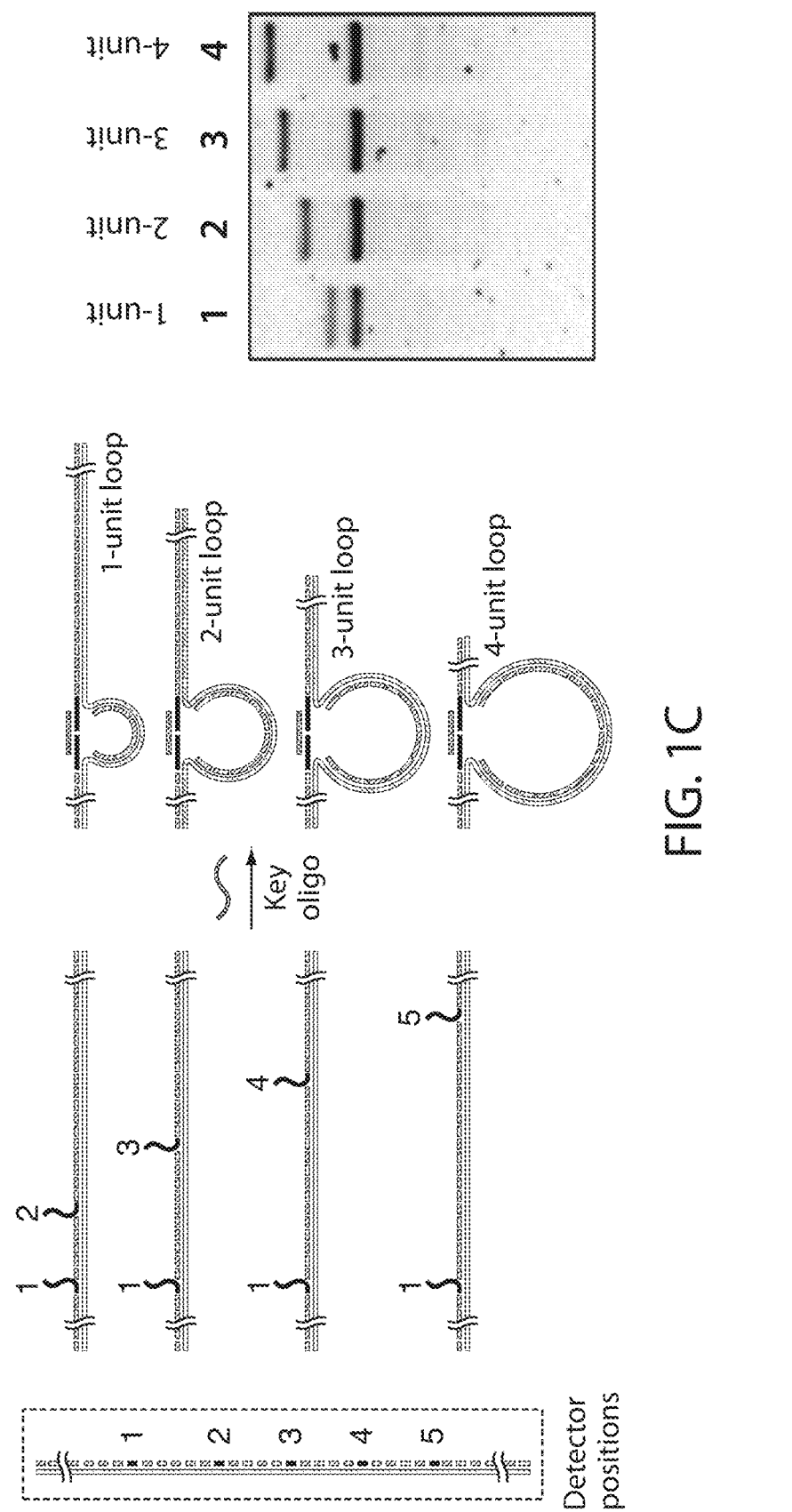
FIG. 1C shows the loop size configuration of the on state. The left panel shows detector positions on the nanoswitch are shown in green. The middle panel shows the combination of two positions, which gives different loop sizes on recognition of the key oligonucleotide. The right panel shows that different loop sizes can be identified using a gel read out. Larger loop sizes provide a shorter read-out time.

As will be apparent in the context of this disclosure, the location of the variable oligonucleotides dictates the location of the various substituents in the complex, such as detector strands, binding partners, latches, etc. It also dictates the size of the loops that are formed once the various substituents bind to each other, as shown in FIGS. 1A and 1C. This will in turn dictate the migration distance of the looped (closed) complex, and thus the ability of the end user to physically separate and thus distinguish between complexes of interest (e.g., closed complexes) and those not of interest (e.g., open complexes).

Embodiments described herein may refer to certain variable oligonucleotides as "first" or "second" or "third" or "fourth" oligonucleotides. It is to be understood that these designations are intended to impart clarity, and may or may not refer to position of the oligonucleotide along the length of the scaffold. For example, in the context of detecting target nucleic acids, this disclosure refers to the nanoswitch comprising a first and a second oligonucleotide that together hybridize to a target nucleic acid. In these embodiments, the hybridization of the nanoswitch to the target nucleic acid is considered the first binding interaction. The second binding interaction may be a latch binding interaction, as described in greater detail herein. Alternatively, the second binding interaction may be an additional binding interaction that occurs upon hybridization of a second target nucleic acid. In still other embodiments, the binding interactions associated with detecting a target nucleic acid may each have their own latch binding interaction.

In the simplest embodiment, the nanoswitch is designed to detect one target nucleic acid by hybridization of that target to a first oligonucleotide and a second oligonucleotide, each having an overhang (i.e., a single-stranded region that is available for hybridization to the target nucleic acid). Such overhangs are shown in FIG. 1A. The first and second oligonucleotides, in this example, may be referred to as partially hybridized to the scaffold since each has a single-stranded overhang region and a region that is hybridized to the scaffold. The first and second oligonucleotides are denoted "detector 1" and "detector 2". The overhangs may be referred to herein as 3' overhangs and 5' overhangs, referring to the directionality of the single-stranded region. The distance between the first and the second oligonucleotides, when bound to the scaffold, dictates the size of the loop and ultimately the migration distance of the nanoswitch when it is bound to the target (or when it is stabilized) via a latch binding interaction.

In some embodiments, the first oligonucleotide and the second oligonucleotide are separated from each other by 100-6000 nucleotides. In some instances, the first oligonucleotide and the second oligonucleotide are separated from each other by 500 to 5000 nucleotides, 600-5000 nucleotides, 1000-5000 nucleotides, or 1000-3000 nucleotides. In some embodiments, the first oligonucleotide and the second oligonucleotide are separated from each other by at least 500, 600, 700, 800, 900, 1000, 1500, 2000, 2500, 3000, 3500, 4000, 4500, 5000, 5500, 6000, or more nucleotides. In some embodiments, the first oligonucleotide and the second oligonucleotide are located about equi-distant about the center of the scaffold nucleic acid. In some embodiments, the first and second oligonucleotides bind to regions of the scaffold nucleic acid that are internal to the scaffold (i.e., such regions exclude the most 5' and the most 3' nucleotides of the scaffold).

Gel Electrophoresis

When measured using gel electrophoresis, the open and closed conformations migrate differentially. A circular scaffold such as circular M13 migrates the slowest, a linearized double-stranded version of M13 (without internal binding interactions) migrates fastest, and nanoswitches in looped conformations migrate in between. Importantly, the migration distance differs based on the length of the loop. As an example, loops that are on the order of about 2590 base pairs are clearly distinguishable from loops that are on the order of about 600 base pairs. Loops of other sizes can also be distinguished from each other, as described herein, and as demonstrated for example in FIG. 1C. The ability to distinguish between loops of different sizes means that the presence (or absence) of a multiple targets (each detected by a complex having a loop of a particular size) can be determined simultaneously in a multiplexed assay. Such methods may be used to detect the presence of a single or multiple targets and may form the basis of a diagnostic assay. Moreover, it should also be understood that nanoswitches having one loop can also be distinguished from nanoswitches having more than one loop, including those that have 2, 3 or more loops. This is demonstrated in FIGS. 13A and 13B, in which a single type of nanoswitch can be used to detect two different targets, and depending on the conformation of the nanoswitch (as determined by its migration distance in a gel), an end user can determine whether either or both targets are present in a sample. These nanoswitches can then also be extracted from the gel and the bound targets can be isolated.

Figure 13B:
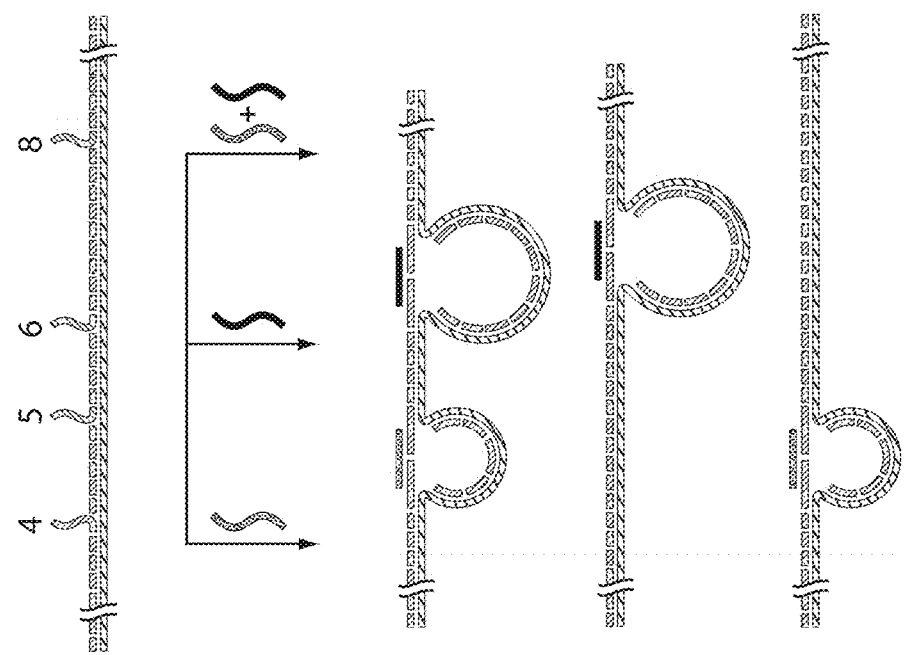
FIGS. 13A-13B show the simultaneous detection of multiple sequences.
Figure 13A:
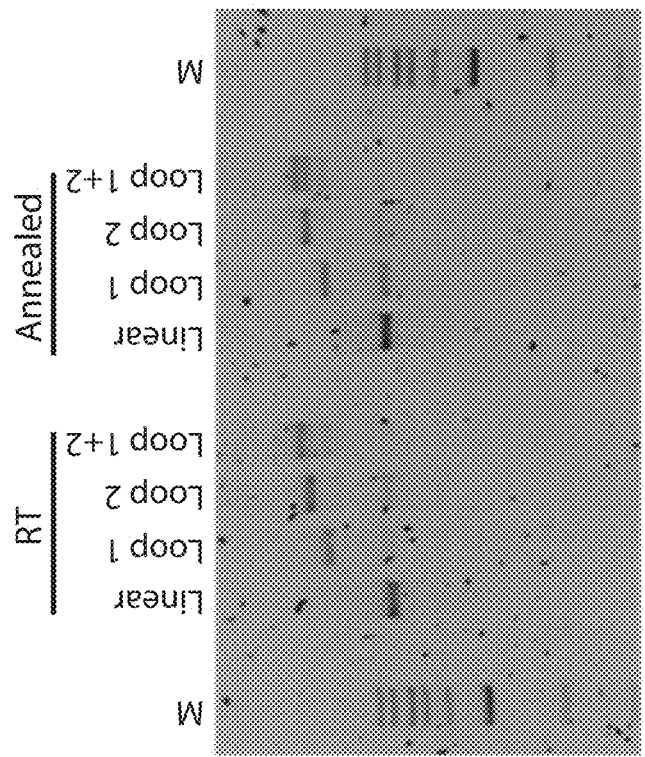
Figure 13C:
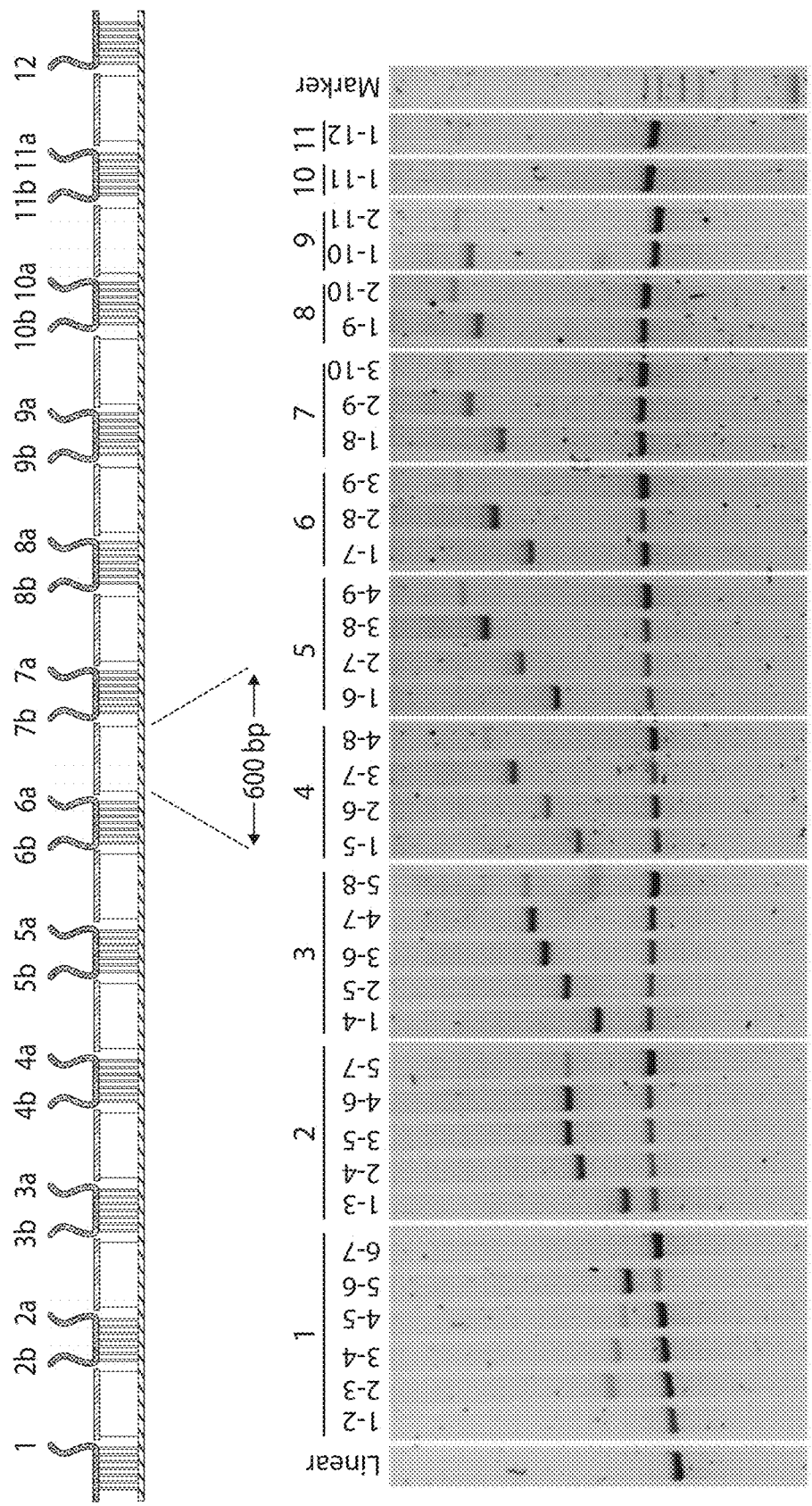
FIG. 13C illustrates loop size and position and migration through a gel.

FIG. 13C illustrates the variety of distinguishable gel migrations that can be achieved using a prototype nanoswitch. The nanoswitch is schematically shown at the top of the Figure. As illustrated, the nanoswitch contains multiple sets of detectors. Targets can be chosen to trigger loop formation between specific detector pairs. The loop size and position along the length of the nanoswitch affects the migration of the switch through the gel, as shown in the lower panel. (B) A gel showing the migration of different loop sizes (denoted as "loop-units" from 1 to 11) and loop positions on the switch (for example: 1-2 loop will be at the terminus of the switch while 6-7 will be at the center of the switch) is provided. The ability to distinguish the variety of loops based on size and position is clear. Accordingly, such a switch may be readily designed for multiplexing purposes (e.g., detection of two or more, including 3, 4, 5, 6, 7, 8, 9, 10, or more, nucleic acid targets in a sample).

Figure 13D:
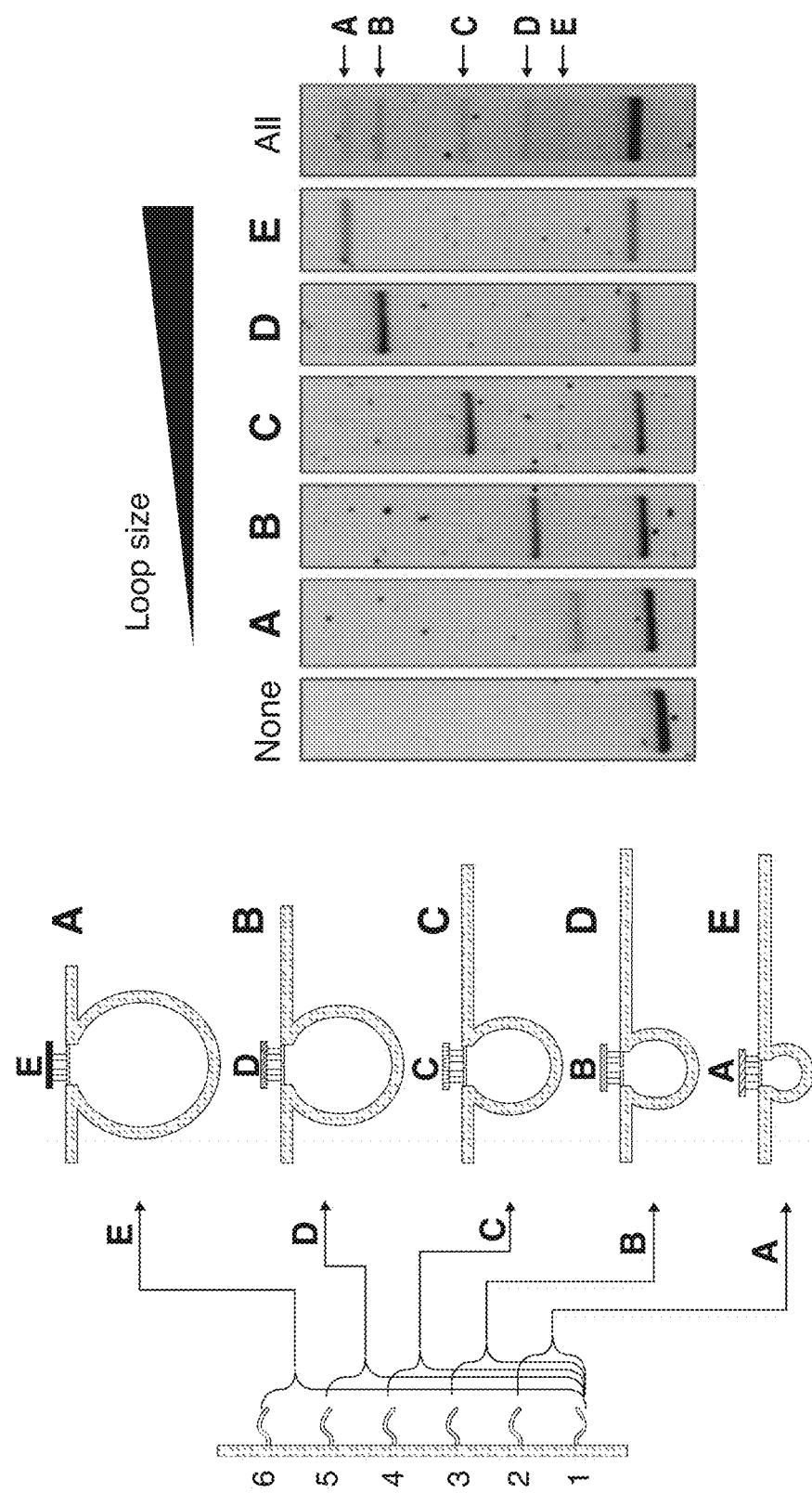
FIG. 13D illustrates another nanoswitch embodiment capable of multiplexed detection.

FIG. 13D illustrates another nanoswitch system that can be used for multiplexed detection. In this embodiment, the nanoswitch is designed such that all targets of interest bind a common detector sequence but different targets bind an additional unique specific detector sequence. This is illustrated in the middle panel where 5 different looped forms can be achieved using a nanoswitch having 6 detector sequences. The gel shows the ability to distinguish between the 5 different forms. Further demonstrated is the ability to generate all 5 forms in a single reaction when all 5 different targets are present (see gel denoted "All"). Such a programmable nanoswitch may be designed using any variety of detector sequences. Significantly, the nanoswitches in this set are each able to bind to only a single target, thus adopting only one looped form. This is in contrast to other nanoswitches that may bind two or more targets each.

In some instances, the gel is run at 4° C. to maintain the interaction of the targets to their binding partners (e.g., the binding of a protein target to target-specific antibodies) or to maintain the latch binding interactions.

Nucleic Acid Detection Nanoswitches

In some embodiments of this disclosure, nanoswitches designed for nucleic acid detection are provided. Such nanoswitches comprise a scaffold nucleic acid hybridized to a plurality of oligonucleotides, as described herein. A portion of an exemplary nanoswitch is provided in FIG. 1A. As illustrated, the nanoswitch comprises a first and a second oligonucleotide that are partially hybridized to the scaffold nucleic acid (i.e., each of these oligonucleotides is partially hybridized to the scaffold and thus each is partially single-stranded). The first oligonucleotide comprises a 3' overhang and the second oligonucleotide comprises a 5' overhang.

It is to be understood that the 3' overhang is not complimentary to the 5' overhang, and rather both the 3' and the 5' overhangs are complementary to a target nucleic acid. FIG. 1A illustrates an embodiment in which the entire target nucleic acid (referred to in the Figure as "Target "Key" oligonucleotide") hybridizes to a combination of the 3' and 5' overhang. However, the method can also be performed in which the 3' and 5' overhangs are designed to hybridize only the 5' and 3' regions of a target nucleic acid, with the internal or middle region of the target nucleic acid remaining unhybridized. In this latter instance, the nanoswitch is designed to detect a plurality of target nucleic acids of differing sequences provided that they are at least complementary to the 3' and 5' overhangs. In this case, the nanoswitch detects non-adjacent sequences on the target. Such non-adjacent sequences may be separated by 1 or 2 nucleotides or by 10's or 100's of nucleotides, without limitation.

It is further to be understood that the nanoswitch is designed such that the 3' and 5' overhangs come into sufficient proximity to each other in the presence of the target nucleic acid, and that it is only once the target nucleic acid hybridizes to the 3' and 5' overhangs that a looped conformation is formed.

As will be discussed in greater detail herein, the looped conformation may be further stabilized by the presence of a latch in the nanoswitch (i.e., an additional pair of oligonucleotides that is each partially complementary to the scaffold and to a trigger or latch nucleic acid). In some instances, the oligonucleotides that contribute to the latch are positioned upstream and downstream of the first and second oligonucleotides. In other words, one of the latch oligonucleotides is upstream of the first oligonucleotide and the other of the latch oligonucleotides is downstream of the second oligonucleotide (e.g., L1-O1-O2-L2, wherein L1 and L2 are the latch oligonucleotides that bind to the trigger or latch nucleic acid and O1 and O2 are the first and second oligonucleotides that bind to the target nucleic acid). In this arrangement, the L1 and L2 latch oligonucleotides are considered to "flank" the first and second oligonucleotides.

In some instances, the oligonucleotides that contribute to the latch are positioned between the first and second oligonucleotides. Only one latch oligonucleotide is in close proximity to the first oligonucleotide and only one latch oligonucleotide is in close proximity to the second oligonucleotide. As an example, the oligonucleotides may be arranged in this manner: O1--L1--------L2--O2, wherein L1 and L2 are the latch oligonucleotides that bind to the trigger or latch nucleic acid and O1 and O2 are the first and second oligonucleotides that bind to the target nucleic acid. In this arrangement, the first and second oligonucleotides may be considered to "flank" the L1 and L2 latch oligonucleotides.

The latch oligonucleotides typically will be located in close proximity to the first and second oligonucleotides. For example, the distance between the latch oligonucleotide L1 and the first oligonucleotide O1 may be about 0-200 nucleotides. Similarly, the distance between the second oligonucleotide O2 and the latch oligonucleotide L2 may be about 0-200 nucleotides.

If the nanoswitch is designed to bind to more than one target nucleic acid, the target-specific oligonucleotides may be arranged as follows: $O1^{T1}$-$O2^{T1}$-$O1^{T2}$-$O2^{T2}$, wherein $O1^{T1}$ and $O2^{T1}$ are the first and second oligonucleotides that are specific for target 1, and $O1^{T2}$ and $O2^{T2}$ are the first and second oligonucleotides that are specific for target 2. If latches are included for each of the targets, then the nanoswitch may comprise the following arrangement of oligonucleotides: $L1^{T1}$--$O1^{T1}$-$O2^{T1}$--$L2^{T1}$-----$L1^{T2}$--$O1^{T2}$-$O2^{T2}$--$L2^{T2}$. Alternatively, the arrangement may be as follows: $O1^{T1}$-$L1^{T1}$------$L2^{T1}$-$O2^{T1}$----------$O1^{T2}$-$L1^{T2}$--------$L2^{T2}$-$O2^{T2}$.

The disclosure contemplates that any given nanoswitch may be designed to hybridize and thus detect a plurality of nucleic acids. Thus, the nanoswitches may detect (and thus form) 1, 2, 3, 4, 5, 6, 7, 8, 9, 10, or more target nucleic acids. In some instances, each target is detected via hybridization to two oligonucleotides, and each of those oligonucleotides binds to only a single target. These oligonucleotides may be referred to herein as being target-specific.

Thus, it will be understood that the nucleic acid complexes provided herein may comprise N pairs of target-specific oligonucleotides, wherein each pair of target-specific oligonucleotides hybridizes specifically to its respective target nucleic acid. Such single complexes may then be used to detect N different targets, either simultaneously or consecutively (and randomly).

In other instances, each target is detected via hybridization to two oligonucleotides, and one or both of those oligonucleotides may bind to more than one target. These oligonucleotides may be referred to herein as target nonspecific (or promiscuous in the sense that one or both are able to bind to more than one target). Based on this disclosure, the end user will understand that a single nanoswitch can be designed to specifically detect for example two targets using for example three oligonucleotides, wherein one of the oligonucleotides may hybridize to both targets. Such nanoswitches will not bind to both targets simultaneously (as for example the afore-mentioned nanoswitches can) but they nevertheless can be used in a plurality for a multiplexed detection assay. As an illustration, such a nanoswitch may be arranged as follows: $O1^{T1/T2}$-$O2^{T1}$-$O2^{T2}$, wherein $O1^{T1/T2}$ binds to target nucleic acids 1 and 2, $O2^{T1}$ binds to target nucleic acid 1, and $O2^{T2}$ binds to target nucleic acid 2. Thus, $O1^{T1/T2}$-$O2^{T1}$ are the first and second oligonucleotides for target nucleic acid 1, and $O1^{T1/T2}$ and $O2^{T2}$ are the first and second oligonucleotides for target nucleic acid 2.

The overhangs may be of different or identical lengths, relative to each other. The overhang length may range from 5-20 nucleotides in length, without limitation. The overhangs may have a length of 5 or more, or 6 or more, or 7 or more nucleotides. One or both overhangs may have a length of 7, 8, 9, 10, 11, 12, 13, 14, 15, 16, 17, 18, 19 or 20 nucleotides. The combined length of the overhangs may vary and may depend on their sequence and the length of the target nucleic acid. Their combined length may be 14 nucleotides or longer, without limitation. In some instances, the 3' overhang and the 5' overhang are of different lengths and their combined length is at least about 22 nucleotides.

The combined length of the overhangs may be the same length as the target. Alternatively, the combined length of the overhangs may be longer or shorter than the length of the target.

The target may not bind to both overhangs to the same extent. In other words, one overhang may share more sequence complementarity with the target than the other overhang.

The overhangs will be referred to herein as the 3' and 5' overhangs intending the directionality of the overhangs. In some instances the overhangs will be ligated to each other, as described herein, and thus the 3' overhang may comprise a 3' hydroxyl and the 5' overhang may comprise a 5' phosphate.

In some instances, the overhangs may be designed such that they comprise secondary structure such as but not limited to hairpin conformations. Such secondary structures may be melted during hybridization to the target, or they may be melted as a result of a change in condition or contact with an extrinsic trigger.

Thus, also provided herein are compositions comprising any of the foregoing nucleic acid complexes. The composition may comprise a plurality of nucleic acid complexes. The nucleic acid complexes in the plurality may be identical to each other.

Alternatively, the nucleic acid complexes in the plurality may be different from each other. The nanoswitches may differ from each other with respect to their target specificity (e.g., the nucleotide sequence of their 3' overhangs and/or the sequence of the 5' overhangs). Nanoswitches may also differ from each other with respect to the distance between the 3' overhang and the 5' overhang along the length of the scaffold nucleic acid.

The compositions comprising nanoswitches may further comprise a sample such as a nucleic acid sample. The sample may or may not comprise the target nucleic acid(s). The composition may or may not comprise the target nucleic acid.

The composition may comprise a ligase enzyme.

Kits

The disclosure further provides a kit comprising a single-stranded scaffold nucleic acid, and a plurality of single-stranded oligonucleotides, each having a sequence complementary to a sequence on the scaffold nucleic acid, wherein when the oligonucleotides are hybridized to the scaffold nucleic acid no overlap exists between the oligonucleotides. In some instances, each oligonucleotide, in this first subset of oligonucleotides, has a sequence that is complementary to a contiguous sequence on the scaffold nucleic acid intending that every nucleotide in the oligonucleotide is hybridized with a nucleotide in the scaffold, and no "single-stranded bubbles" exist following hybridization.

The kit further comprises, in some instances, a subset of oligonucleotides, for example two, four, six or more oligonucleotides, that are either detector oligonucleotides such as those shown in FIG. 1A and/or are modified oligonucleotides. The subset of oligonucleotides may comprise for example a first and a second oligonucleotide that each comprise a nucleotide sequence that is complementary to a target nucleic acid. In this manner, the kit is intended to be used to detect a target nucleic acid of known or at least partially known sequence. Such target nucleic acid may be an allelic variant of genomic locus, or a cancer-specific nucleic acid such as may be found circulating in the blood of a subject having cancer, or a miRNA, without limitation. The subset of oligonucleotides may additionally comprise a third and a fourth oligonucleotide that each comprise a nucleotide sequence that is complementary to a second target nucleic acid.

The subset of oligonucleotides may additionally comprise a pair of oligonucleotides that each comprise a nucleotide sequence complementary to a trigger (or latch) nucleic acid. The trigger (or latch) nucleic acid is also included in the kit, in such instances.

In some embodiments, the kit further comprises a ligase enzyme.

Target Nucleic Acid

The target nucleic acid may be a DNA, RNA or a combination thereof. It may be a naturally occurring nucleic acid. Examples include an miRNA, a tumor-specific nucleic acid, an allelic variant, and the like, without limitation.

The target nucleic acid, as used herein, refers to the nucleic acid that is hybridized to the nanoswitch. It is to be understood that the target may derive from and thus be a fragment of a much larger nucleic acid such as for example genomic DNA or an mRNA. Thus, the target (i.e., the nucleic acid bound to the nanoswitch) may range from about 7-50 nucleotides, in some instances, while its parent nucleic acid may be much longer (for example on the order to kbs or more).

The target nucleic acid may be present and thus provided in a nucleic acid sample. The nucleic acid sample is a sample that is being tested for the presence of one or more target nucleic acids.

The sample may contain the target(s) or it may be suspected of containing the target(s). The sample may comprise non-target nucleic acid. Non-target nucleic acid, as used herein, refers to nucleic acids that are not the targets of interest. The methods provided herein allow for the detection of a target nucleic acid even if such target is present in an molar excess of non-target nucleic acid. Thus, the sample may comprise on the order of micromolar quantities of non-target nucleic acid and only nanomolar or picomolar quantities of target nucleic acid and still be able to detect the target. The target nucleic acid and non-target nucleic acid may be present in the sample at a molar ratio of $1:10^2$, $1:10^3$, $1:10^4$, $1:10^5$, $1:10^6$, $1:10^7$, $1:10^8$, or $1:10^9$. The Examples demonstrate detection of picogram quantities of target nucleic acid in the presence of about 100 μM total nucleic acids, the vast majority of which will be non-target nucleic acids.

The nucleic acid sample typically is not in vitro amplified prior to analysis using the methods described herein, meaning that it has not been subjected to amplification methods such as PCR, and the like.

The nucleic acid sample may be or may derived from a biological sample such as a bodily fluid (e.g., a blood sample, a urine sample, a sputum sample, a stool sample, a biopsy, and the like). The disclosure contemplates that such samples may be manipulated prior to contact with the nanoswitches. For example, the samples may be treated to lyse cells, degrade or remove protein components, fragment nucleic acids such as genomic DNA, and the like.

In some instances, the target nucleic acid is or is derived from or is a fragment of a miRNA, an mRNA, a genomic DNA, a non-coding RNA, and the like.

Nucleic Acid Detection Methods Using Nanoswitches

Provided herein are methods for detection of nucleic acids. Such methods may be used to diagnose a condition, and thus may be referred to herein as diagnostic methods.

In some instances, the method involves contacting any of the foregoing nanoswitches with a nucleic acid sample under conditions that allow a target nucleic acid, if present in the nucleic acid sample, to hybridize to the 3' overhang and the 5' overhang of the nucleic acid complex, and detecting the conformation of the nucleic acid complex, wherein a looped conformation indicates presence of the target nucleic acid in the nucleic acid sample. As described herein, the nucleic acid complex adopts a linear conformation in the absence of the target nucleic acid and a looped conformation in the presence of the target nucleic acid.

The conformation of the nucleic acid complex may be determined (or detected) using gel electrophoresis or liquid chromatography, or other separation technique. The gel electrophoresis may be a bufferless gel electrophoresis such as the E-Gel® Agarose Gel Electrophoresis System (Life Technologies). The method may comprise detection of the target nucleic acid and optionally detection and isolation of the target nucleic acid. The method may also comprise measuring an absolute or relative amount of target nucleic acid. This can be done for example by measuring the intensity of bands on a gel or of fractions from a liquid chromatography separation.

The conditions that allow the target nucleic acid to hybridize to the 3' overhang and the 5' overhang may be standard hybridization conditions as known in the art. Such conditions may comprise a suitable concentration of salt(s) and optionally a buffer. The condition may also comprise EDTA in order to preserve the target nucleic acid and the nucleic acid-based nanoswitch.

The hybridization may be accomplished using a constant annealing temperature. Such constant temperature may range from about 15° C. to 30° C., or 20° C. to 30° C., or may be about 25° C. The temperature may be regarded as room temperature (RT). The hybridization may be carried out over a period of hours such as 1, 2, 3, 4, 5 hours or more.

Alternatively, the hybridization may be accomplished by decreasing the temperature from a temperature at which the target and the overhangs are not hybridized to each other to a temperature at which they are hybridized to each other. This is referred to herein as a temperature ramp or a decreasing annealing temperature. The starting temperature may be about 40-60° C., without limitation. The ending temperature may be about 4-25° C., without limitation. Thus, the temperature ramp may be from about 50° C. to about 4° C. or about 40° C. to about 4° C. The Examples demonstrate a temperature ramp from about 46° C. to about 4° C. The change in temperature is typically carried out over 1-12 hours. Thus, the change in temperature may decrease by about 0.1-1° C. per minute.

Regardless of whether a constant or decreasing annealing temperature is used, the hybridization may also be carried out for much shorter periods of time, for example on the order of 10-30 minutes, provided readout can be achieved.

Thus, in some instances, if the method determines if the target is present, then the hybridization period can be short, particularly if the target is present in abundance. If the method is intended to measure the amount of target in the sample, then longer hybridization times may be required. Similarly, if the target is present in low abundance, longer hybridization times may be required, particularly if an amplifying latch mechanism is used.

As demonstrated in the Examples, the nanoswitches of the invention are exquisitely sensitive to different targets. Thus, they can be designed and used in combination to detect targets that differ only slightly including by a single nucleotide. Thus, in some instances, the nanoswitches are designed with overhangs comprising 1 or 2 mismatch nucleotides relative to a standard sequence such as a wild-type sequence (in the case of genotyping or allelic variation detection). In a similar manner, the nanoswitches can be designed to detect miRNA species that differ by only 1 or 2 nucleotides. The mismatches are optimally positioned in an internal position of the overhang rather than at either end of the overhang for sufficient discriminatory power.

Figure 1D:
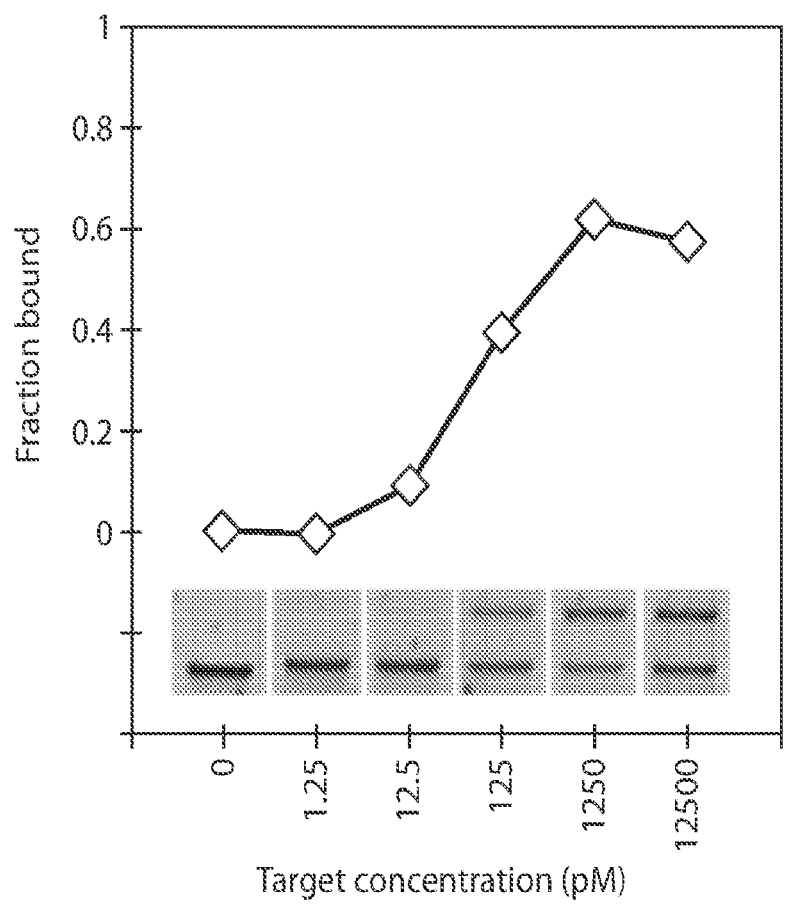
FIG. 1D. Limit of detection using nanoswitches.

FIG. 1D provides data relating to the limit of detection of nucleic acid targets. The image shows the signal of the on-state at different target DNA concentrations. The gel of the looped and unlooped nanoswitches is shown as the inset. It is possible to detect target nucleic acids at the 1 attomole level (data not shown). Thus this disclosure contemplates detecting nucleic acid targets that are present in the picomolar range, as illustrated, as well as in the attomolar range.

The nanoswitches have been demonstrated to be robust, yielding reproducible results at a variety of DNA and RNA target concentrations including but not limited to 0.25 nM up to 25 nM.

Applications
Biomarker Detection

The specificity of the nucleic acid detection assay described herein makes it a suitable for detection of biomarkers such as miRNA. Some miRNA differ from each other by only a single nucleotide. As demonstrated in the Examples, such small differences can be detected and distinguished by the nanoswitches provided herein. In a proof of principle demonstration, the nanoswitches were successfully used to detect a particular miRNA the expression of which is present in a differentiated cell population but absent in the undifferentiated counterpart. The miRNA was detectable in a total RNA population from the differentiated cells using the nanoswitches of this disclosure.

Similarly, the nanoswitches may be used to detect biomarkers that are rare or typically present in low copy number or low concentration. This is the case of circulating tumor DNA. The invention contemplates the ability to detect such DNA from a bodily sample.

As mentioned herein, the methods may detect a target that is a fragment of a larger nucleic acid. The larger nucleic acid may in fact be the art recognized "biomarker". Accordingly the methods detect the smaller targets as surrogates for the art-recognized intact biomarker.

Genotyping

The specificity of the nucleic acid detection assay described herein including its zero false positive detection makes the approach suitable for genotyping. Nanoswitches can be designed to detect various sequences that are known to have differences among individuals (e.g., allelic sequences). This can be accomplished using a single nanoswitch per allelic variant. Alternatively, this can be accomplishes using a nanoswitch that is designed to detect more than one allelic variant. Such nanoswitches are described in (Koussa et al., Nat Methods. 2015 February; 12(2):123-6). Genomic DNA may be fragmented using any number of known techniques including restriction digest, sonication, or other shearing methods. Once fragmented into smaller segments, the DNA would be mixed with one or more nanoswitches to detect multiple sequences such as the allelic variants. The presence or absence of these sequences can then be read out as the presence or absence of a band on a gel electrophoretic assay as described herein.

Nanoswitch Latches

The nanoswitches described herein may further include additional moieties useful for securing looped conformations. Such additional moieties collectively form what is referred to herein as a "latch". The latch is an additional binding interaction that occurs within the nanoswitch once, and preferably only once, a first binding interaction within the nanoswitch occurs. The latch maintains the looped conformation that is formed as a result of the first binding interaction in the nanoswitch.

A variety of different types of nanoswitch latches are contemplated, including direct and indirect latches, covalent and non-covalent latches, externally-triggered and self-triggering latches, amplifying latches, protectable latches, and reversible latches. Furthermore, these different categories of latches can be combined in various combinations (e.g. one could create an indirect, non-covalent, externally-triggered latch) for different applications. These various types of latches will be described in greater detail below.

In some instances, the latch makes the looped conformation resulting from the first binding interaction more stable. Thus the latch binding interaction can be used to hold the nanoswitch in a looped conformation when the first binding interaction is a weak binding interaction.

In some instances, the latch maintains the looped conformation throughout the entire detection method, including for example during gel electrophoresis of the nanoswitch. It is contemplated that the gel electrophoretic conditions may not be optimal for the first binding interaction, and thus that first binding interaction may be unstable during gel electrophoresis. In that instance, the presence of the latch binding interaction serves to stabilize the looped conformation throughout the gel electrophoresis regardless of whether the first binding interaction is maintained during that step. It is to be understood that the latch binding interaction may be used in a similar manner to address any instability of the first binding interaction as a result of a changed condition during the various steps of the detection methods.

These situations may arise when detecting an target (or analyte, as the terms are used interchangeably herein) that only weakly interacts with the nanoswitch and the target-specific binding partners of such nanoswitch. This may occur for a weak antibody-antigen interaction or for a short piece of DNA or RNA where only a few base pairs on the target nucleic acid interact with the nanoswitches. In these cases, there will be an equilibrium distribution of closed and open nanoswitches in solution that does not necessarily remain constant, for example as a gel is run. The gel imparts some small forces on the nanoswitches, which may make it difficult to maintain the equilibrium distribution. If the off-rate of the interaction is sufficiently fast, loops will become unlooped in the gel and will be unlikely to re-form. The result in these cases is that all or most of the nanoswitches will be in the off-state after running the gel, making detection or other measurements of weak interactions extremely difficult.

As another example, in some instances, gels may be run in a small range of conditions (e.g., temperatures, buffers, etc.), and such conditions may not be favorable for the binding interaction being measured. Therefore, it is advantageous to ensure that the state of the nanoswitches is "frozen" in the desired conditions for subsequent measurement or detection. As an example, assume there is a weak interaction that is highly stabilized by magnesium. If the gel cannot be run at sufficient magnesium concentrations to maintain the binding interaction, then even loading the nanoswitches into the gel buffer may cause the loops to dissociate. This can be prevented if the loops are latched in the native magnesium buffer and then transferred to the gel for imaging.

In some instances, the latch maintains the looped conformation even if the first binding interaction ceases. As will be discussed herein, in some instances the first interaction may be deliberately disrupted once the latch binding interaction occurs. For example, in one embodiment, the first binding interaction may detect a rare target such as a rare target nucleic acid. If the target is rare, for example it is present in a single copy, then it may only impact the conformation of a single nanoswitch. In order to optimize detection of such rare events, the invention contemplates that a latch binding interaction is used to maintain the looped conformation of a nanoswitch following the occurrence of the first binding interaction, and that thereafter the first binding interaction may be disrupted, thereby dissociating the target and allowing it to trigger sequentially first binding interactions in additional nanoswitches, each of which will in turn also employ a latch binding interaction. In this way, a single target may cause a number of nanoswitches to adopt looped conformations, and the plurality of nanoswitches, thereby increasing the likelihood that the single target will be detected. Such nanoswitches and their latch moiety therefore allow the signal from a single copy or low abundance target to be amplified by recycling the single copy or low abundance target through a number of nanoswitches. This approach may be referred to herein as "catch and release" of a target (or analyte) so that a single target can trigger multiple nanoswitches to close (or adopt the looped conformation). Since the latch by definition is stronger than the interaction of the weak target with the nanoswitch, repeated cycles of catching, latching and releasing (by heat or buffer change, for example) can result in signal amplification.

As used herein, a looped conformation may be referred to as a closed conformation. Similarly, a linear conformation may be referred to as an open conformation.

The latches provided herein include but are not limited to nucleic acid based latches, and they can be used in the detection, measurement and/or purification of a variety of targets including but not limited to target nucleic acids and target proteins or peptides.

Direct and Indirect Latching

One approach for "welding shut" nanoswitches to facilitate readout using gel electrophoresis is to directly cross-link the interacting molecules of interest to each other. "Direct latching" can be accomplished using, for example, a cross-linker such as (succinimidyl 4-(N-maleimidomethyl)cyclohexane-1-carboxylate) (SMCC) or glutaraldehyde, to cross-link, for example, and amine to a sulfhydryl group, or two amines to each other, respectively. If reactive groups desired to form a cross-link are not native to the molecules of interest, these molecules can be engineered directly to facilitate direct cross-linking.

An alternative strategy to direct cross-linking that may provide greater flexibility and modularity is an "indirect latching" approach. In this case, the molecules or molecular regions being cross-linked to each other to "weld shut" the DNA nanoswitch are not directly part of the molecules of interest, but are instead attached to the DNA nanoswitch scaffold, adjacent or near to the attachment points of the two molecules being assayed. In such a system, the molecules of interest can be exchanged or replaced with alternative molecules without having to develop a different latch system. The latch will still create a similar-sized loop as in direct latching.

In some embodiments, hybrid systems can also be created, in which one part of the molecular latch is directly connected to or a part of the molecules of interest, whereas the other part is connected to the nanoswitch scaffold.

Covalent Vs Non-Covalent Latches

Latch closure can occur through the formation of a either a covalent or non-covalent bond. Examples of non-covalent interactions that could be used to stabilize loop closure include DNA hybridization, receptor-ligand bond formation (e.g. between biotin and streptavidin), and formation of interactions between DNA and proteins. Examples of covalently cross-linked latches include glutaraldehyde latches, click chemistry latches, and sortase latches.

Ligase Latching

In one embodiment, a covalent latch is contemplated. That latch involves the covalent ligation of the two nucleic acid strands. In the case of target nucleic acid detection, the 3' overhang and the 5' overhang (which are the unhybridized regions of the "detector" strands) can be ligated to each other once bound to a target nucleic acid. Since ligase (e.g., T4 ligase) typically only repairs DNA nicks if the opposing strand is present, this scheme should covalently link the two ends of the detector strands only when the target strand is hybridized to the nanoswitch. The 3' overhang will have an intact 3' hydroxyl and the 5' overhang will have a 5' phosphate, both of which are required for certain ligases. The nanoswitch so generated will therefore incorporate a detector strand having a 5' overhang having a 5' phosphate. The ligation procedure could be carried out to "freeze" the states of the nanoswitch. Additionally or alternatively, the ligated nanoswitches could be heated to release the target nucleic acid, enabling it to react with another nanoswitch and for the cycle to be repeated, as described above in the context of an amplifying nanoswitch. The process can be repeated multiple times to increase the number of nanoswitches that read out with a looped conformation in the presence of the target nucleic acid. This allows for detection of even a single copy of the target.

For nucleic acid (e.g., DNA and RNA) detection at low levels, detector strands could be intentionally designed to be weakly interacting so that the "catch and release" activity could be easily exploited to amplify the signal from such targets. Signal amplification may occur in at least two different ways: one in which there is a linear amplification that is dictated by the number of "catch and release" cycles, and one in which the amplification is stochastic due to weakly interacting target sequences naturally binding and unbinding with the detector strands and their 3' and 5' overhangs.

In the case of linear amplification using cyclic catch and release, in one instance, the interaction would be designed to be stable at the ligation temperature (typically 4° C. to RT), but unstable at slightly elevated temperatures. In this approach, the nanoswitches hybridize the target nucleic acids at low temperature, the detector strands are ligated to each other, the temperature is increased to dissociate the target nucleic acid from the nanoswitch, and the process is repeated with another nanoswitch. The process may be repeated one or more time. It is expected that the amplification would be roughly linear with the number of cycles performed, since each target nucleic acid has a new chance to react at each cycle. This can potentially enable quantitative detection at low levels since the number of cycles can be controlled (for example, by using a thermal cycler). In the simplest embodiment, the ligase may be present in the sample throughout all of the cycles, and the temperatures would be limited to temperatures at which the ligase does not substantially degrade.

It will be apparent based on this disclosure that a similar approach can be taken even if the target is not a nucleic acid. In these instances, the target may be a protein or another moiety and the nanoswitch is designed to measure a binding interaction with that target. Such binding interaction may occur using protein based binding partners such as but not limited to antibodies, antibody fragments, binding peptides, and the like. The invention contemplates that the nanoswitch will additionally contain a latch comprising two detector strands (one having a 3' overhang and one having a 5' overhang), wherein the detector strands only come into sufficient proximity to each other and thus are able to bind a trigger nucleic acid when the first binding interaction occurs. The detector strands and their respective overhangs would be designed to be sufficiently close to the binding partners used to capture the target of interest, so that when the loop is closed (as a result of the first binding interaction) the overhangs are in close proximity. An additional nucleic acid, referred to herein as a trigger or latch nucleic acid, having complementarity to the 3' and 5' overhangs, is then allowed to hybridize to the overhangs, and the overhangs can then be ligated to each other in the presence of a ligase. This trigger or latch nucleic acid could be added at a certain desired time or could be included in the mixture with the nanoswitches. Additionally, the ligase could be added at a desired time or included with the mixture. It will be understood that the 3' overhang comprises a 3' hydroxyl and the 5' overhang comprises a 5' phosphate.

Strong Interaction Latching

In another embodiment, the loops are latched closed by using two nearby moieties that strongly interact with each other. In this case, the latching either needs to be triggered by an external reagent or kinetically trapped so that the moieties are unlikely to spontaneously react with each other unless held in close proximity for a prolonged time. One example is a nucleic acid overhang that interacts strongly with another nucleic acid overhang but only weakly with itself. For example, two interacting overhangs can each be designed to interact strongly with the other through base pairing, but to also interact weakly with itself (i.e., internally) through base pairing to form hairpins. In this case, the hairpins act as a kinetic trap to prevent spontaneous association of the two strands, but when in close proximity for a prolonged time the likelihood of the overhangs interacting together is increased due to the natural breathing of the hairpin and the insertion of the other overhang. The relative energies of the hairpins and of the binding interactions between the overhangs can be tuned by changing the number of bases involved in each type of interaction.

In order to facilitate the detection and characterization of a wide range of molecular interactions, provided herein are a collection of methods for holding DNA nanoswitches in the closed or looped state. These latches are designed to only close, when a transient interaction occurs between two molecules that are in the same locations on the scaffold as the latch components. When no transient interaction occurs, the latch is designed to not close. Currently, interactions that are not strong enough to keep DNA nanoswitches closed during gel electrophoresis are difficult to measure and detect. By developing "latch" systems capable of keeping DNA nanoswitches shut even when the primary interaction is weak, the range of molecules and molecular interactions that can be studied using DNA nanoswitches can be expanded. Uses for the latch system include, but are not limited to, detection of weak interactions between two molecules attached to the nanoswitch scaffold, detection of analytes by stabilizing a loop formed by a sandwiching assay with two detection antibodies attached to the nanoswitch, stabilizing of interactions between a members of a compound library and target molecules for drug discovery/screening and purification of molecules through a nanoswitch separation assay. These applications and the required latch designs are described in greater detail herein.

Externally Triggered Vs Self-Triggering Latches

Latch formation (e.g. cross-linking) could be triggered externally via the introduction of molecules, or via photoactivation, force application, heating, change in solution conditions, changes in the concentration or presence of ions or atoms in solution etc.

Alternatively, the latches could exist in a metastable state which could be triggered to enable latching as a result of some molecular event, for example, transient bond formation between the weak interacting molecules of interest.

Amplifying Latches

In order to amplify the detection signal, latches can be designed so that each antigen could set off multiple latches, resulting in the closure of more than one nanoswitch. This would be a natural application of the self-triggering latches, in which the transient formation of a bond between the molecule of interest and molecules on the scaffold (e.g. two antibodies that can bind the analyte simultaneously as in a sandwich assay) and trigger the formation of a latch. In such a system, the analyte could detach from the nanoswitch to trigger the formation of additional latches without compromising the closure of the initial latch. An alternative design for an amplifying latch would be to have multiple different types of latches, such as master and slave latches. In this case, binding of the analyte to a master latch would cause the release of multiple components (e.g. DNA strands) that could then trigger the closure of multiple slave latches to enable amplification of the signal. If latches were designed to be both masters and slave a chain reaction could result.

Protectable Latches

Protective groups can be used to reduce non-specific and unwanted interactions between the latch system and molecules of interest. For example, in the case of DNA latches, this can be accomplished through the use of protection strands that could hybridize to the DNA latch anchor components then be removed via strand displacement. These protection strands could either be separate molecules of DNA, or part of the original latch anchors (e.g. they could have self-complementary components).

"Deprotection" or activation of the latch system could either be performed as a separate step, or as part of a latch triggering event. Deprotection could occur via photoactivation, DNA strand displacement, DNA cleavage, chemical cleavage or any of the triggering mechanisms described herein.

Reversible Latches

Latches can be designed to be reversible, e.g. reopened using strand displacement, enzymatic cleavage, photoactivation (e.g. azobenzene can be switched between two different states by photoactivation, with one state stabilizing DNA hybridization, and the other state destabilizing DNA hybridization), photocleavage or force.

Pre-Latching

There are instances when one may wish to latch before mixing with a sample. Reversible latches could be used to hold two components close to one another while a second binding interaction occurs. For example, if two halves of an aptamer are used to bind a single analyte, the latch can be used to hold the two halves of the aptamer in close proximity, such that when the analyte, to which the aptamers bind, is present the two halves of the aptamer can bind to the analyte. One would then want to break the initial latch, and potentially form another latch to stabilize the loop while running.

Nanoswitch Latch Designs and Preliminary Data

Nanoswitch latch designs and preliminary data for the nanoswitch latches broadly described above, will be described in greater detail herein. For example, DNA latches with two separate single-stranded regions on either side that are non-covalently cross-linked in the presence of a bridge oligonucleotide are detailed. Sequences with minimal secondary structure will facilitate greater cross-linking at room temperature, and/or temperature ramps could be used to facilitate greater latching efficiency.

Indirect Latching Through Introduction of a Bifunctional Molecule

In the case of the introduction of a molecule to close the latch, the introduced molecule will be bifunctional, in that one end will react or hybridize with the latch component at a location on the DNA scaffold, while the other end will react or hybridize with the latch component at a different location on the DNA scaffold, creating a stable loop. The introduced molecules can be added at a concentration high enough so in the case of the absence of a transient interaction, both latch components attached to the DNA scaffold will bind different bifunctional introduced molecules, essentially quenching the latch so it will not close. Conversely, the introduced molecules will be added at a concentration low enough so that in the presence of a transient interaction, when one latch component binds an introduced molecule, the location concentration will be high enough so that the other latch component binds the free functional group on the same introduced molecules, closing the latch. The bifunctional introduced molecules can have two different functional groups, or two of the same functional groups. The procedure will also work with multifunctional introduced molecules, with more than two reactive or hybridization sites. In order to improve latching efficiency, multiple reactive or hybridization groups on the anchor components of the latch can be included. In this case it may be beneficial to include orthogonal reactivities on the two anchors in order to prevent self-quenching, in which a the bridge molecule binds onto two reactive groups on the same anchor.

Examples of these types of systems include designing anchor oligonucleotides with one or more amine groups, and then cross-linking using glutaraldehyde, BS(PEG)5, or another bifunctional amine reactive molecule. Other types of reactive groups that could be used include but are not limited to azides and copper-free click alkynes (i.e., DBCO), tetrazine and trans-cyclooctene-containing reagents, maleimide and thiol containing reagents, and biotin and streptavidin.

It is to be understood that in these and similar embodiments, the latch may be located at essentially the same location as the target-specific binding partner since it may itself be part of or a modification of the binding partner.

Indirect Latching Through Introduction of an Oligonucleotide

A DNA latch can be designed under the same principles of the introduced bifunctional molecule latch described herein. In some embodiments the latch components do not react with each, but instead hybridize complimentary sequences to form stable structures. A DNA hybridization latch includes 3 component oligonucleotides. Two of the oligonucleotides, which may be referred to herein as anchors or anchor components or as latch oligonucleotides, are composed of a region that is complementary to the scaffold and a region that is complimentary to half of the third component, a latch or trigger nucleic acid. The anchors or latch oligonucleotides are hybridized to the scaffold. The third component, a trigger or latch nucleic acid has two regions, each of which is complementary to the latch oligonucleotides. This trigger or latch nucleic acid is added during binding experiments to close the latch. Spacer nucleotides can also be included between the regions of the oligonucleotides to prevent steric hindrance of binding. The trigger or latch nucleic acid hybridization regions can be designed to not be complementary to any region of the scaffold to prevent extraneous binding. The region can also either be designed to be low in secondary structure, for increased hybridization speed, or can include a hairpin, in order to minimize extraneous binding. The trigger or latch nucleic acid hybridization region must be long enough for stable loop formation, but not too long to prevent long hybridization times and steric hindrance of binding. In some embodiments, the length consists of 10-15 nucleotides. In some embodiments, the trigger or latch nucleic acid is designed with high GC content (~70%) in order for strong latch formation. Gel electrophoresis can be performed at 4° C. to ensure that the DNA latch components stay shut during electrophoresis.

Indirect Latching Through a Triggering Event

Another latch design includes cross-linking of two groups on the anchor components directly when a trigger is added. These anchor components are designed to only react when the trigger is added. The trigger could be a catalyst such as a protein or metal ion, or could be heating, photoactivation, force application, or change in solution conditions. The trigger is added for a short time before either being inactivated, quenched, or removed either directly or when gel electrophoresis is performed on the nanoswitch. The reaction is limited, so only when a loop is already formed, do these anchor components react to stabilize the loop. In addition to the reactive groups, the anchor components could have short nucleotide regions that are complementary to each other to temporarily stabilize the reactive groups in close proximity to increase the reaction rate when the trigger is added. The complementary regions are designed to be short enough to not cause stable interactions in the absence of a loop being formed from additional interactions for the assayed targets of interest.

Examples of these types of latch systems include a reaction between azide and alkyne when copper(I) is added, a reaction between the N-terminal peptide GGG and LPETGG-isoacyl-Ser (SEQ ID NO: 161) or LPETGGS (SEQ ID NO: 162) C-terminal peptide when sortase is added, and short oligonucleotides containing photoactivatable crosslinkers, such as 3-cyanovinylcarbazole or psoralen.

The latches can be designed to be reversible, in order to allow for extraction of a scaffold for re-use. This can be accomplished through the use of a reversible reaction, such as a sortase reaction between GGG and LPETGGS (SEQ ID NO: 162). This can be accomplished by first utilizing a trigger or latch nucleic acid that contains one or more mismatches from the overhangs on the latch oligonucleotides, but that still binds strongly enough for loop formation, strand displacing the trigger nucleic acids using separate complementary oligonucleotides that bind more strongly than the first trigger to each trigger-binding region on the anchor, purifying the scaffold, and then using a second trigger that binds even more strongly than the short displacing nucleotides.

Reversibility of Latches

The latches can also be designed to be reversible if two or more sets of anchor components (or latch oligonucleotides) are used. The first set of anchor components will either only be complementary to scaffold for a short region, or contain one or mismatches with the scaffold. The latch designed will be stable enough for loop formation. The region of the anchors complementary to the scaffold using new anchor components that are more strongly binding to the scaffold, either through a longer binding region or containing fewer mismatches can then be stand displaced.

Kinetic Barrier Latches

Figure 20:
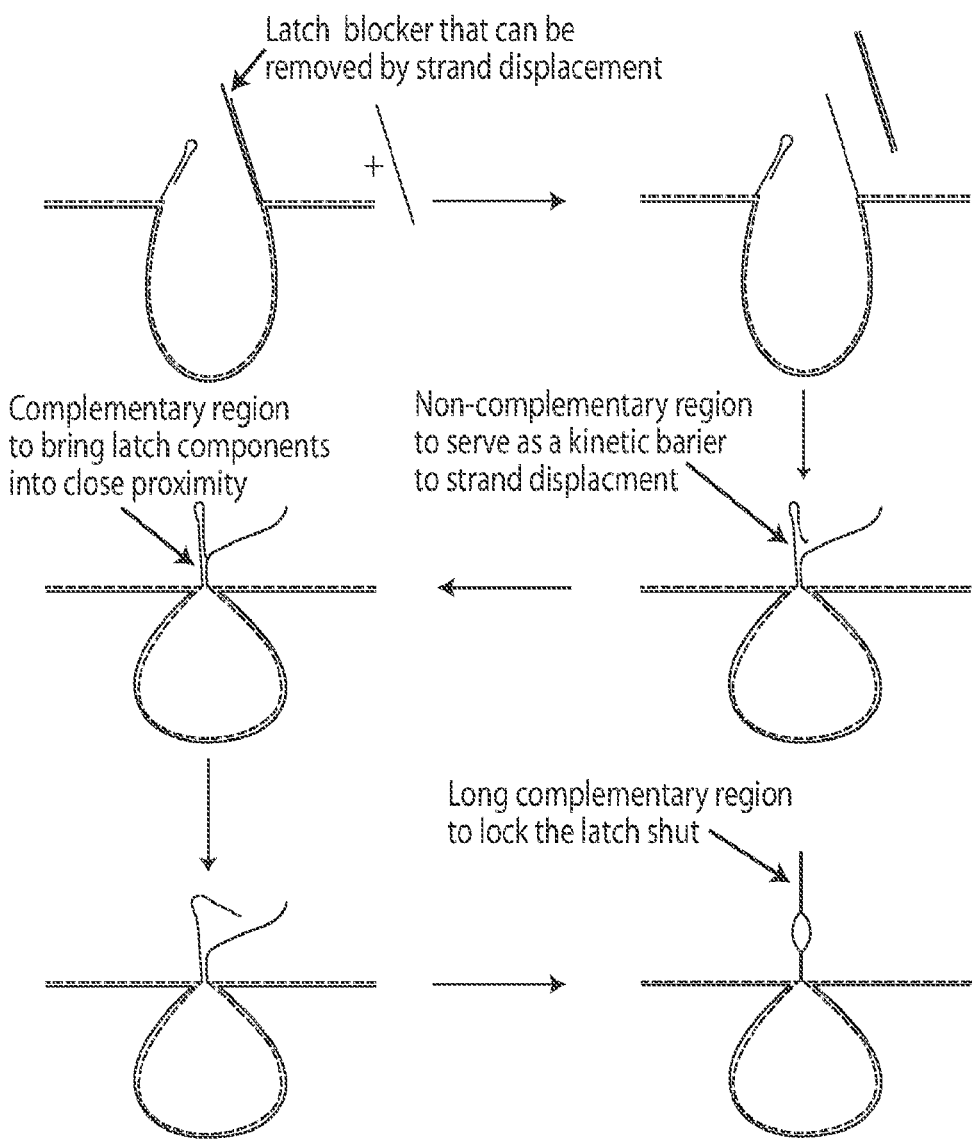
FIG. 20 shows the activity of kinetic barrier latches.

Self-triggering latches with tunable kinetics can be used to vary the rate of latching in both the open and closed states. One potential realization using DNA hybridization is illustrated herein (FIG. 20). Following removal of a protection strand via strand displacement (de-protection), the latch becomes primed to trigger when the partially complementary overhang strands are brought into close enough proximity. The sensitivity of triggering can be programmed kinetically by the introduction of a non-complementary "kinetic barrier" in order to reduce the false positive rate. After a sufficient amount of time has elapsed following "latch-activation" (which may also be regarded as deprotection), the latches can be quenched via introduction of complementary strands to stop further latch formation. Additionally, to enable reversibility (i.e. latch opening), a short toehold region could be added to the end of one of the latch strands to enable opening via strand displacement.

Purification

The nanoswitches can be used to purify targets such as but not limited to target nucleic acids or target proteins from a sample. The looped conformation nanoswitches, which are bound to such targets, can be physically separated using gel electrophoresis from linear conformation nanoswitches, which are not bound to targets. The looped conformation nanoswitches therefore may be physically separated from a complex mixture, and the targets bound thereto can be isolated from the nanoswitches.

Sequence-Specific RNA Purification. The closed and open conformations can be separated using gel electrophoresis or liquid chromatography. Specific RNA targets will only be present in the looped conformation nanoswitches, and these looped conformation nanoswitches can be isolated by gel extraction from electrophoresis or by collecting fractions in liquid chromatography. Once the looped conformation nanoswitches are isolated, the nanoswitch itself may be removed for example by digestion using a DNA digesting enzyme such as DNAse I or DNAse II, assuming the nanoswitch is made entirely of DNA. Following digestion of the DNA, the RNA can be further purified using liquid chromatography to remove the other components of the solution, or by using dialysis or other extraction kits to remove proteins and small nucleotides from RNA. Using this method, it is possible to isolate and purify a single RNA sequence from complex mixtures for various downstream applications. In instances in which the overhangs of the nanoswitch hybridize to the target only partially, then it is contemplated the nanoswitches may capture a plurality of targets, all of which will have identical sequences at their 5' and 3' ends (as a result of being hybridized and thus captured by the same overhangs) but which will differ from each other in their internal sequence between such ends.

In this way, the nanoswitch can be used to detect and purify an RNA target, which in turn can be further analyzed for its composition or biophysical properties. Downstream applications could include mass spectrometry to identify RNA modifications on the strand, or single molecule experiments to probe the structure of a folded RNA. Heretofore, the isolation of single miRNA for example has been a challenge. The nanoswitch methods provided herein facilitate miRNA isolation and analysis.

Purification of Other Targets (Analytes). Other analytes such as proteins and other biological molecules may be purified in much the same way. Thus, in some embodiments, the invention contemplates the capture and purification of proteins or other analytes of interest using the nanoswitches provided herein in combination with a latching mechanism. Targets of interest can be extracted from fluid, then isolated and/or purified from other components in a reaction mixture or sample.

This method of separation may use two target-specific binding partners and thus is more specific and more stringent than traditional purification utilizing only a single binding partner (such as a single antibody). This is because both binding partners need to bind the analyte of interest in order for loop formation and separation to occur in contrast to prior art methods that typically rely on a single binding partner for detection.

As an example, in order to purify analytes a nanoswitch with two target-specific capture antibodies and latch oligonucleotides can be used. Such a nanoswitch is described herein. The nanoswitch is contacted with a sample, binding is allowed to occur, the latch is allowed to close (e.g., by the introduction of a crosslinker or a trigger or latch nucleic acid), and the mixture is then run on a gel.

Using a latch system will increase the yield of the purification, since for purification the analyte need only stay bound to a single antibody, instead of both. The latch will keep the local concentrations high, allowing for rebinding during gel purification, in the event the analyte dissociates from only a single antibody. The analyte-nanoswitch complex can be purified from the gel using electroelution, and the analyte can be separated from the nanoswitch complex, potentially by adding another ligand to saturate the antibodies, or through a change in pH.

In still another embodiment, if the target is not a protein but the target specific binding partners are proteins, then the method may comprise a step of removing the target-specific binding partners. For example, if protein-based binding partner is used such as an antibody or an antibody fragment, the method may include a DNAse digestion to remove the nanoswitch and a protease digestion to remove the protein based binding partner. Then the target could be further purified for example by liquid chromatography, if desired.

Stabilization of Interactions for Drug Discovery/Screening.

Figure 17:
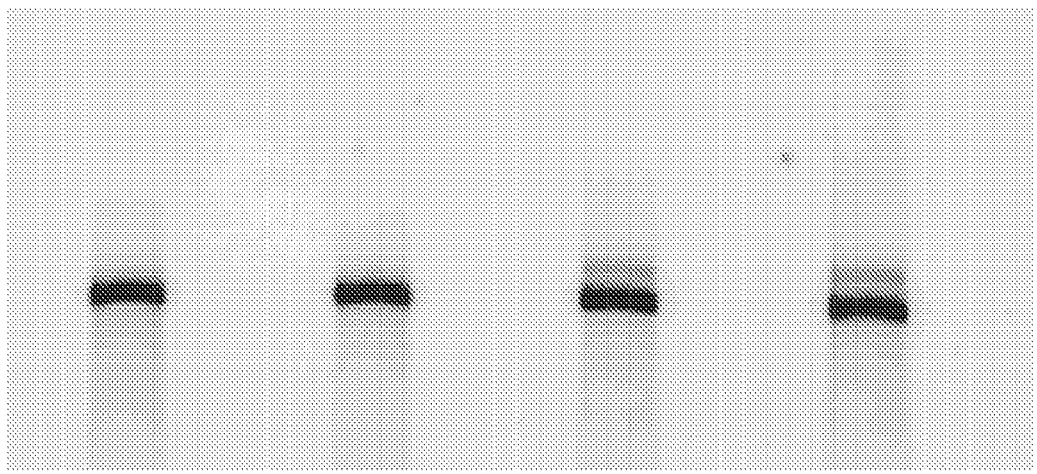
FIG. 17 shows latches used to close loops for weak aptamer binding to streptavidin.
Figure 18:
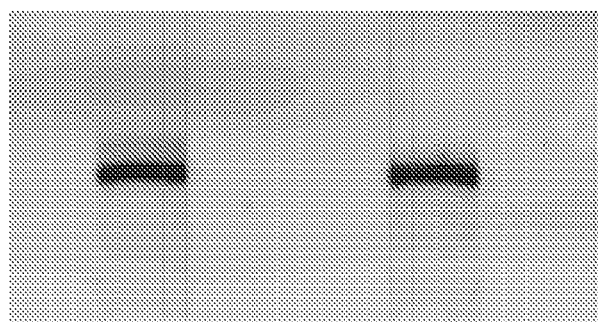
FIG. 18 shows a DNA latch used to detect weak aptamer binding.
Figure 19:
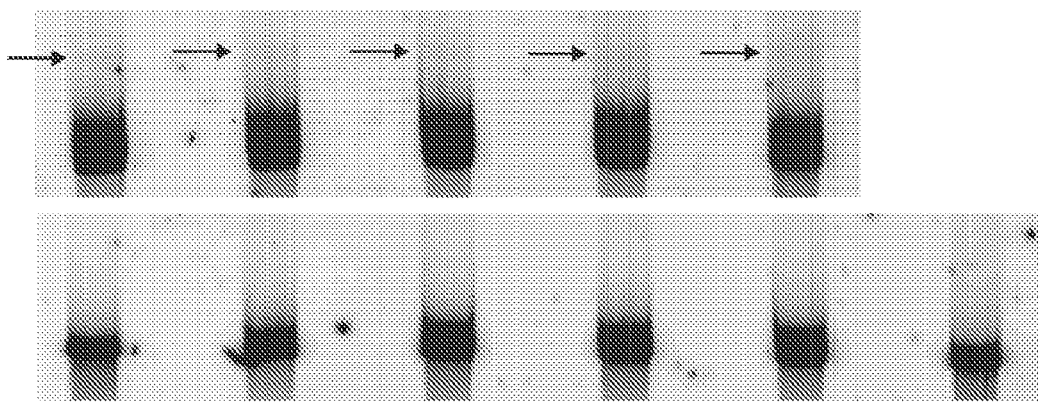
FIG. 19 shows a DNA latch used to detect weak binding between desthiobiotin and streptavidin.

In some embodiments, latches can be used to stabilize weak drug-target interactions when screening for potential drug candidates. As an example, amine-based and DNA-hybridization based latches were used to detect an aptamer binding to streptavidin, while a control sequence does not result in any signal (FIGS. 17-19). Without a latch, a band corresponding to a looped nanoswitch when either the known binding aptamer is assayed or the nonbinding control sequence is assayed is not observed.

EXAMPLES

Example 1. Fast, Background-Free Detection of Nucleic Acid Sequences Using DNA Nanoswitches Introduction The ability to synthesize arbitrary DNA sequences and the remarkable specificity of Watson-Crick base pairing has led to the recent use of DNA as a nanoscale building material.[1-2] On-demand synthesis of DNA provides programmability in design, while base pairing provides the structural "glue" as well as the ability of structures to self-assemble. These features of DNA have been exploited for the construction of two-[3] and three-dimensional lattices,[4-6] as well as for complex shapes that have been facilitated by the advent of DNA origami.[7-9] Recently, active structures such as nanodevices[10] and nanomachines[11-13] have been developed as researchers focus on applying DNA nanotechnology to solve real-world problems in science. One such application is biological sensing, where thoughtfully designed nanosensors have the potential to make detection of specific biological materials simpler, cheaper, and faster.

A two-state DNA nanoswitch for quantifying molecular interactions has been developed.[14-15] The approach is used in this disclosure to detect specific nucleic acids (e.g., DNA), an area with widespread importance in biotechnology, medicine, and forensics.[16] In medicine, for example, nucleic acids play a role as biomarkers for many diseases and their detection is crucial to the identification and diagnosis of these diseases.[17] Various electrochemical DNA sensors[18] and DNA-gold nanoparticle conjugates[19] have previously been constructed for this purpose. However, these processes involve multiple detection steps and complex designs for amplifying the output signal. The nanoswitch approach provided herein provides detection of a sequence with a simple one-pot mixture, and also gives a direct, amplification-free read out using gel electrophoresis.

Materials and Methods

Design and Oligonucleotide Mixtures:

The nanoswitch is formed using the backbone oligonucleotides (staple strands) that hybridize with the single stranded M13 scaffold to form a duplex. In addition a set of "variable" strands are designed to bind to the M13 at the prospective positions of the detector strands. The variable strands are replaced by the detector strands for forming a nanoswitch of a particular loop size. The open gaps left by the replacement of the variable with detector strands are filled using the "filler" strands.

Figures 2A, 2B:
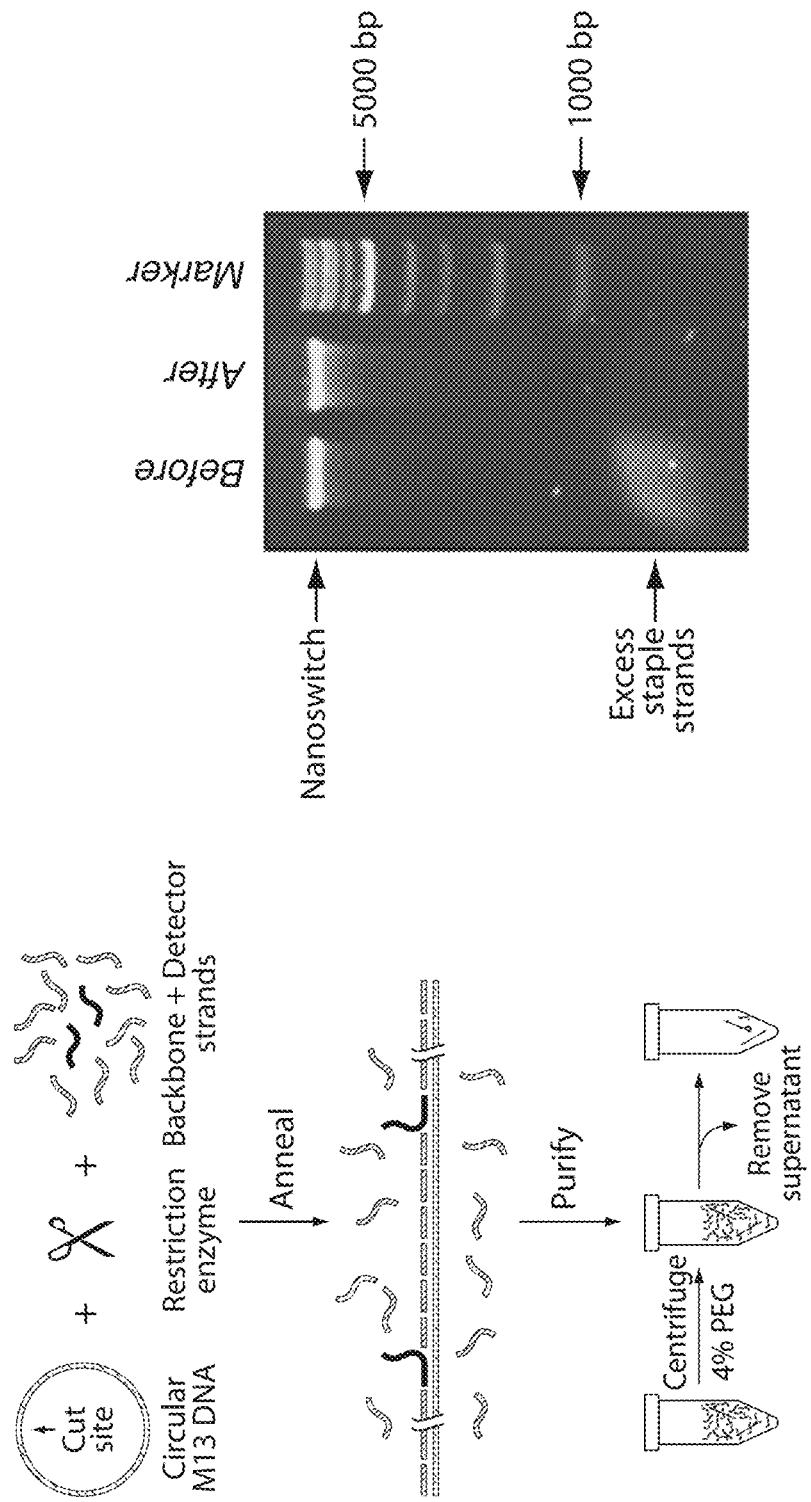
FIGS. 2A-2B show the preparation and purification of DNA nanoswitches.

Construction of Nanoswitches:

Linearization of the single-stranded M13 DNA was done as previously reported [15] and the nanoswitches were constructed using the protocol in [14]. Briefly, the linearized ssDNA was mixed with ten-fold excess of the backbone oligonucleotides, variable strands and the two sets of detector strands and filler strands. The mixture was annealed from 90° C. to 20° C. at 1° C. min$^{-1}$ in a T100™ Thermal Cycler (Bio-Rad, USA). The constructs were PEG precipitated after annealing to remove excess oligonucleotides. The PEG precipitation procedure from ref [21] was followed. Construction of the nanoswitches and purification process is detailed in FIGS. 2A-B.

Detection of Key Oligonucleotides:

The purified constructs, diluted roughly 40× from stock concentrations were mixed with desired concentration of the target oligonucleotide and annealed from 46° C. to 4° C. at 0.2° C./min in a thermal cycler and left at 4° C. overnight. Experiments were also done at constant room temperature (25° C.) where the key oligonucleotide was mixed with the nanoswitch and left at RT for at least 5 hours. For the time series experiments, addition of key oligonucleotides was done at specific time intervals in reverse. The key oligonucleotide (intended as the "target nucleic acid") was first added at 24 hours preceding gel electrophoresis and added the key oligonucleotide at other shorter time intervals up until just before loading the gel (0 min).

Gel Electrophoresis:

The nanoswitches were run in 0.8% agarose gels, cast from molecular biology grade agarose (Fisher BioReagents) dissolved in 0.5× Tris-borate EDTA (TBE) (Ultra-pure grade, Amresco). Samples were mixed with a Ficoll-based loading solution. Gels were typically run for 90 min at 75 V (constant voltage) at 4° C. and subsequently stained in 1× GelRed stain (Biotium) for 20 min. For experiments involving gel read-out times, the dye was mixed with the gel solution before the gel was cast and gels were run at 150V (constant voltage) and imaged at 10 minute intervals. Stained gels were imaged with a Bio-Rad Gel Doc XR+ gel imager. Gel bands were quantified by analyzing the scanned gel images with the gel analysis tool in the Image Lab software package available with Bio-Rad Gel Doc XR+. In some cases, constructs were spiked with a low concentration of DNA ladder (BstNI digest of pBR322 DNA, New England BioLabs) to aid in quantification (conformation 5). The highest-molecular weight band of the added ladder was used as a reference to avoid discrepancies from pipetting errors.

UV Melting Experiments:

Thermal melting profiles for the complexes were determined by measuring their UV absorbance at 260 nm with a Cary 100 Bio UV-Visible Spectrophotometer as the samples were heated at a rate of 1° C. min-1. The final concentration of the complexes was 0.5 µM. Oligos were dissolved in water and concentrations were determined by measuring the absorbance at 260 nm and applying extinction coefficients provided by the manufacturer (Integrated DNA Technologies, Inc.). Absorbance values from 2 heating cycles were averaged and the plots were fitted with the equation for analyzing thermal melting curves to determine the fraction bound [22]:

$$\theta_T = (L0_T - A_T)/(L0_T - L1_T)$$

where θ is the fraction bound, A is the absorbance, and $L0_T$ and $L1_T$ Correspond to the baseline values of the unbound and bound species, respectively. $T_m$ values were determined from these curves by finding the temperature at which the fraction bound is 0.5.

Results and Discussion

The basic principle of the DNA nanoswitch is that a conformational change is induced upon binding of a specific DNA sequence (FIG. 1A). The 'off' state of the switch is a linear duplex formed by a single-stranded scaffold (7249-nucleotide M13) and a set of short complementary "backbone oligos" that hybridize to the scaffold. Two of these strands (detectors 1 and 2) are designed to have overhangs (a on detector 1 and b on detector 2) that are complementary to parts (a* and b*) of the target DNA sequence. Recognition of specific targets is reported by a conformational change between two different states of the nanoswitch. On addition of a specific DNA sequence, target recognition and binding reconfigures the switch to form a loop thus changing it to the 'on' state. The on and off DNA nanoswitches migrate differently on an agarose gel (FIG. 1A, inset), indicating their relative quantity in the two possible states. The nanoswitch is constructed using techniques adapted from DNA origami[7] (FIGS. 2A-B), and is programmable for specific target sequences by simply integrating two new detector strands.

Figure 3A:
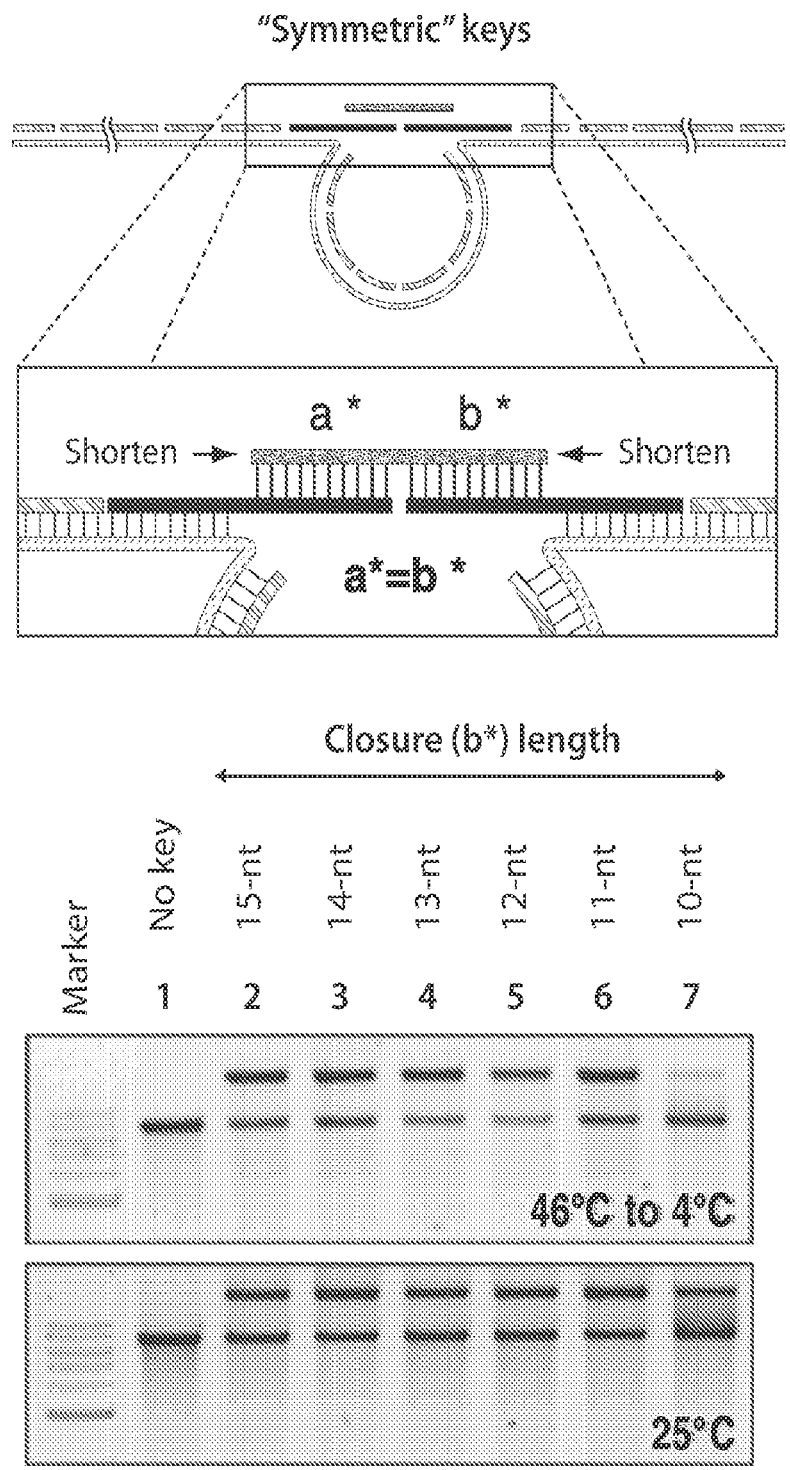
FIGS. 3A-3B show targeting strategies for the DNA nanoswitch.
Figure 3B:
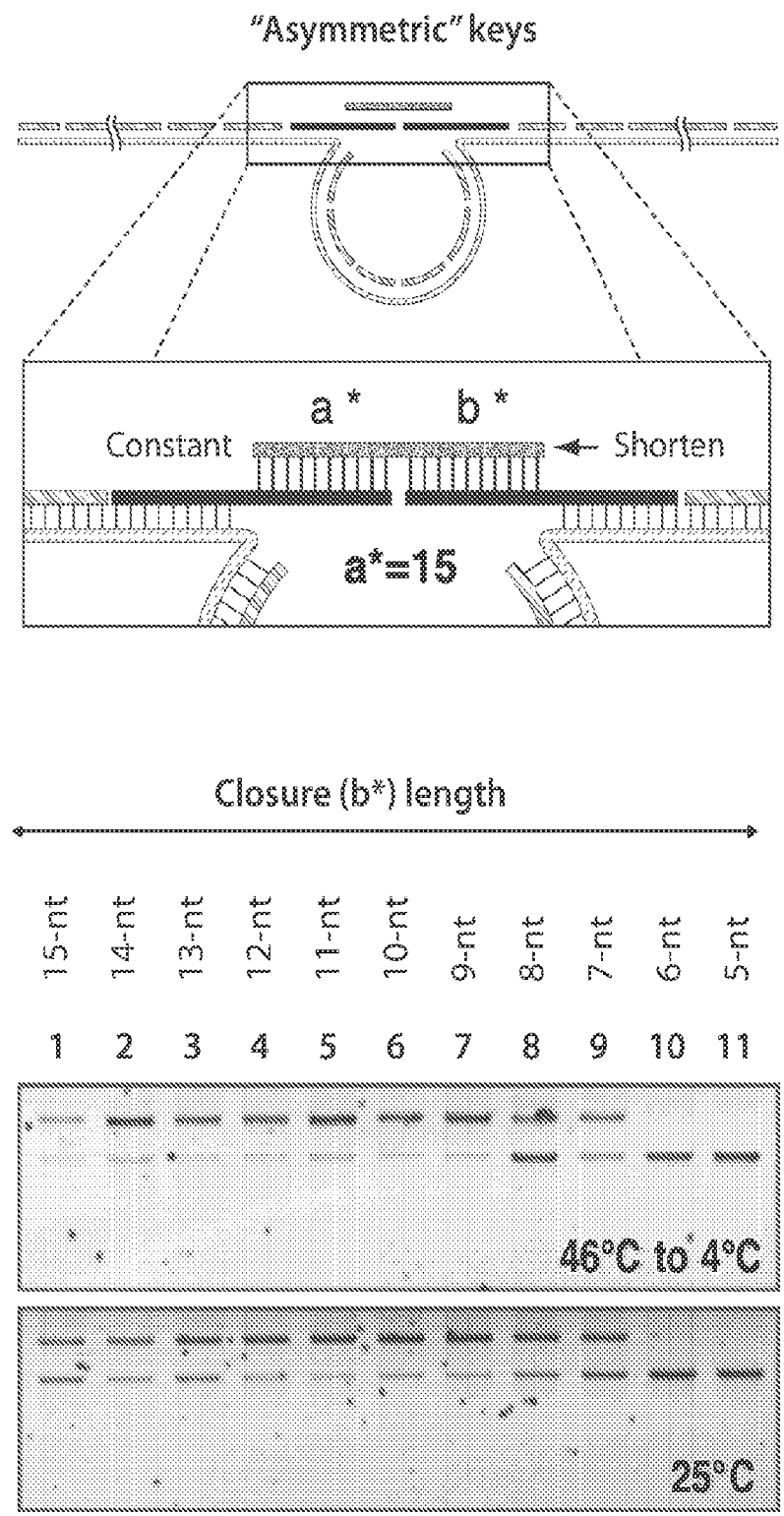
Figure 4A:
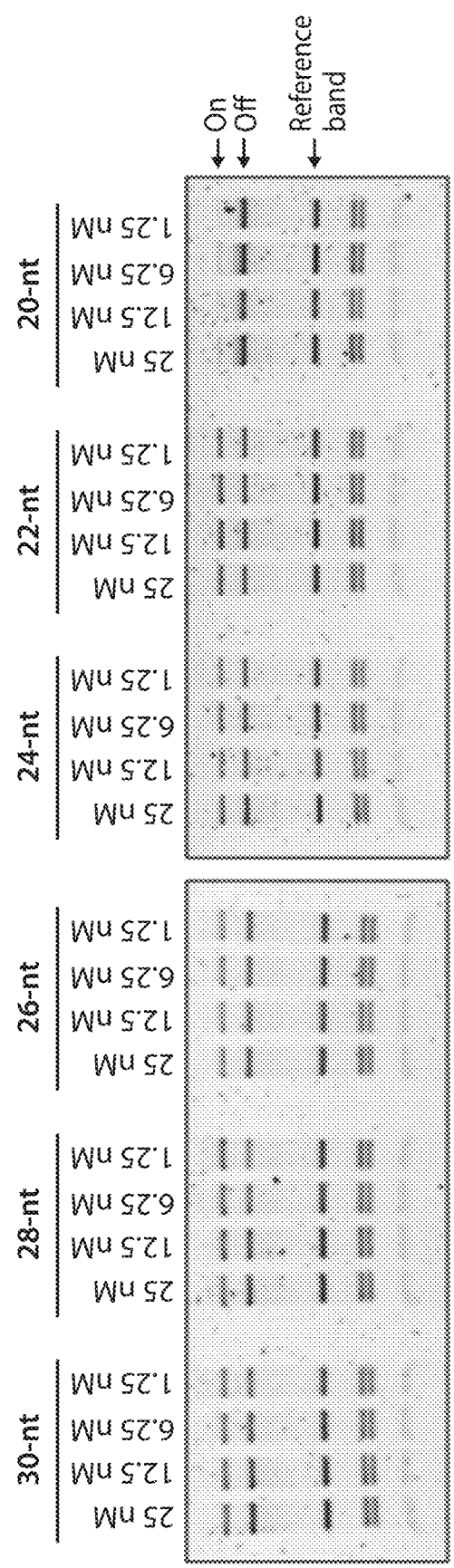
FIGS. 4A-4B show the concentration dependence of "symmetric" target binding.
Figure 4B:
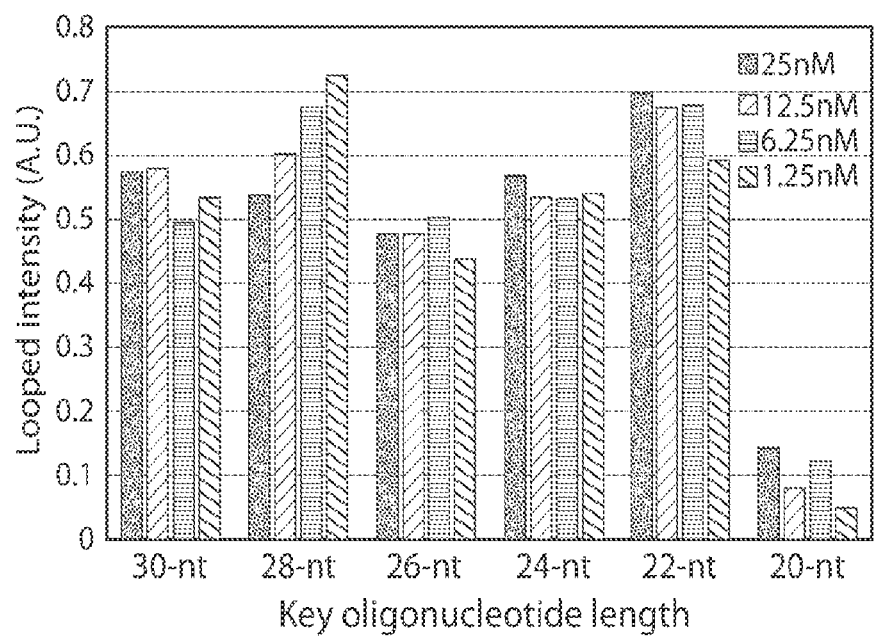

The nanoswitch detection was tested for different lengths and configurations of the target DNA sequence under different annealing protocols (FIGS. 3A-B). These experiments were performed by incubating nanoswitches in 12.5 nM of key oligonucleotide (concentrations between ~1 nM and 25 nM all had similar results, FIGS. 4A-B), and subjecting them to either a temperature ramp from 46° C. to 4° C. or holding the temperature constant at 25° C. First, "symmetric" key oligonucleotides wherein a 30-nt sequence with 15-nt on a* and b* were symmetrically truncated were tested (FIG. 3A). Detection of all key oligonucleotides under these conditions was shown, but with various efficiencies. Detection remained mostly constant until the closure length was reduced to 10-nt, at which point there was a notable decrease. The annealing tended to have the best results, except for the shortest two key oligos where the room temperature incubation had similar or better performance. Next, "asymmetric" key oligonucleotides wherein the same 30-nt sequence was truncated only on the b* side were tested (FIG. 3B). It was found that detection remained nearly constant until the closure length was reduced to 7-nt, at which point there was a notable decrease. As with the symmetric case, the annealing again produced better results for the longer oligos and worse results for the shortest ones. The differences in detection between the symmetric and asymmetric key oligos suggest that there may be an inherent benefit to designing asymmetric binding regions, likely due to the deterministic order in binding events.

Figure 4C:
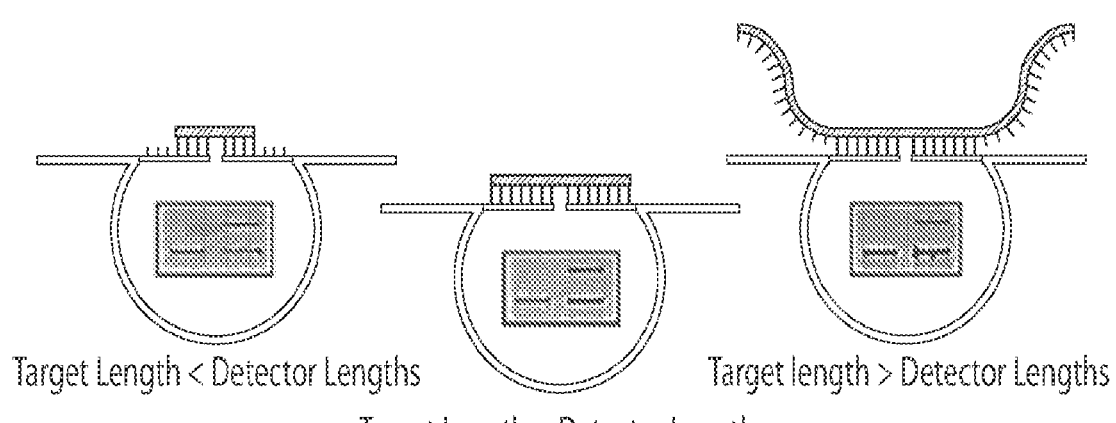
FIG. 4C provides the results of an analysis of the effect of target length versus detector length on efficacy of target capture.
Figure 5A:
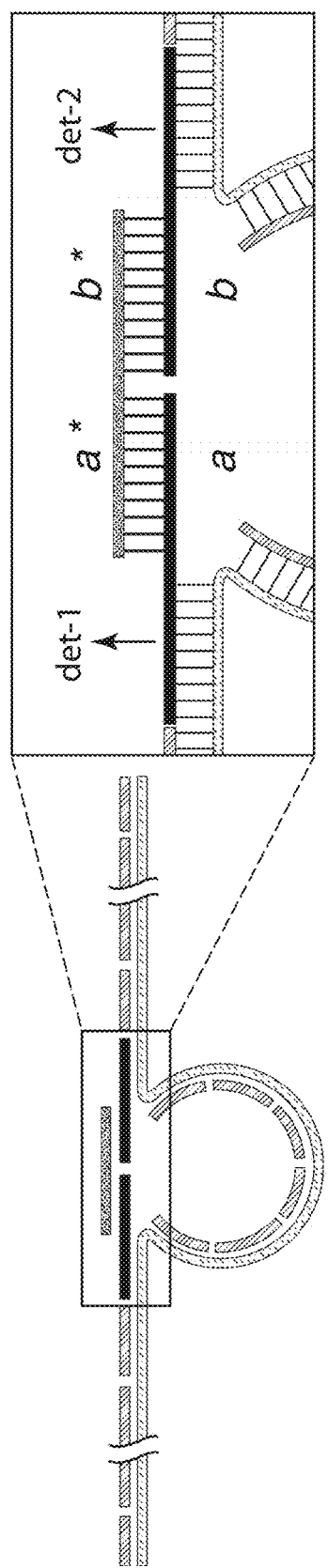
FIGS. 5A-5E show the binding efficiency of nanoswitch components.
Figure 5B:
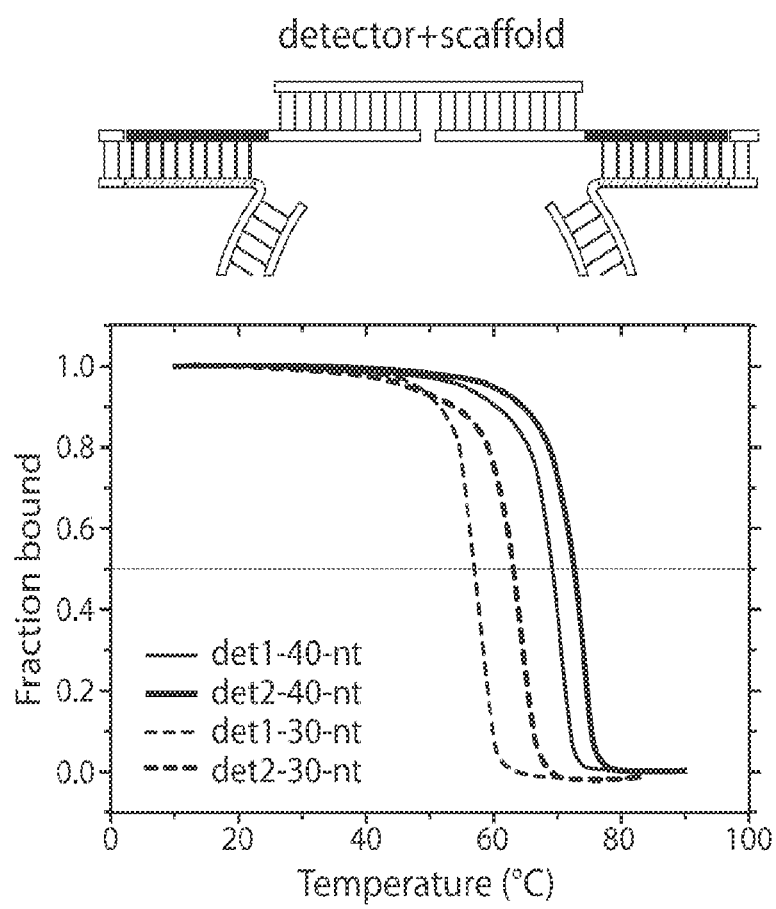
Figure 5C:
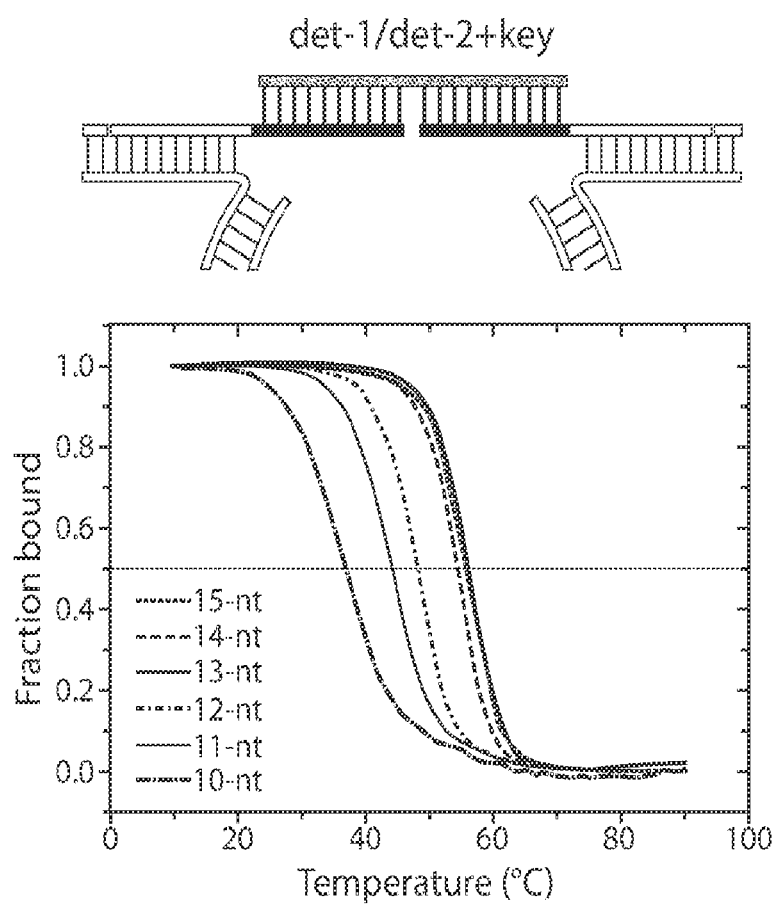
Figure 5D:
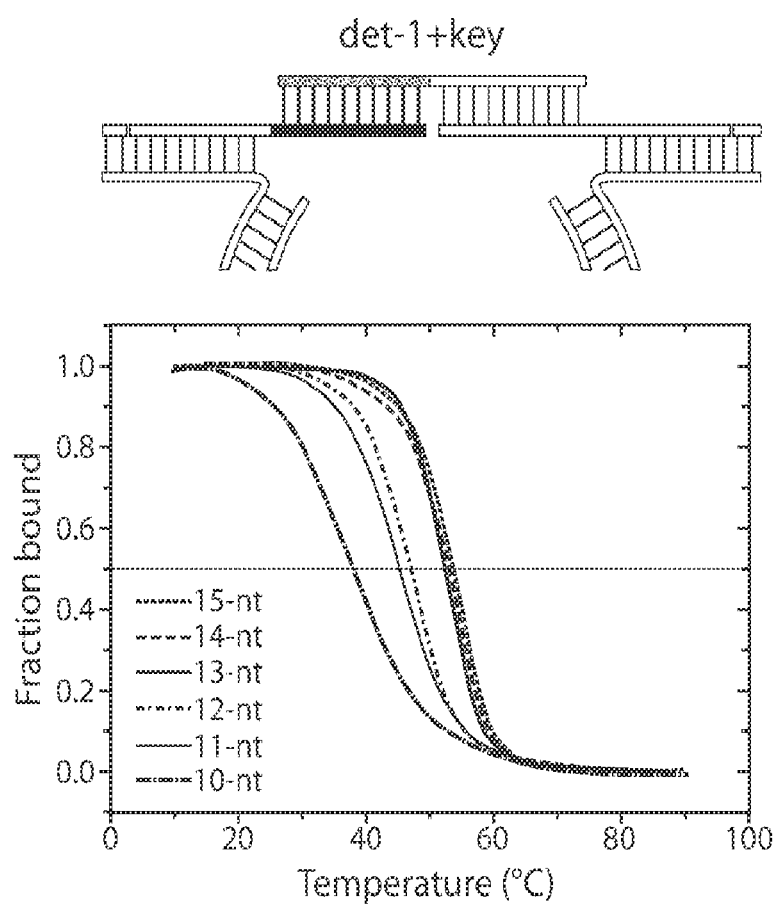
Figure 5E:
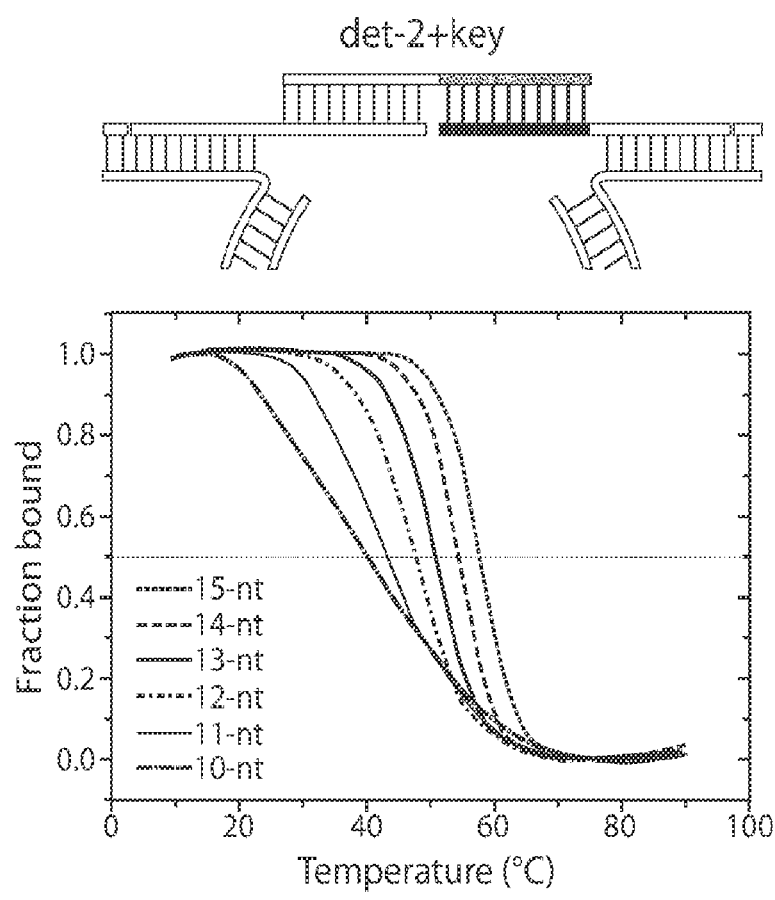

FIG. 4C illustrates the efficiency of the nanoswitches to bind targets shorter than detector lengths, targets the same length as detectors, and targets that are longer than the detectors. This illustrates that the nanoswitches are able to detect targets that are longer than the detector sequences, such targets including viral nucleic acids. Such nanoswitches may also be used to detect specific regions within longer targets such as detecting single mismatches in a longer target for mutation analysis and/or diagnostic purposes.

The drop off in detection for the shorter closure lengths likely reflects some inherent limitations imparted by the binding energies. From previous work, we estimated the effective "concentration" of two binding partners on the same nanoswitch to be ~30 nM,[15] implying that an interaction with a $K_D$ of 30 nM would be half looped and half unlooped at equilibrium. Previous measurements for the hybridization of a 7 bp DNA gave a dissociation constant in that same range (~5 nM),[20] and the dramatic drop off in detection observed here around 7 or 8 bp substantiates that detection of these short sequences are likely limited by interaction energy. It is worth noting, however, that this limitation can be potentially overcome by using a shorter loop size to increase the effective concentration of the binding partners, as long as the rigidity of the DNA at those shorter length scales does not prevent flexibility in the loop.

For both the symmetric and asymmetric key oligos, the results from the different annealing protocols suggest that secondary structure in the larger target sequences slow the recognition and binding to the nanoswitch. This results in larger targets being detected more efficiently with the high-temperature annealing, while the shorter targets are detected more efficiently with room temperature annealing. UV thermal melting analysis was performed on relevant components of the nanoswitches to better understand the effect of annealing (FIGS. 5A-E). It was found that the detector strands are well bound to the nanoswitch by 40 bp with high melting temperatures (~70° C.), while the key oligos bind to the detectors at lower temperatures (~40° C. to ~60° C.) that generally decrease as the key oligos shorten (Tables 1 and 2). The data show that the shorter targets do not fully hybridize with the detectors at elevated temperatures, and thus are effectively given less reaction time in the high-temperature annealing protocol, explaining why the shortest targets were best detected at room temperature.

TABLE 1

Melting temperatures of the symmetric key oligonucleotide/detector strand complexes

| | $T_m$ (° C.) | | |
|---|---|---|---|
| Closure length | +det-1 | +det-2 | +det-1/det-2 |
| 15-nt | 53.9 | 57.8 | 56.0 |
| 14-nt | 52.8 | 54.5 | 54.2 |
| 13-nt | 52.4 | 50.8 | 56.0 |
| 12-nt | 47.2 | 47.6 | 47.9 |
| 11-nt | 45.3 | 43.2 | 44.2 |
| 10-nt | 38.0 | 40.2 | 36.9 |

TABLE 2

Melting temperatures of the scaffold region/detector strand complexes

| | $T_m$ (° C.) |
|---|---|
| det1-40-nt + scaffold | 69.3 |
| det2-40-nt + scaffold | 72.8 |
| det1-30-nt + scaffold | 57.1 |
| det2-30-nt + scaffold | 63.3 |

Figure 6A:
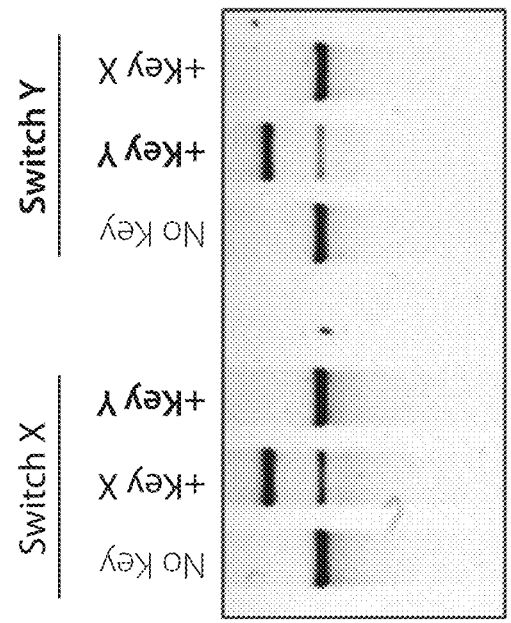
FIGS. 6A-6B show the sequence-specific detection of target oligonucleotides.
Figure 6A:
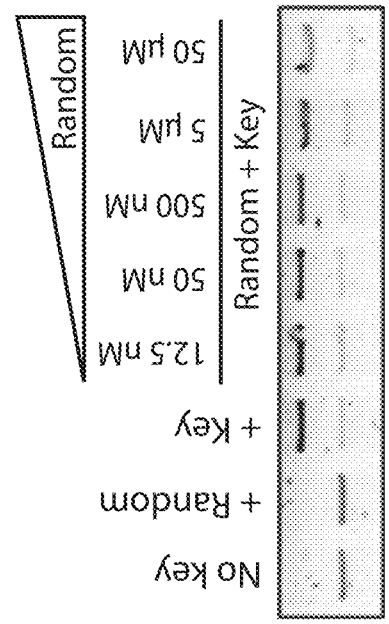
Figure 6B:
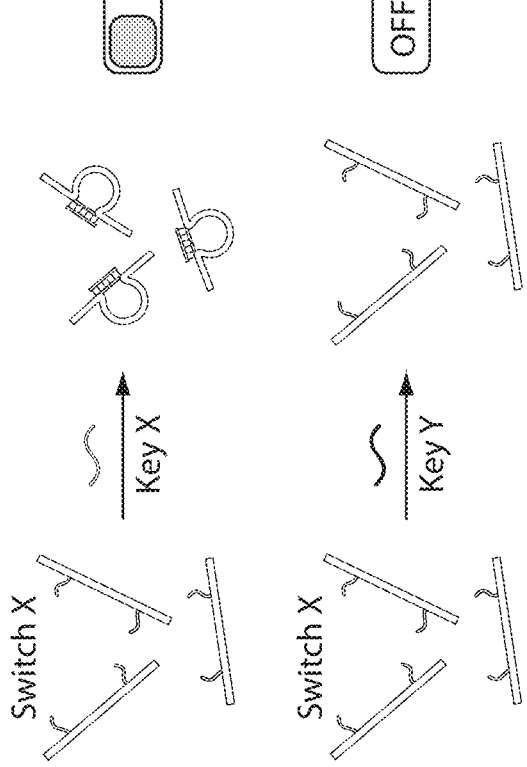
Figure 6B:
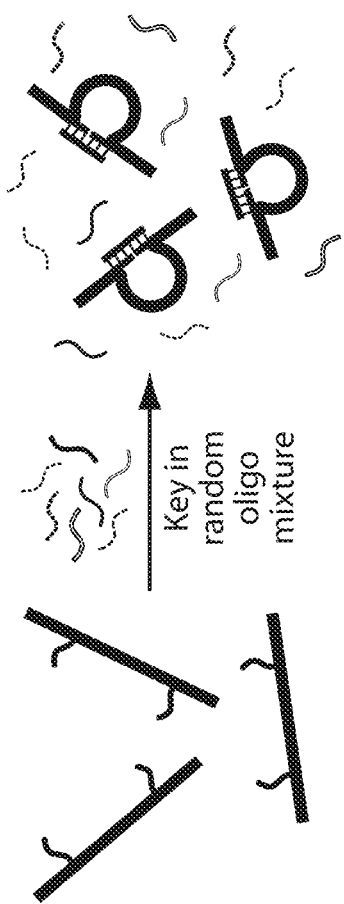
Figures 7A, 7B:
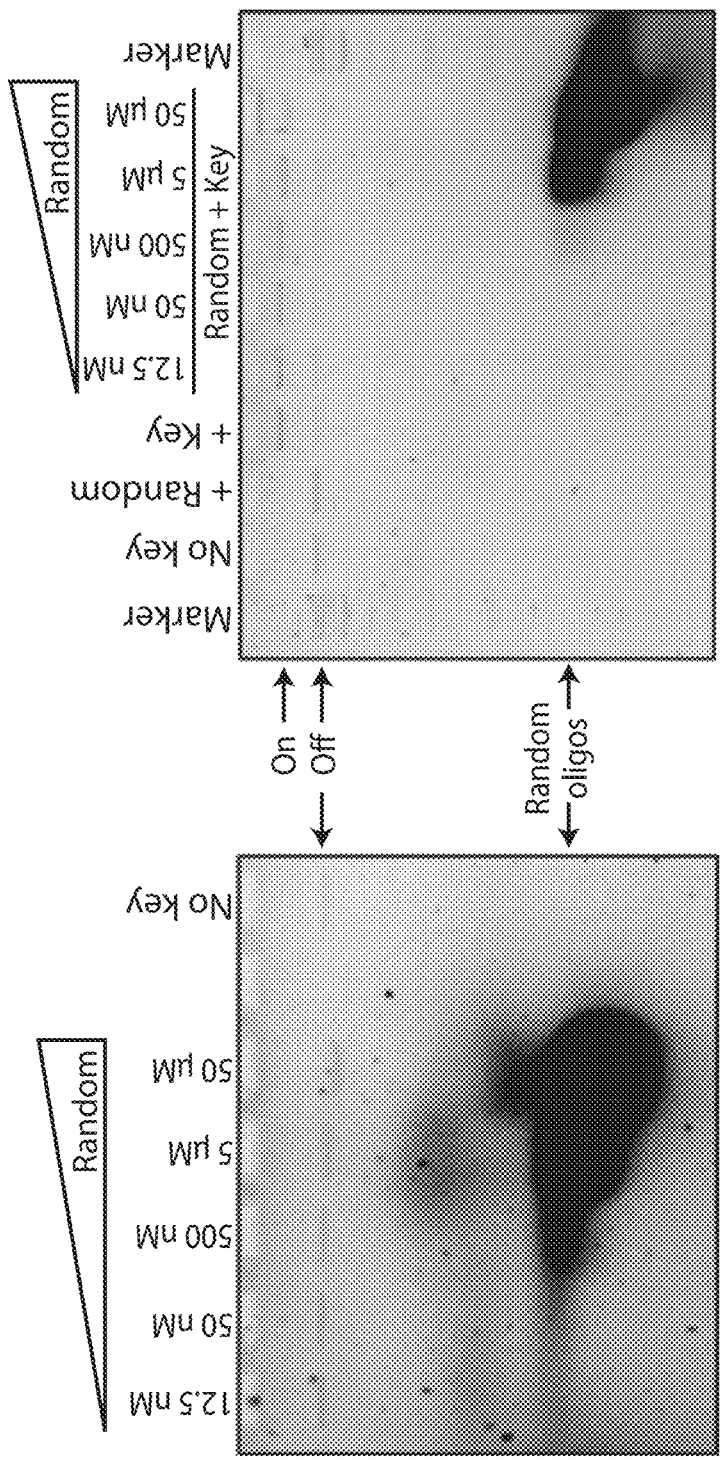
FIGS. 7A-7B shows the sequence-specific detection of target oligonucleotides.

To demonstrate the specificity of the nanoswitches, the selective activation of two nanoswitches with different key sequences, and detection of a target sequence from a large pool of random sequence oligonucleotides were demonstrated (FIGS. 6A-B). First, two nanoswitches (Switch X and Switch Y) were designed to detect two different target sequences of similar length (Key X and Key Y respectively). Sequence specific activation of the two nanoswitches was shown only in the presence of the correct key (FIG. 6A), with no false positive detection of the off-target sequences. Next, detection of a target sequence out of a large pool of oligonucleotides with the same size but random sequences was shown (FIG. 6B). Again, no false positive detection of the random oligonucleotides was found, even at concentrations as high as 100 μM (FIGS. 7A-B). Furthermore, the detection signal of the target sequence was largely unchanged by increasing the "background noise" from the random oligos in solution. This "zero background" detection is in stark contrast to many surface based capture assays, where inadvertent detection of off-target sequences can pose a significant challenge.

Figure 8A:
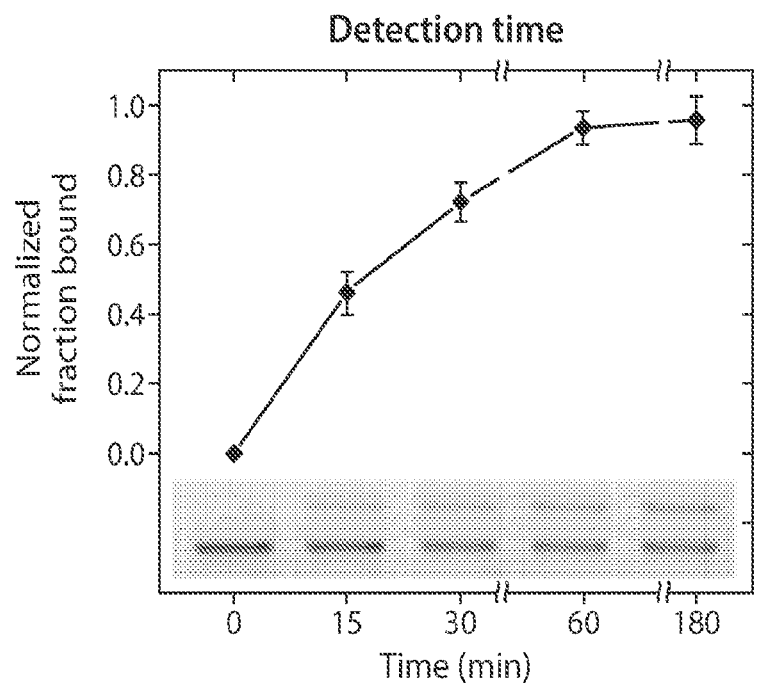
FIGS. 8A-8C show the fast detection and read-out of nucleic acid sequences.
Figure 8B:
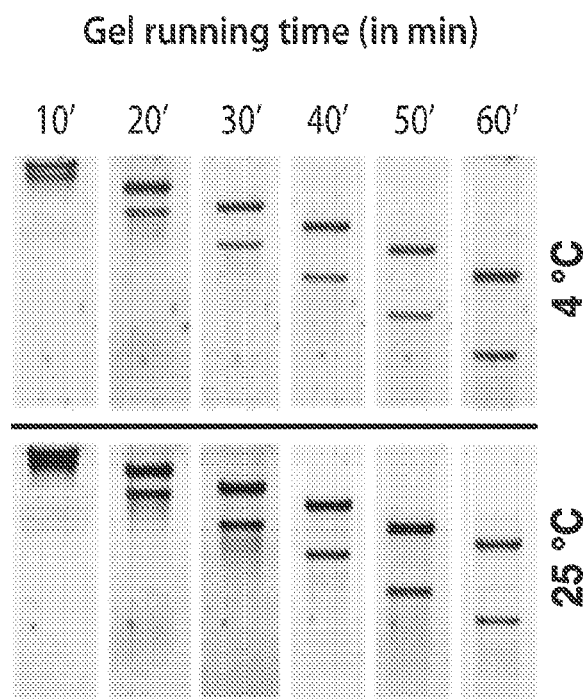
Figure 8C:
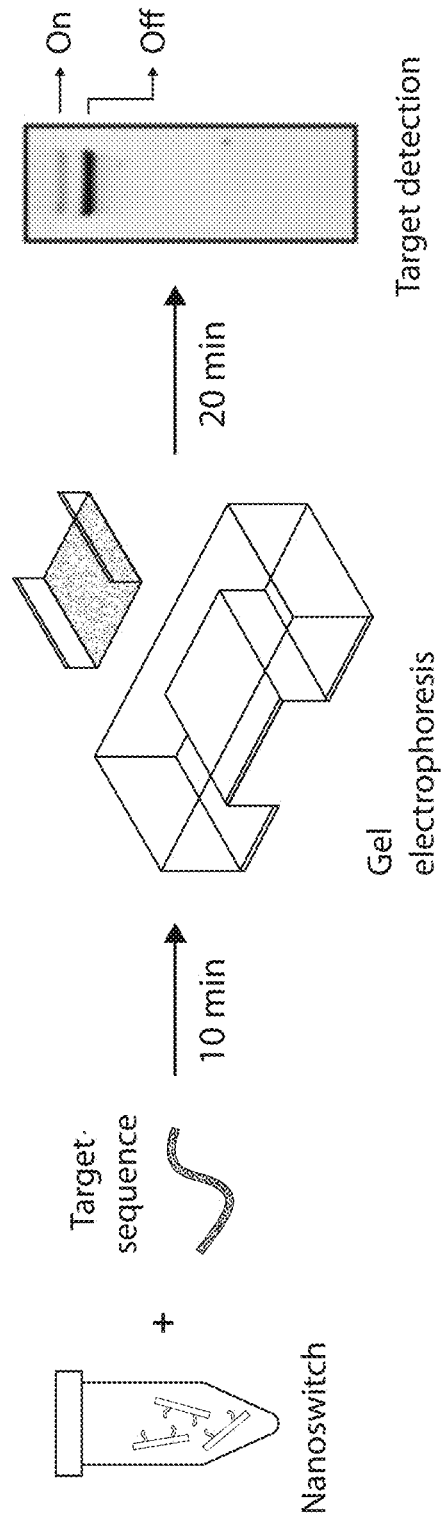

This nanoswitch assay has several important benefits including a simple one step mixture and a straightforward detection scheme. To further increase the accessibility of the technique, we characterized and reduced the time required to detect target sequences. The association rate of a key oligonucleotide onto the nanoswitch was examined, and the separation of looped and unlooped nanoswitches in the gel. Association kinetics were measured by conducting a time series at room temperature (FIG. 8A). DNA binding was detected in as little as 15 minutes, and detection was complete by 1 hour. To measure the separation time, gels were run at a higher voltage (150 V) and imaged them in 10 minute increments (FIG. 8B), finding that 10-20 minutes at 150 volts was sufficient to detect the looped nanoswitches. From these results, it was further shown that a specific DNA sequence could be detected from solution in as little as 30 minutes from start to finish (FIG. 8C). This short time for detection and the minimal requirements for the method make this a fitting approach for point of use detection, especially considering the availability of handheld bufferless gel systems (e.g. Invitrogen E-gel system).

In summary, it was shown that one can quickly and effectively detect specific DNA sequences of various lengths using DNA nanoswitches. Target sequences can be detected even from a pool of randomized oligonucleotides with no false positive detection. The DNA nanoswitches are also inexpensive, costing less than one penny in materials for the amount used in a typical gel lane in this paper. Since the scheme to use them is non-technical, requiring only common gel electrophoresis materials, the technique can easily be employed at point of use by any researcher.

Example 2. Detection of a Single Mismatch

Detection of a single mismatch requires "tuning" of the detector strands to ensure that the interruption of normal base pairing produces a dramatic change in signal. The placement of the mismatch to be detected was studied in this Example.

Figure 9A:
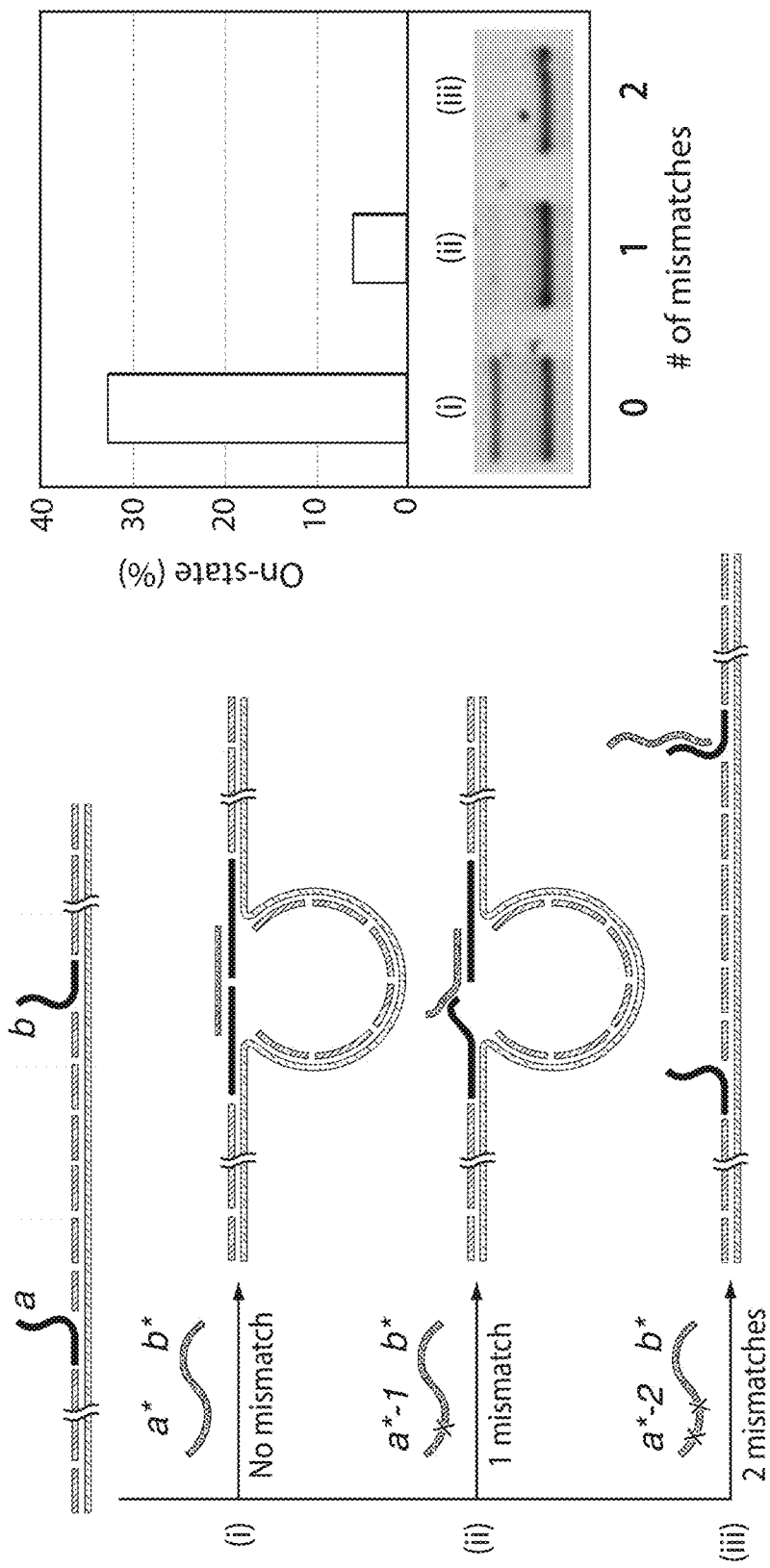
FIG. 9A shows a schematic of the detection of different numbers of mismatches (left panel) and the on-state percentage as a function of the number of mismatches (right panel).

For example, a 22-nt target sequence with complete base complementarity to the detectors inducing a conformational change which can be read out using gel electrophoresis (FIG. 9A, denoted (i)). When a single mismatch is introduced in the center of one of the detector regions, the signal drops to only about 5% (FIG. 9A, denoted (ii)). In the presence of two mismatches, there is no observable signal (FIG. 9A, denoted (iii)).

Figure 9B:
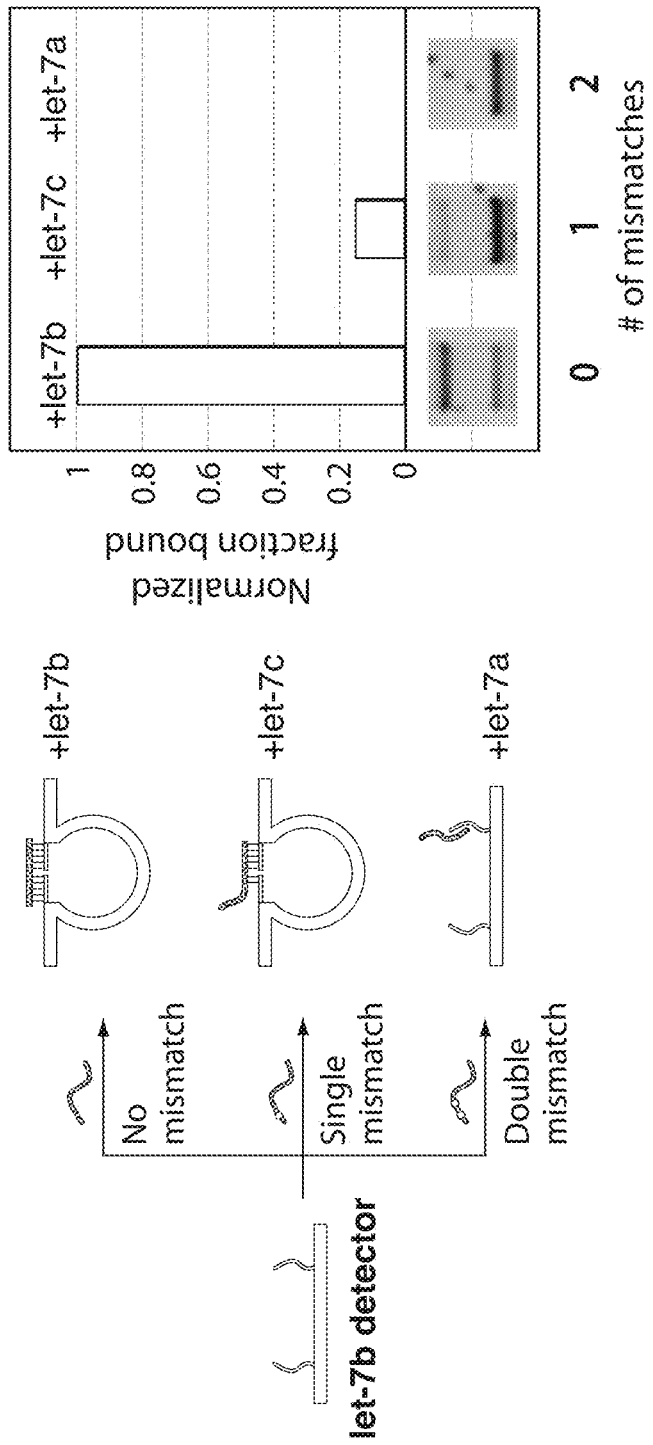
FIG. 9B shows an analysis of mismatch detection in synthetic RNA.
Figure 9C:
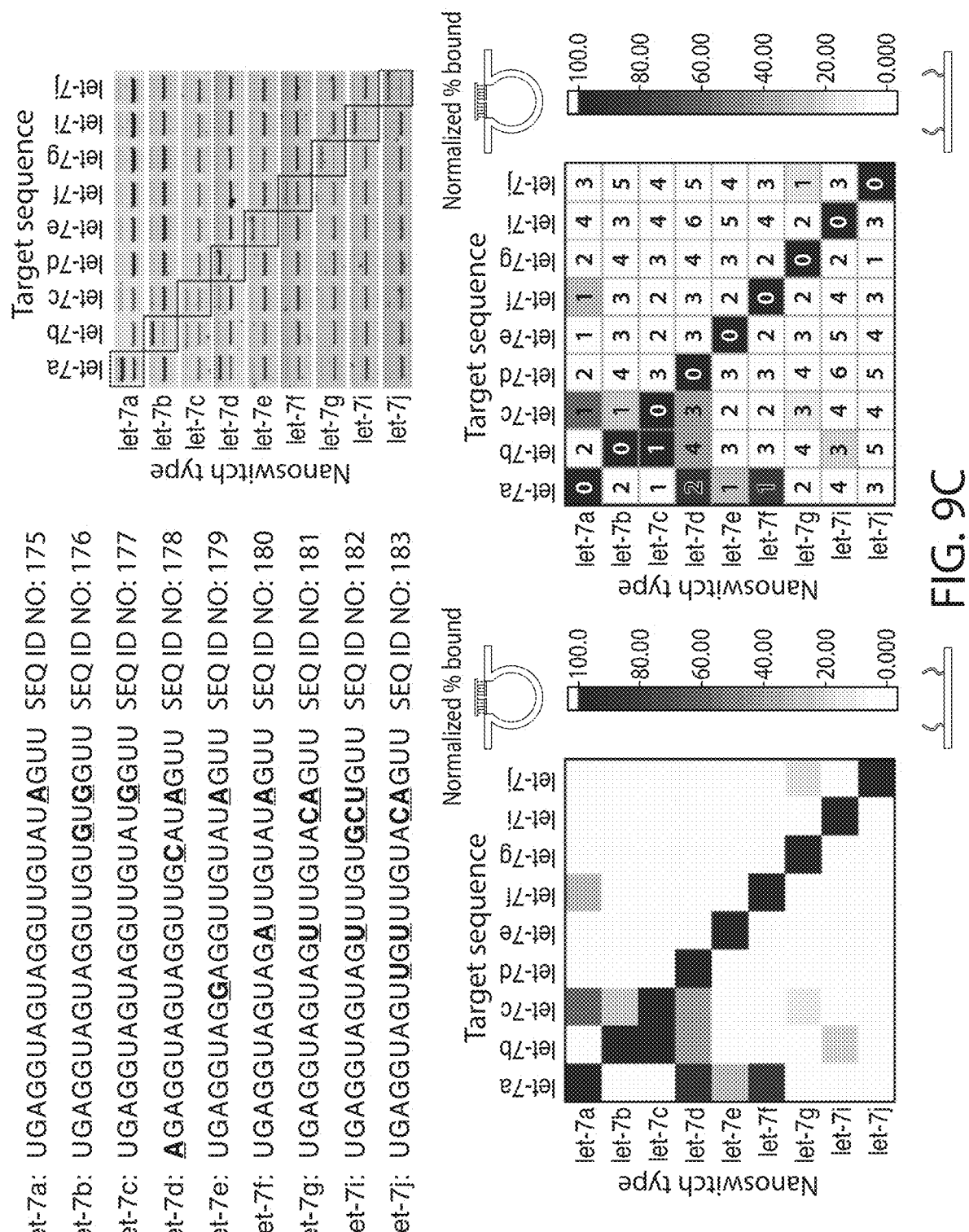
FIG. 9C shows a further analysis of mismatch detection in a complete let-7 series of miRNA sequences.

FIG. 9B provides further analysis of mismatch detection in synthetic RNA. In these experiments, the nucleic acids were members of the let-7 series of miRNA that differ by one or two nucleotides, as shown. The Figure illustrates both schematics and gel results of detection using a switch designed for let-7b. The signal drops to ~15% for a single mismatch and there is no detection for a double mismatch. This evidences the high degree of specificity that can be achieved using the nanoswitches provided herein. FIG. 9C provides further mismatch detection in a complete let-7 series of miRNA sequences. The sequences of the let-7 family of miRNA are provided. As apparent in the color version of the Figure, there are 1-4 mismatches between different members of the set. Most of the mismatch at one end, although a few occur in the middle and another occurs at the opposite end (see for example let-7d). Gel results of detection of specific let-7 miRNA compared to other let-7 miRNA sequences. Boxed diagonal shows detection of correct targets. A heat map is also provided that shows the intensities of the on-state for different switches versus targets. The heat map is then repeated but with the number of mismatches for each target versus switch shown for each. The data show that the position of a mismatch along the length of a target may have different effect, and may influence the ability of the nanoswitch to detect such target and distinguish it from other related targets. The ability to detect any given sequence using a set of nanoswitches that probe along the length of a sequence addresses this issue and ensures that mismatched sequences will be detected regardless of the position of the mismatch.

Figure 10:
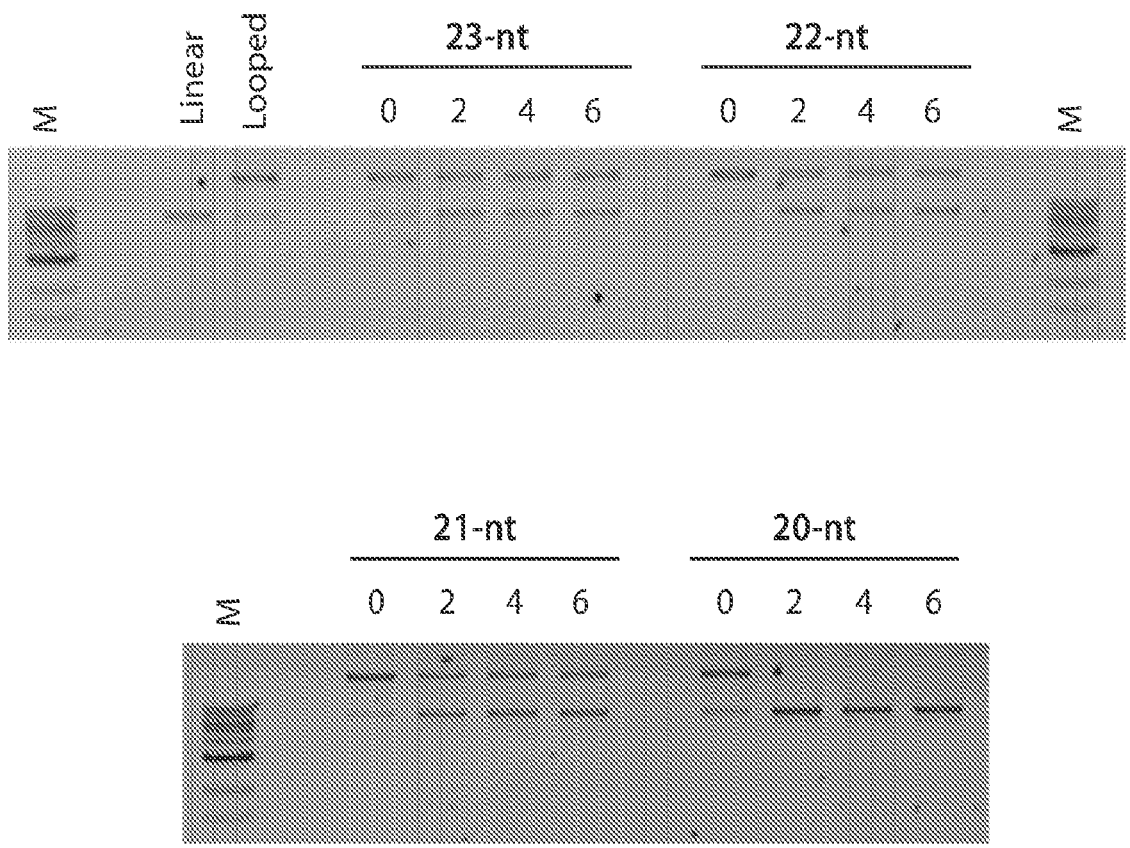
FIG. 10 shows mismatch sliders; the mismatch position 2 nucleotides away from either end of the detectors with 20 base pairs (out of 23) is effectively detected using the nanoswitch

In the case of a pair of microRNA that differ by a single base (e.g., miR 10A and 10B), the position of the mismatch plays an important role. In this specific case, the single mismatch is in the center of the target sequence and thus detection is not effective. To bypass this, target sequences were designed that are "offset" in their binding to the detectors, i.e. (1) The target has more complementarity to detector 1 than detector 2 and (2) not all nucleotides of the target have to bind to the detector. The mismatch position 2 nucleotides away from either end of the detectors with 20 base pairs (out of 23) is effectively detected using the nanoswitch (FIG. 10).

Figure 11A:
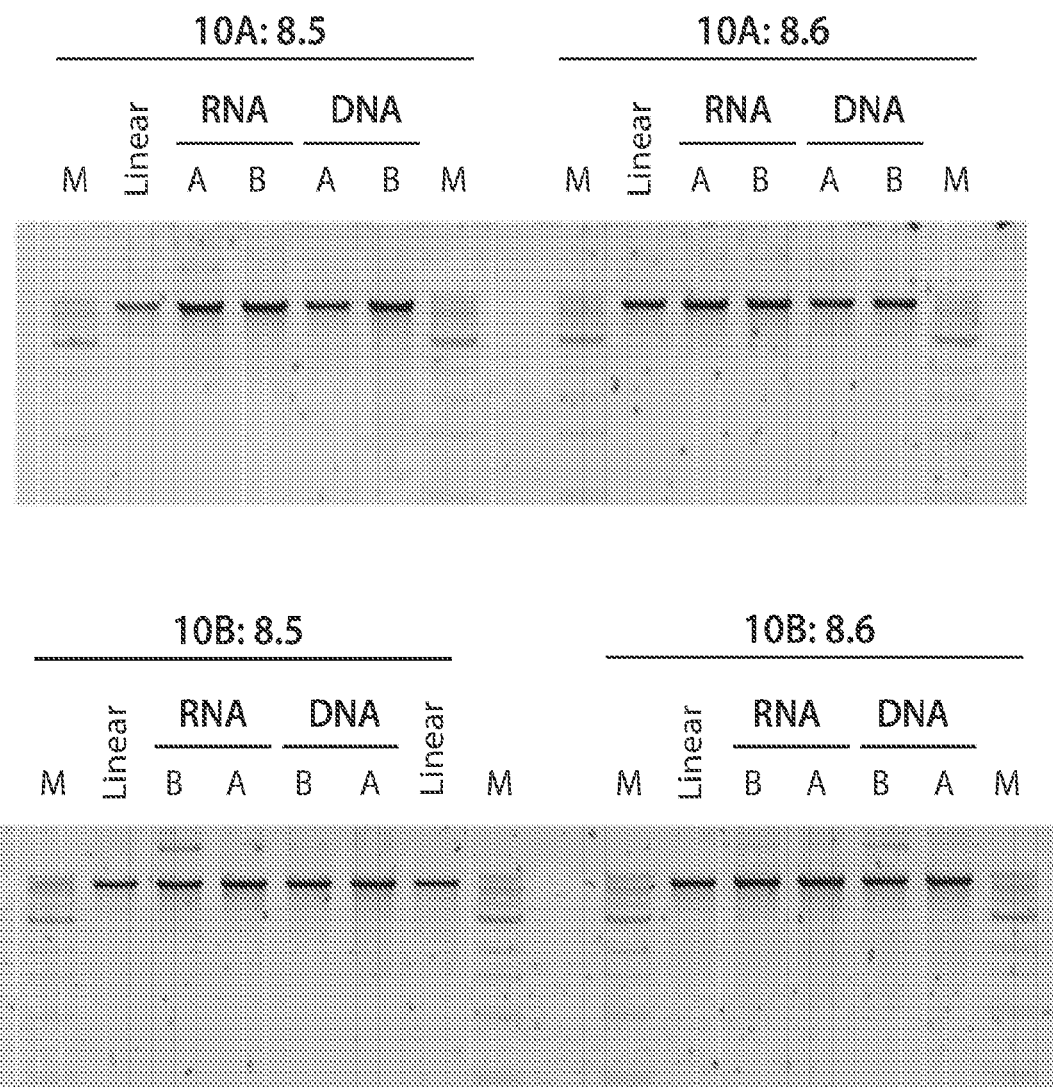
FIG. 11A shows mismatch detectors designed to bind 17 (left 5 lanes) or 18 (right 5 lanes) of the target sequence to detect single nucleotide mismatches with zero background.

The detectors for mismatch detection can be designed based on these results. For the specific case of mir10A and 10B, detectors can be designed to bind 17 (FIG. 11A left 5 lanes) or 18 nucleotides (FIG. 11A right 5 lanes) of the target sequence. This strategy works for detecting single nucleotide mismatches with zero background.

Figure 11B:
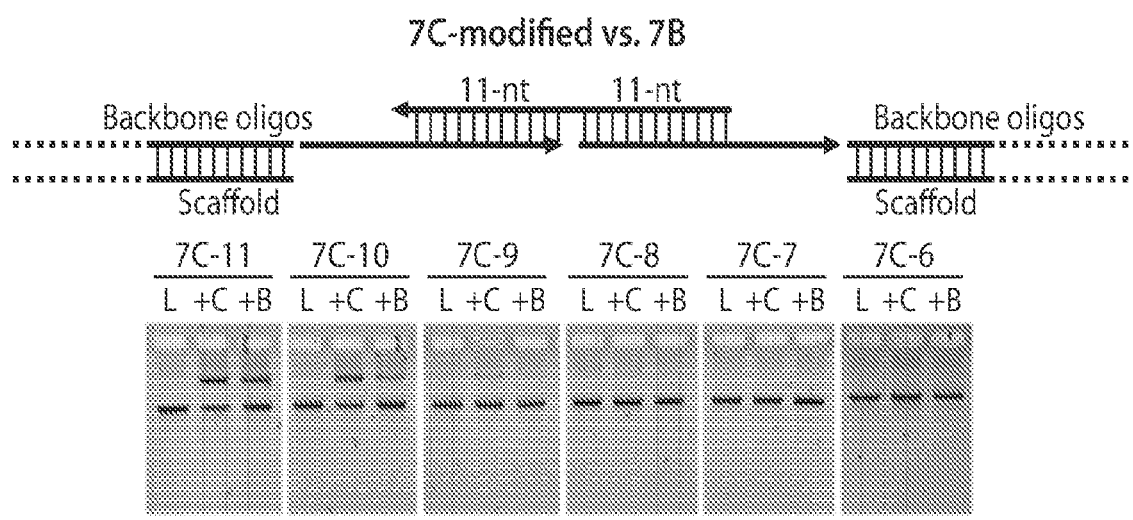
FIG. 11B shows results of an optimization for mismatch selectivity. The detector sequence is denoted 7C-11, 7C-10, 7C-9, 7C-8, 7C-7 and 7C-6 indicating the length of the "half-detector" sequence. The target is denoted as +C for let-7c and +B for let-7b. The switches are designed to be complementary to let-7c. L is a control containing no target.

FIG. 11B provides further data relating to the optimization for mismatch selectivity. In this experiment, switches were designed for let-7c miRNA but with different detector lengths (e.g., lengths ranging from 6-11 nucleotides). The gel images show detection of proper target (let-7c, denoted "+C") versus a target with a single mismatch (let-7b, denoted "_B"). At detector lengths of 10 and 11 nucleotides (half detector lengths), more bound switches (top band) are apparent for let-7c than for let-7b as the target, as compared to unbound switch (bottom band). At a detector length of 10 nucleotides, the switch is more selective for let-7c than for let-7b, as evidenced by a stronger bound switch band for let-7c than for let-7b, as compared to the unbound band for each). When the detector length is decreased to 9 nucleotides, the bound switch for the let-7c is still apparent while there is virtually no bound switch for let-7b, suggesting that switches can be designed that are highly selective for particular targets (even targets that differ from each other by 1 mismatch, although the sensitivity of such switches may be reduced in the process.

Example 3. Detection/Measurement of DNA Triplex Formation

Figure 12:
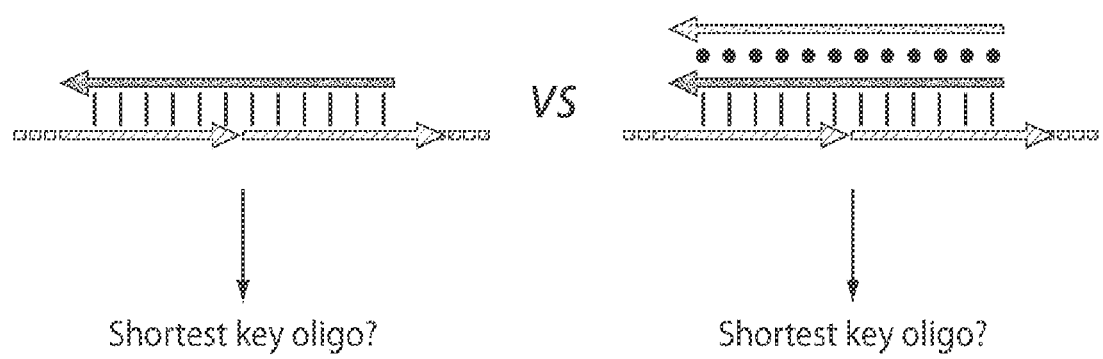
FIG. 12 is a schematic showing the use of detectors to study triple helix formation.

The efficiency of target binding to detectors can be manipulated to study triple helix formation (FIG. 12). The shortest (i.e. weakest) target threshold can be modified to be a triplex binding site (target: polypurine, detectors: polypyrimidine). Under "normal" conditions, the nanoswitch does not undergo a conformational change due to the weak binding ability of the target. However, when a triplex forming oligonucleotide (polypyrimidine) is added, formation of a triplex helix in the target binding regions results in loop closure and a target binding signal. This strategy can be used to study the on- and off-rates of triplex formation and also to increase the binding efficiency of short DNA fragments to the detectors.

Example 4. Simultaneous Detection of Multiple Sequences

The design of the DNA nanoswitch provides for customized loop sizes and different "on-states" as desired. The nanoswitch can be designed to contain two sets of detectors (or more if needed) that can bind to two different target sequences. The binding occurrence of the two targets are designed to result in different loop sizes so that each target has its own output signal (FIG. 13A). This design strategy allows for the creation of multiplexed detection of target sequences. For example, binding of target 1 will cause the formation of a 2-unit loop and binding of target 2 will form a 3-unit loop, both of which migrate differently on a gel. In the presence of both targets, both the loops will be formed and will have a distinct gel mobility of its own (FIG. 13B). This strategy works at RT without the need to anneal the target on to the nanoswitch, thus making it more useful for targets that might be sensitive to heat.

Example 5. Detection of Sequences with Significant Secondary Structure

Figure 14:
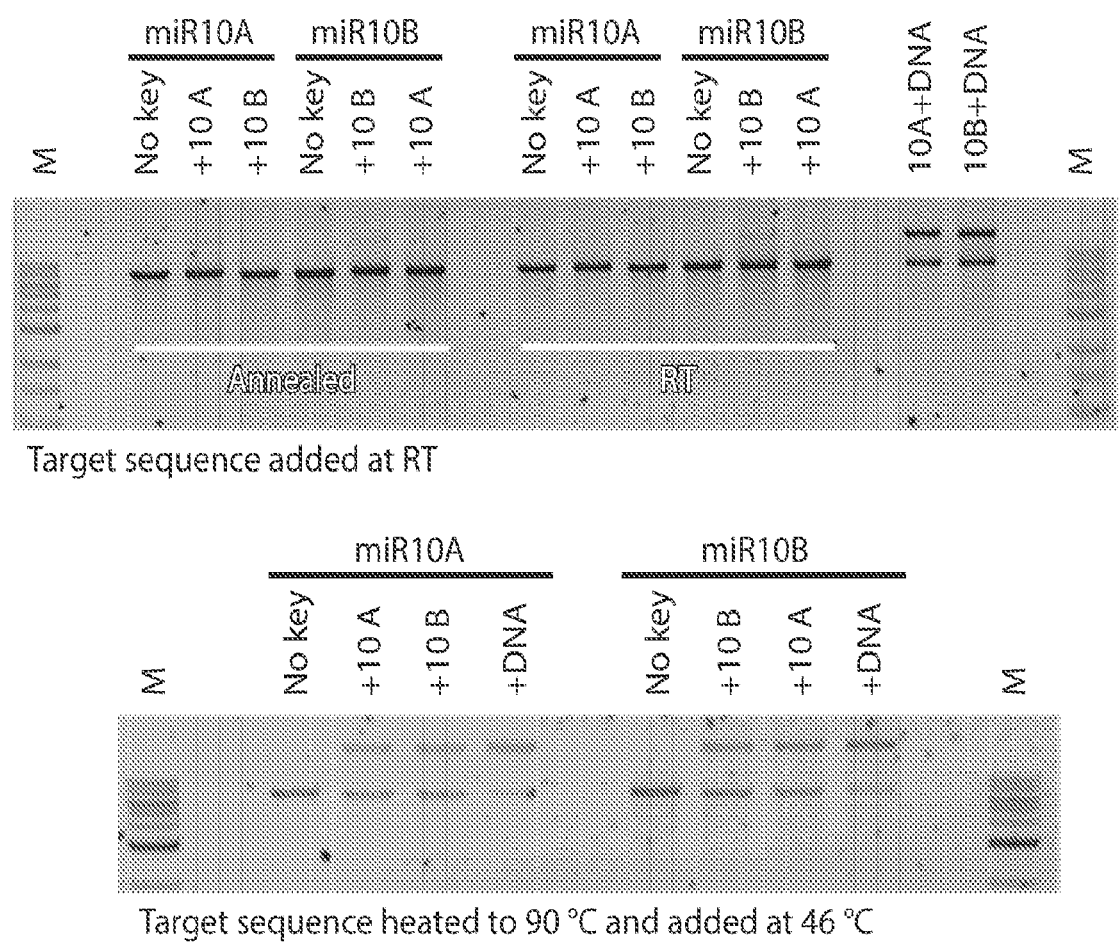
FIG. 14 shows the detection of sequences with significant secondary structure.

Long sequences of DNA and even short sequences of RNA can have significant secondary structure that can impede binding to the nanoswitch detectors. To overcome this, it is typically necessary to either heat the sample before mixing with the nanoswitch or to use a decreasing temperature ramp after mixing to anneal the target strand with the nanoswitch detectors (FIG. 14).

Figure 15:
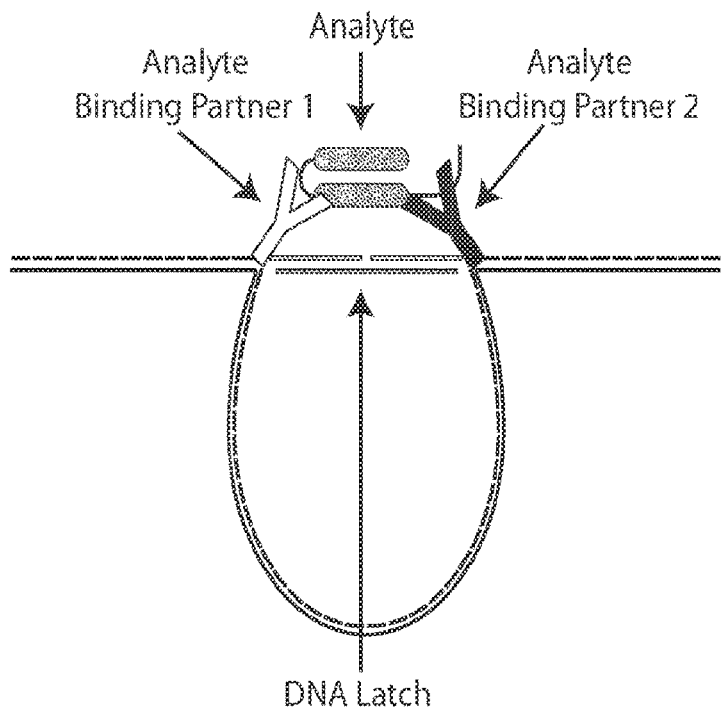
FIG. 15 shows a DNA latch integrated into a DNA nanoswitch antigen detector.

Example 6. Nucleic Acid Latch Integrated into a Nucleic Acid Nanoswitch Antigen Detector FIG. 15 provides a schematic of a latch integrated into a nanoswitch antigen detector (analyte binding partner 1, analyte, and analyte binding partner 2, as shown), essentially creating a nanoscale version of a standard sandwich ELISA assay. The latch consists of 2 single stranded oligonucleotides partially hybridized to the scaffold (denoted "latch acceptor" in the Figure, also referred to herein as latch oligonucleotides) and one single-stranded oligonucleotide hybridized to the two latch acceptors (denoted "DNA latch" in the Figure, also referred to herein as the latch or trigger nucleic acid).

Figure 16:
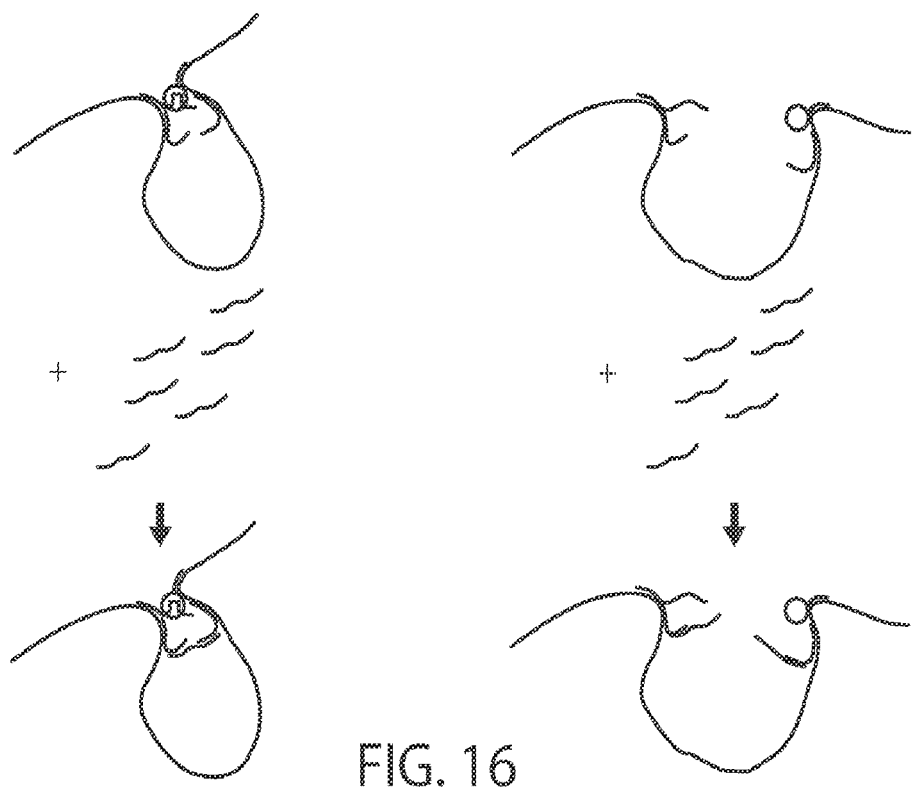
FIG. 16 shows a schematic of a simple DNA latch functioning to close a loop for detection of a protein-aptamer interaction.

Example 7. Nucleic Acid Latch Functioning to Close a Loop for Detection of a Protein-Aptamer Interaction A schematic of a simple nucleic acid latch functioning to close a loop for detection of a protein-aptamer interaction is shown in FIG. 16. When the aptamer is transiently interacting with the protein of interest and the latch nucleic acid is added, the local concentration between the two overhangs is high, and when one overhang binds to the trigger nucleic acid, the trigger nucleic acid also binds to the opposite overhang on the same scaffold, resulting in stable loop formation (left panel). In a control situation, where the aptamer or a control nucleic acid does not interact with the protein, the local concentration between the overhangs is low, and even though one overhang may bind to the trigger nucleic acid, the opposite overhang likely will not bind to the same trigger. Instead, each overhang may bind to a separate trigger nucleic acid, in which case no loop forms (right panel).

Example 8. Weak Aptamer Binding to Streptavidin

Latches can also be used to close loops that result from weak binding interactions. This is shown in FIG. 17 for weak aptamer binding to streptavidin. For the first and third lanes, a latch mechanism was used that uses an amine group at the end of the aptamer sequence. For the second and fourth lanes, oligonucleotides are hybridized adjacent to the biotin-streptavidin and aptamer locations on the scaffold that contain 3-4 amine groups. The first and second lanes include a control sequence with low secondary structure, while the third and fourth lanes include a known aptamer sequence that binds to streptavidin. Looping is detected when the aptamer sequence is present, but not for the control sequence. To perform these experiments, a scaffold with the control or aptamer sequence at one nanoswitch location and a biotinylated oligonucleotide at another nanoswitch location with streptavidin was used. After a 30 minutes incubation, the bifunctional molecule glutaraldehyde was added to a final concentration of 0.25%. The sample was incubated for an additional 45 minutes. The glutaraldehyde crosslinks the amine groups in the nanoswitch, provided they are in sufficiently close proximity, a condition that is met when the streptavidin-specific aptamer interacts with streptavidin.

Example 9. Detection of Weak Aptamer Binding

Another example of a latch that can be used to detect weak aptamer binding is shown in FIG. 18. For the latch components attached to the scaffold, two latch oligonucleotides (or latch acceptors) are included in the nanoswitch composition, and these hybridize adjacent to the aptamer or control sequence and to a hybridized biotinylated oligonucleotide. After a 30 minute incubation with streptavidin, the trigger or latch nucleic acid is added to a final concentration of 14 µM and the mixture is incubated for 45 minutes, before running the mixture on a gel. The left lane with a looped band includes an aptamer sequence known to bind to streptavidin, while the right lane without a looped band includes a control sequence. Here, the complimentary sequences between the trigger or latch nucleic acid and the latch oligonucleotides or acceptors are 15 nucleotides in length. To be clear, the trigger or latch nucleic acids are the nucleic acids that bind to the latch oligonucleotides or acceptors which are themselves partially hybridized to the scaffold in the nanoswitch.

Example 10. Detection of Weak Binding Between Desthiobiotin and Streptavidin

A nucleic acid latch used to detect weak binding between desthiobiotin and streptavidin is shown in FIG. 19. For the latch components attached to the scaffold, two latch oligonucleotides are included in the nanoswitch composition, and these hybridize adjacent to the desthiobiotin and to a hybridized biotinylated oligonucleotide. After a 30 minute incubation with streptavidin (top) or 30 minute incubation in streptavidin-free buffer (bottom), the trigger or latch nucleic acid is added to a final concentration of ranging from 60 µM to 60 µM and incubated for 10 minutes to 10 hours, before running the mixture on a gel. Here, the complimentary sequences between the trigger or latch nucleic acid and the latch oligonucleotides or acceptors are 10 nucleotides in length with the following sequence 5'GCCTCGTCTCGCCTCGTCTC3' (SEQ ID NO: 163). The latches did not give rise to false positives, and instead the loops only form when streptavidin is present. Additionally the last lane on the bottom gel shows that in the presence of desthiobiotin, the loops are not stable enough to remain intact during the 100 minute gel running process if the latch is absent.

Example 11. Kinetic Barrier Latches

FIG. 20 shows a schematic of the activity of kinetic barrier latches that do not require a latch or trigger nucleic acid. Rather in these embodiments, the latch forms through hybridization of the latch oligonucleotide overhangs to each other.

Following removal of a protection strand (referred to as a latch blocker in the Figure) via strand displacement (de-protection), the latch oligonucleotides are available to hybridize to each other when they are brought into close enough proximity. The Figure illustrates a latch blocker as a nucleic acid that binds to an overhang of one of the latch oligonucleotides (OH1). As shown in the top panel, when the latch blocker is hybridized to the overhang (OH1), another overhang is created comprised of latch blocker sequence. Using this overhang as a toehold, another nucleic acid can be introduced having more complementarity to the latch blocker than the latch oligonucleotide overhang (OH1) (e.g., there may be complete complementarity between the latch blocker and the newly introduced nucleic acid throughout both of their lengths, as illustrated). Once the latch blocker hybridizes to the newly introduced nucleic acid, the latch blocker can be displaced from the latch oligonucleotide overhang (OH1), thereby making the latch oligonucleotide overhang (OH1) available to hybridize to its respective latch oligonucleotide overhang (OH2). Latch oligonucleotide overhang OH2 may itself be protected from arbitrarily binding to OH1. For example, it too may be hybridized to a latch blocker, although this embodiment is not illustrated in FIG. 20.

FIG. 20 instead illustrates a opposite latch overhang (OH2) having secondary structure. In this Figure, the two latch overhangs (OH1 and OH2) are not completely complementary. This is conveyed in the bottom right panel where a single-stranded bubble is formed when the overhangs hybridize to each other. In this embodiment, the nucleotide sequence in OH2 that is non-complementary to OH1 is referred to as a kinetic barrier. Once OH1 is released from the latch blocker, it competes with the secondary structure inherent in OH2 for binding to OH2, thereby melting the secondary structure and forming the structure in the bottom right panel.

Example 12. Sequences and Free-Energy Structure Predictions

Figure 21A:
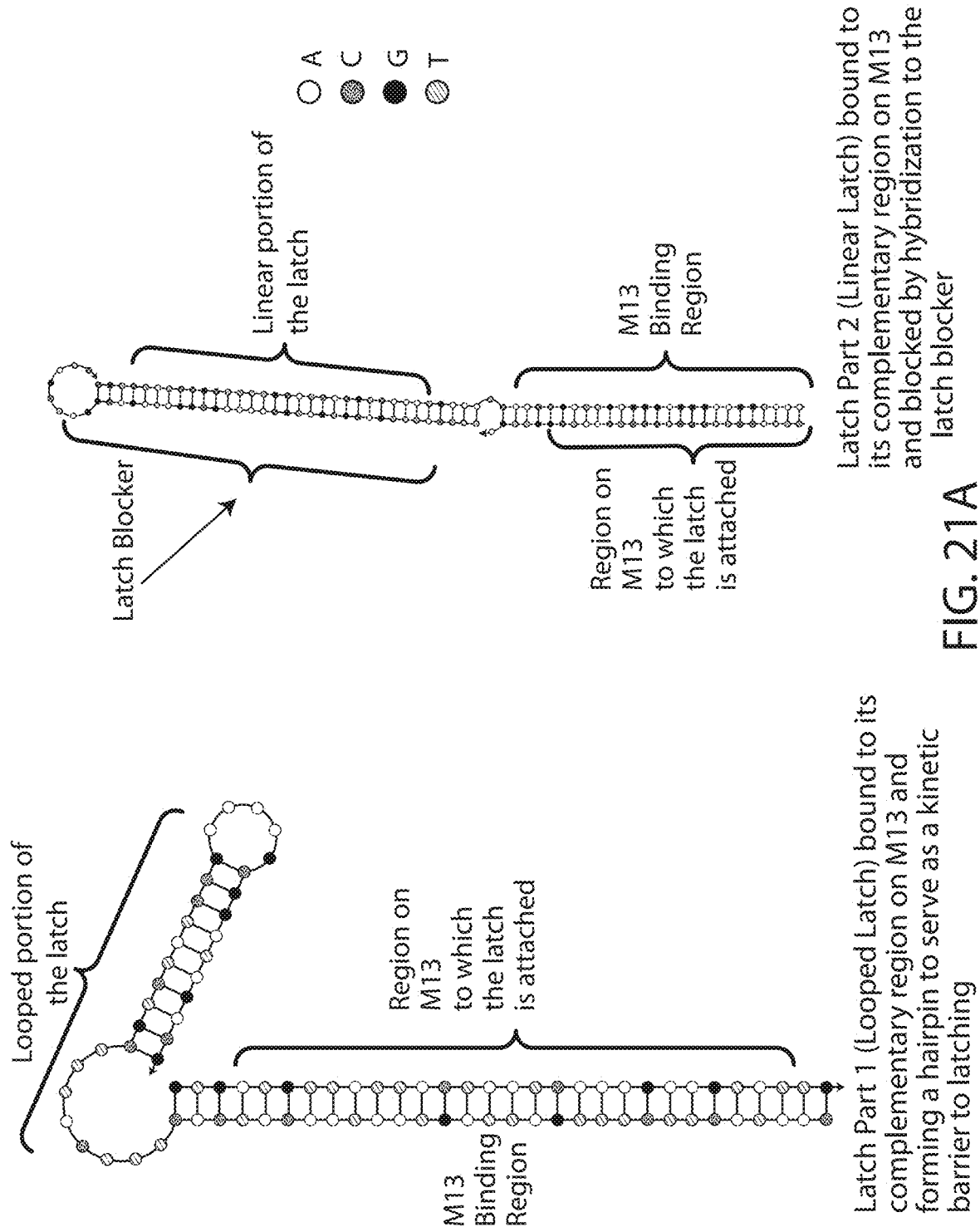
FIGS. 21A-21C show the sequences and free-energy structure predictions of the latches and the segments of M13 to which they bind.
Figure 21B:
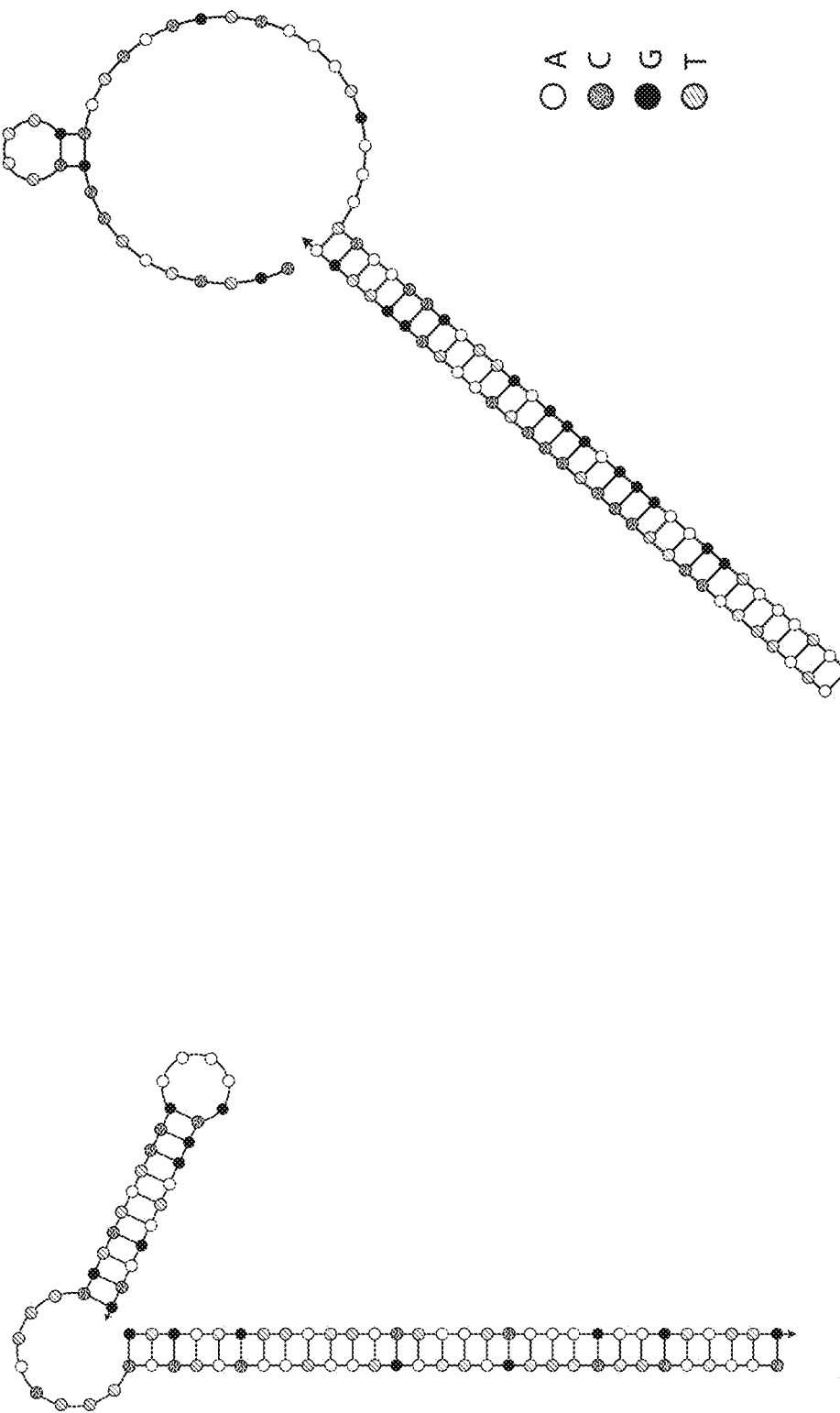
Figure 21C:
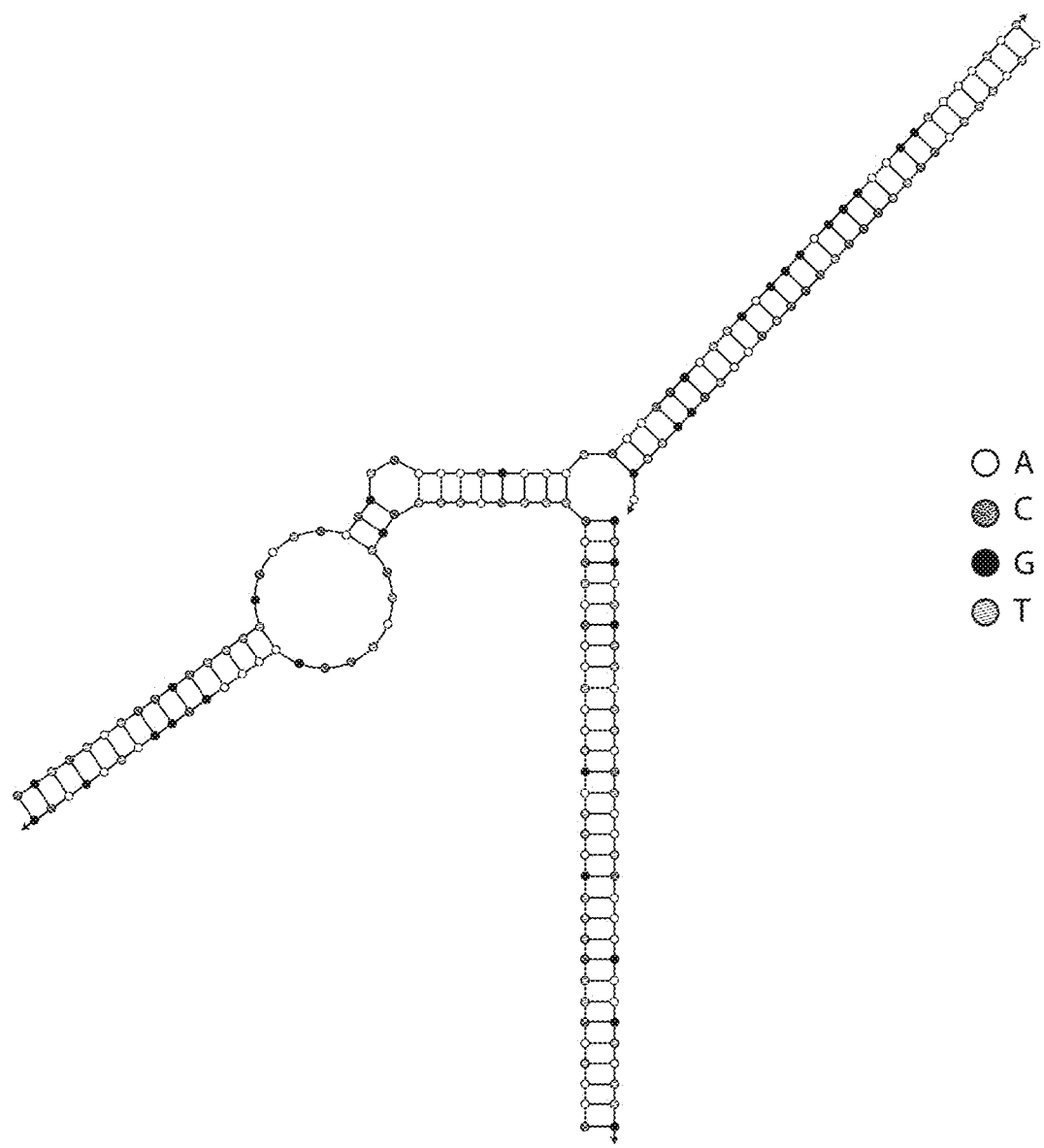

Also provided for exemplary purposes are nucleotide sequences (Table 3) and free-energy structure predictions (FIG. 21) of the latches and the segments of M13 to which they bind. FIG. 21 provides more detailed schematics of the latches described in Example 11. Latch Part 1 (Looped Latch) is bound to its complimentary region on M13 and forms a hairpin to serve as a kinetic barrier to latching (top left panel). Latch Part 2 (Linear Latch) is bound to its complimentary region on M13 and blocked by hybridization to the latch blocker (top right panel). Latch Part 2 is bound to its M13 compliment with the blocking strand removed showing minimal secondary structure (middle right panel). The final panel shows a Latched Complex bound to the two complementary regions on the M13 scaffold.

TABLE 3

Latch Sequences

| Sequence | Description | SEQ ID NO: |
|---|---|---|
| TTTCATTTCGTCTATCCGAAAAGCGGATAGACG | Looped (Latch Part 1) | 164 |
| CAATACTTCTTTGATTAGTAATAACATCACTTTCATTTCGTCTATCCGAAAAGCGGATAGACG | Looped (Latch Part 1) with V4L30 | 165 |
| CGTCTATCCGCTTTTGCATCACGTCAAATGAAA | Latch Part 2 | 166 |
| CGTCTATCCGCTTTTGCATCACGTCAAATGAAATCAACCGATTGAGGGAGGGAAGGTAAATAT | Latch Part 2 with V8F30 | 167 |
| TTTCATTTGACGTGATGCAAAAGCGGATAGACGGATCGATC | Latch Part 2 Blocker | 168 |
| GATCGATCCGTCTATCCGCTTTTGCATCACGTCAAATGAAA | Latch Block Peeler | 169 |

Example 13. Example of High Sensitivity Detection

Figure 22:
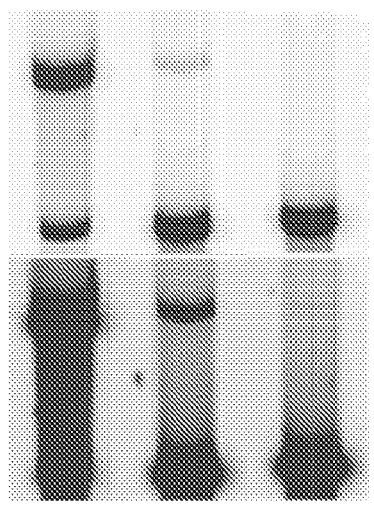
FIG. 22 shows single attomole detection. Low- (Top) and High- (Bottom) contrast images of gels showing detection of 100, 10, and 1 attomole(s) of protein (left to right).

Attomole detection of target proteins is shown in FIG. 22. Low (top) and high (bottom) contrast images of gels show detection of 100, 10, and 1 attomole(s) of protein (left to right).

Example 14. Nucleic Acid Nanoswitch Latch Applications

Nanoswitch latches can be used to in the detection of protein analytes. For example, the nanoswitches and corresponding latches can be used to detect protein analytes such as but not limited to Early Pregnancy Factor (EPF), Prostate-Specific Antigen (PSA), and tumor necrosis factor-α (TNF-α), and other clinically relevant proteins. The latching systems described herein can detect proteins at a much lower concentration than traditional ELISA. Protein targets may be detected by using a nanoswitch having two target-specific binding partners that each bind to the same target, thereby creating a loop in the nanoswitch.

Figure 23:
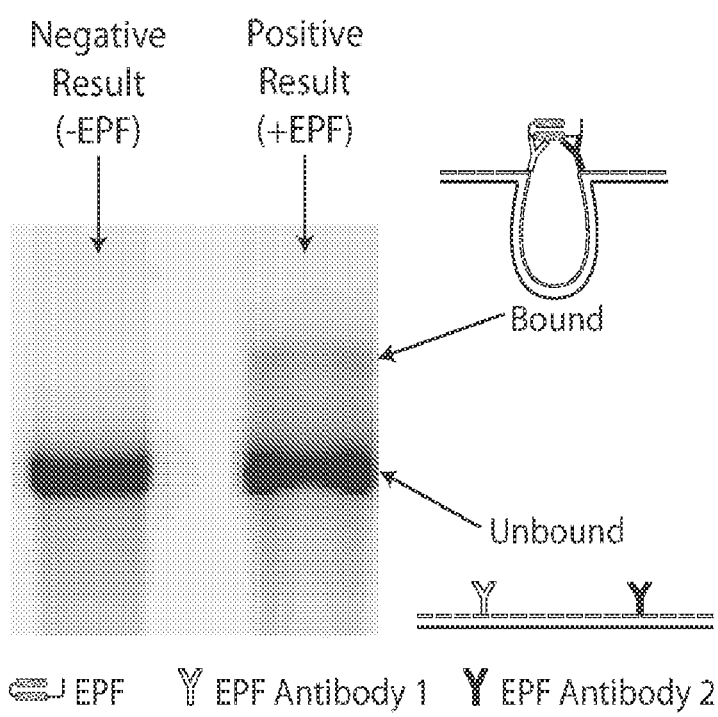
FIG. 23 shows preliminary data showing early pregnancy factor (EPF) detection with a DNA nanoswitch assay.

This Example demonstrates the use of such a nanoswitch and latch in the detection of Early Pregnancy Factor (EPF) (FIG. 23). For each assay, two sets of binding partners (such as target-specific antibodies or target-specific antibody fragments) are used to sandwich the target and form a loop. For stable loop formation, components of the latch system are hybridized interior to the sites of antibody attachment.

For TNF-α detection, monoclonal mouse IgG1 Clone #28401 and Antigen Affinity-purified Polyclonal Goat IgG (R & D Systems) were used. For PSA detection, anti-PSA clone 8301 and anti-PSA clone 8311 were used (BiosPacific). Both detection antibodies are attached to oligonucleotides complimentary to the scaffold using the bifunctional linker, DBCO-PEG4-NHS ester, which will react with amine groups on the antibodies and with azide-modified oligonucleotides. After coupling, the antibodies are purified from excess oligonucleotide and linker using PIERCE™ Protein A/G Magnetic Beads. The latch oligonucleotides are hybridized to the scaffold by mixing them, and an excess of backbone (or fixed) oligonucleotides, and the M13 scaffold, heating to 90° C. and cooling to 20° C. by one degree per minute. The antibodies are hybridized to the nanoswitch scaffold in excess by adding at a temperature of 37° C., and after the nanoswitch is formed it is purified from excess antibodies using PEG precipitation. We test for detection using spike-ins of known PSA (BiosPacific) or TNF-α (R & D Systems) in a ¼ dilution of fetal bovine serum (FBS).

After loops are formed, gel electrophoresis is performed to separate the looped conformation bands, which can be detected using SYBR-gold, YOYO, DNA extraction and qPCR, or another method to allow quantification of the amount of looped nanoswitch, which corresponds to the amount of analyte.

Pregnancy-detection applications may involve the detection of analytes such as EPF (Early Pregnancy Factor), human chorionic gonadotropin (HCG), and luteinizing hormone (LH).

Examples of specific antibodies used in a direct cross-linking system include but are not limited to Anti-HSPE1/HSP10/Chaperonin 10 Antibody (aa91-101, Biotin) LS-C232123, Anti-HSPE1/HSP10/Chaperonin 10 Antibody (aa38-64, Biotin) LS-C236441, Anti-Cpn10 antibody [EPR4475] (ab108611), Anti-Cpn10 antibody [EPR4476] (ab108600), Anti-Cpn10 antibody [EPR4476] (ab108600), and HSP 10 Antibody (D-8): sc-376313. These or any other antibody, aptamer, binding partner, or reactant could be used to bind EPF.

Additional sequences for generating nanoswitches with and without latches can be found in Tables 4-10 below.

TABLE 4

Backbone Oligonucleotide Sequences

| SEQ ID NO: | Sequence | Length |
|---|---|---|
| 1 | AGAGCATAAAGCTAAATCGGTTGTACCAAAAACATTATGACCCTGTAATACTTTTGCGGG | 60 |
| 2 | AGAAGCCTTTATTTCAACGCAAGGATAAAAATTTTTAGAACCCTCATATATTTTAAATGC | 60 |
| 3 | AATGCCTGAGTAATGTGTAGGTAAAGATTCAAAAGGGTGAGAAAGGCCGGAGACAGTCAA | 60 |
| 4 | ATCACCATCAATATGATATTCAACCGTTCTAGCTGATAAATTAATGCCGGAGAGGGTAGC | 60 |
| 5 | TATTTTTGAGAGATCTACAAAGGCTATCAGGTCATTGCCTGAGAGTCTGGAGCAAACAAG | 60 |
| 6 | AGAATCGATGAACGGTAATCGTAAAACTAGCATGTCAATCATATGTACCCCGGTTGATAA | 60 |
| 7 | TCAGAAAAGCCCCAAAAACAGGAAGATTGTATAAGCAAATATTTAAATTGTAAACGTTAA | 60 |
| 8 | TATTTTGTTAAAATTCGCATTAAATTTTTGTTAAATCAGCTCATTTTTTAACCAATAGGA | 60 |
| 9 | ACGCCATCAAAAATAATTCGCGTCTGGCCTTCCTGTAGCCAGCTTTCATCAACATTAAAT | 60 |
| 10 | GGATAGGTCACGTTGGTGTAGATGGGCGCATCGTAACCGTGCATCTGCCAGTTTGAGGGG | 60 |
| 11 | ACGACGACAGTATCGGCCTCAGGAAGATCGCACTCCAGCCAGCTTTCCGGCACCGCTTCT | 60 |
| 12 | GGTGCCGGAAACCAGGCAAAGCGCCATTCGCCATTCAGGCTGCGCAACTGTTGGGAAGGG | 60 |
| 13 | CGATCGGTGCGGGCCTCTTCGCTATTACGCCAGCTGGCGAAAGGGGGATGTGCTGCAAGG | 60 |
| 14 | CGATTAAGTTGGGTAACGCCAGGGTTTTCCCAGTCACGACGTTGTAAAACGACGGCCAGT | 60 |
| 15 | GCCAAGCTTGCATGCCTGCAGGTCGACTCTAGAGGATCCCCGGGTACCGAGCTCGAATTC | 60 |
| 16 | GTAATCATGGTCATAGCTGTTTCCTGTGTGAAATTGTTATCCGCTCACAATTCCACACAA | 60 |
| 17 | CATACGAGCCGGAAGCATAAAGTGTAAAGCCTGGGGTGCCTAATGAGTGAGCTAACTCAC | 60 |
| 18 | ATTAATTGCGTTGCGCTCACTGCCCGCTTTCCAGTCGGGAAACCTGTCGTGCCAGCTGCA | 60 |
| 19 | TTAATGAATCGGCCAACGCGCGGGGAGAGGCGGTTTGCGTATTGGGCGCCAGGGTGGTTT | 60 |
| 20 | GTTGCAGCAAGCGGTCCACGCTGGTTTGCCCCAGCAGGCGAAAATCCTGTTTGATGGTGG | 60 |
| 21 | TTCCGAAATCGGCAAAATCCCTTATAAATCAAAAGAATAGCCCGAGATAGGGTTGAGTGT | 60 |
| 22 | TGTTCCAGTTTGGAACAAGAGTCCACTATTAAAGAACGTGGACTCCAACGTCAAAGGGCG | 60 |
| 23 | AAAAACCGTCTATCAGGGCGATGGCCCACTACGTGAACCATCACCCAAATCAAGTTTTTT | 60 |
| 24 | GGGGTCGAGGTGCCGTAAAGCACTAAATCGGAACCCTAAAGGGAGCCCCCGATTTAGAGC | 60 |

TABLE 4-continued

Backbone Oligonucleotide Sequences

| SEQ ID NO: | Sequence | Length |
|---|---|---|
| 25 | TTGACGGGGAAAGCCGGCGAACGTGGCGAGAAAGGAAGGGAAGAAAGCGAAAGGAGCGGG | 60 |
| 26 | CGCTAGGGCGCTGGCAAGTGTAGCGGTCACGCTGCGCGTAACCACCACACCCGCCGCGCT | 60 |
| 27 | TAATGCGCCGCTACAGGGCGCGTACTATGGTTGCTTTGACGAGCACGTATAACGTGCTTT | 60 |
| 28 | CCTCGTTAGAATCAGAGCGGGAGCTAAACAGGAGGCCGATTAAAGGGATTTTAGACAGGA | 60 |
| 29 | ACGGTACGCCAGAATCCTGAGAAGTGTTTTTATAATCAGTGAGGCCACCGAGTAAAAGAG | 60 |
| 30 | TTGCCTGAGTAGAAGAACTCAAACTATCGGCCTTGCTGGTAATATCCAGAACAATATTAC | 60 |
| 31 | CGCCAGCCATTGCAACAGGAAAAACGCTCATGGAAATACCTACATTTTGACGCTCAATCG | 60 |
| 32 | TCTGAAATGGATTATTTACATTGGCAGATTCACCAGTCACACGACCAGTAATAAAAGGGA | 60 |
| 33 | CATTCTGGCCAACAGAGATAGAACCCTTCTGACCTGAAAGCGTAAGAATACGTGGCACAG | 60 |
| 34 | ACAATATTTTTGAATGGCTATTAGTCTTTAATGCGCGAACTGATAGCCCTAAAACATCGC | 60 |
| 35 | CATTAAAAATACCGAACGAACCACCAGCAGAAGATAAAACAGAGGTGAGGCGGTCAGTAT | 60 |
| 36 | TAACACCGCCTGCAACAGTGCCACGCTGAGAGCCAGCAGCAAATGAAAAATCTAAAGCAT | 60 |
| 37 | CACCTTGCTGAACCTCAAATATCAAACCCTCAATCAATATCTGGTCAGTTGGCAAATCAA | 60 |
| 38 | CAGTTGAAAGGAATTGAGGAAGGTTATCTAAAATATCTTTAGGAGCACTAACAACTAATA | 60 |
| 39 | GATTAGAGCCGTCAATAGATAATACATTTGAGGATTTAGAAGTATTAGACTTTACAAACA | 60 |
| 40 | CATTATCATTTTGCGGAACAAAGAAACCACCAGAAGGAGCGGAATTATCATCATATTCCT | 60 |
| 41 | GATTATCAGATGATGGCAATTCATCAATATAATCCTGATTGTTTGGATTATACTTCTGAA | 60 |
| 42 | TAATGGAAGGGTTAGAACCTACCATATCAAAATTATTTGCACGTAAAACAGAAATAAAGA | 60 |
| 43 | AATTGCGTAGATTTTCAGGTTTAACGTCAGATGAATATACAGTAACAGTACCTTTTACAT | 60 |
| 44 | CGGGAGAAACAATAACGGATTCGCCTGATTGCTTTGAATACCAAGTTACAAAATCGCGCA | 60 |
| 45 | GAGGCGAATTATTCATTTCAATTACCTGAGCAAAAGAAGATGATGAAACAAACATCAAGA | 60 |
| 46 | AAACAAAATTAATTACATTTAACAATTTCATTTGAATTACCTTTTTTAATGGAAACAGTA | 60 |
| 47 | CATAAATCAATATATGTGAGTGAATAACCTTGCTTCTGTAAATCGTCGCTATTAATTAAT | 60 |
| 48 | TTTCCCTTAGAATCCTTGAAAACATAGCGATAGCTTAGATTAAGACGCTGAGAAGAGTCA | 60 |
| 49 | ATAGTGAATTTATCAAAATCATAGGTCTGAGAGACTACCTTTTTAACCTCCGGCTTAGGT | 60 |
| 50 | GAAACTTTTTCAAATATATTTTAGTTAATTTCATCTTCTGACCTAAATTTAATGGTTTG | 60 |
| 51 | AAATACCGACCGTGTGATAAATAAGGCGTTAAATAAGAATAAACACCGGAATCATAATTA | 60 |
| 52 | CTAGAAAAGCCTGTTTAGTATCATATGCGTTATACAAATTCTTACCAGTATAAAGCCAA | 60 |
| 53 | CGCTCAACAGTAGGGCTTAATTGAGAATCGCCATATTTAACAACGCCAACATGTAATTTA | 60 |
| 54 | GGCAGAGGCATTTTCGAGCCAGTAATAAGAGAATATAAAGTACCGACAAAAGGTAAAGTA | 60 |
| 55 | ATTCTGTCCAGACGACGACAATAAACAACATGTTCAGCTAATGCAGAACGCGCCTGTTTA | 60 |
| 56 | TCAACAATAGATAAGTCCTGAACAAGAAAAATAATATCCCATCCTAATTTACGAGCATGT | 60 |
| 57 | AGAAACCAATCAATAATCGGCTGTCTTTCCTTATCATTCCAAGAACGGGTATTAAACCAA | 60 |
| 58 | GTACCGCACTCATCGAGAACAAGCAAGCCGTTTTTATTTTCATCGTAGGAATCATTACCG | 60 |
| 59 | CGCCCAATAGCAAGCAAATCAGATATAGAAGGCTTATCCGGTATTCTAAGAACGCGAGGC | 60 |
| 60 | ATTTTGCACCCAGCTACAATTTTATCCTGAATCTTACCAACGCTAACGAGCGTCTTTCCA | 60 |
| 61 | GAGCCTAATTTGCCAGTTACAAAATAAACAGCCATATTATTTATCCCAATCCAAATAAGA | 60 |
| 62 | AACGATTTTTTGTTTAACGTCAAAAATGAAAATAGCAGCCTTTACAGAGAGAATAACATA | 60 |

TABLE 4-continued

Backbone Oligonucleotide Sequences

| SEQ ID NO: | Sequence | Length |
|---|---|---|
| 63 | AAAACAGGGAAGCGCATTAGACGGGAGAATTAACTGAACACCCTGAACAAAGTCAGAGGG | 60 |
| 64 | TAATTGAGCGCTAATATCAGAGAGATAACCCACAAGAATTGAGTTAAGCCCAATAATAAG | 60 |
| 65 | AGCAAGAAACAATGAAATAGCAATAGCTATCTTACCGAAGCCCTTTTTAAGAAAAGTAAG | 60 |
| 66 | CAGATAGCCGAACAAAGTTACCAGAAGGAAACCGAGGAAACGCAATAATAACGGAATACC | 60 |
| 67 | CAAAAGAACTGGCATGATTAAGACTCCTTATTACGCAGTATGTTAGCAAACGTAGAAAAT | 60 |
| 68 | ACATACATAAAGGTGGCAACATATAAAAGAAACGCAAAGACACCACGGAATAAGTTTATT | 60 |
| 69 | TTGTCACAATCAATAGAAAATTCATATGGTTTACCAGCGCCAAAGACAAAAGGGCGACAT | 60 |
| 70 | TCACCGTCACCGACTTGAGCCATTTGGGAATTAGAGCCAGCAAAATCACCAGTAGCACCA | 60 |
| 71 | TTACCATTAGCAAGGCCGGAAACGTCACCAATGAAACCATCGATAGCAGCACCGTAATCA | 60 |
| 72 | GTAGCGACAGAATCAAGTTTGCCTTTAGCGTCAGACTGTAGCGCGTTTTCATCGGCATTT | 60 |
| 73 | TCGGTCATAGCCCCCTTATTAGCGTTTGCCATCTTTTCATAATCAAATCACCGGAACCA | 60 |
| 74 | GAGCCACCACCGGAACCGCCTCCCTCAGAGCCGCCACCCTCAGAACCGCCACCCTCAGAG | 60 |
| 75 | CCACCACCCTCAGAGCCGCCACCAGAACCACCACCAGAGCCGCCGCCAGCATTGACAGGA | 60 |
| 76 | GGTTGAGGCAGGTCAGACGATTGGCCTTGATATTCACAAACAAATAAATCCTCATTAAAG | 60 |
| 77 | CCAGAATGGAAAGCGCAGTCTCTGAATTTACCGTTCCAGTAAGCGTCATACATGGCTTTT | 60 |
| 78 | GATGATACAGGAGTGTACTGGTAATAAGTTTTAACGGGGTCAGTGCCTTGAGTAACAGTG | 60 |
| 79 | CCCGTATAAACAGTTAATGCCCCCTGCCTATTTCGGAACCTATTATTCTGAAACATGAAA | 60 |
| 80 | CCAGGCGGATAAGTGCCGTCGAGAGGGTTGATATAAGTATAGCCCGGAATAGGTGTATCA | 60 |
| 81 | CCGTACTCAGGAGGTTTAGTACCGCCACCCTCAGAACCGCCACCCTCAGAACCGCCACCC | 60 |
| 82 | TCAGAGCCACCACCCTCATTTTCAGGGATAGCAAGCCCAATAGGAACCCATGTACCGTAA | 60 |
| 83 | CACTGAGTTTCGTCACCAGTACAAACTACAACGCCTGTAGCATTCCACAGACAGCCCTCA | 60 |
| 84 | TAGTTAGCGTAACGATCTAAAGTTTTGTCGTCTTTCCAGACGTTAGTAAATGAATTTTCT | 60 |
| 85 | GTATGGGATTTTGCTAAACAACTTTCAACAGTTTCAGCGGAGTGAGAATAGAAAGGAACA | 60 |
| 86 | ACTAAAGGAATTGCGAATAATAATTTTTTCACGTTGAAAATCTCCAAAAAAAGGCTCCA | 60 |
| 87 | AAAGGAGCCTTTAATTGTATCGGTTTATCAGCTTGCTTTCGAGGTGAATTTCTTAAACAG | 60 |
| 88 | CTTGATACCGATAGTTGCGCCGACAATGACAACAACCATCGCCCACGCATAACCGATATA | 60 |
| 89 | TTCGGTCGCTGAGGCTTGCAGGGAGTTAAAGGCCGCTTTTGCGGGATCGTCACCCTCAGC | 60 |
| 90 | CTTTTTCATGAGGAAGTTTCCATTAAACGGGTAAAATACGTAATGCCACTACGAAGGCAC | 60 |
| 91 | CAACCTAAAACGAAAGAGGCAAAAGAATACACTAAAACACTCATCTTTGACCCCCAGCGA | 60 |
| 92 | TTATACCAAGCGCGAAACAAAGTACAACGGAGATTTGTATCATCGCCTGATAAATTGTGT | 60 |
| 93 | CGAAATCCGCGACCTGCTCCATGTTACTTAGCCGGAACGAGGCGCAGACGGTCAATCATA | 60 |
| 94 | AGGGAACCGAACTGACCAACTTTGAAAGAGGACAGATGAACGGTGTACAGACCAGGCGCA | 60 |
| 95 | TAGGCTGGCTGACCTTCATCAAGAGTAATCTTGACAAGAACCGGATATTCATTACCCAAA | 60 |
| 96 | TCAACGTAACAAAGCTGCTCATTCAGTGAATAAGGCTTGCCCTGACGAGAAACACCAGAA | 60 |
| 97 | CGAGTAGTAAATTGGGCTTGAGATGGTTTAATTTCAACTTTAATCATTGTGAATTACCTT | 60 |
| 98 | ATGCGATTTTAAGAACTGGCTCATTATACCAGTCAGGACGTTGGGAAGAAAAATCTACGT | 60 |
| 99 | TAATAAAACGAACTAACGGAACAACATTATTACAGGTAGAAAGATTCATCAGTTGAGATT | 60 |

TABLE 4-continued

Backbone Oligonucleotide Sequences

| SEQ ID NO: | Sequence | Length |
|---|---|---|
| 100 | TAAGAGCAACACTATCATAACCCTCGTTTACCAGACGACGATAAAAACCAAAATAGCGAG | 60 |
| 101 | AGGCTTTTGCAAAAGAAGTTTTGCCAGAGGGGTAATAGTAAAATGTTTAGACTGGATAG | 60 |
| 102 | CGTCCAATACTGCGGAATCGTCATAAATATTCATTGAATCCCCCTCAAATGCTTTAAACA | 60 |
| 103 | GTTCAGAAAACGAGAATGACCATAAATCAAAAATCAGGTCTTTACCCTGACTATTATAGT | 60 |
| 104 | CAGAAGCAAAGCGGATTGCATCAAAAAGATTAAGAGGAAGCCCGAAAGACTTCAAATATC | 60 |
| 105 | GCGTTTTAATTCGAGCTTCAAAGCGAACCAGACCGGAAGCAAACTCCAACAGGTCAGGAT | 60 |
| 106 | TAGAGAGTACCTTTAATTGCTCCTTTTGATAAGAGGTCATTTTTGCGGATGGCTTAGAGC | 60 |
| 107 | TTAATTGCTGAATATAATGCTGTAGCTCAACATGTTTTAAATATGCAACTAAAGTACGGT | 60 |
| 108 | GTCTGGAAGTTTCATTCCATATAACAGTTGATTCCCAATTCTGCGAACGAGTAGATTTAG | 60 |
| 109 | TTTGACCATTAGATACATTTCGCAAATGGTCAATAACCTGTTTAGCTAT | 49 |

TABLE 5

Sequences for DNA Detection. Regions of detectors binding to the key oligonucleotides are underlined.

| # | SEQ ID NO: | Sequence | Length |
|---|---|---|---|
| *Variable sequences* | | | |
| Var 1 | 110 | AACATCCAATAAATCATACAGGCAAGGCAAAGAATTAGCAAAATTAAGCAATAAAGCCTC | 60 |
| Var 2 | 111 | GTGAGCGAGTAACAACCCGTCGGATTCTCCGTGGGAACAAACGGCGGATTGACCGTAATG | 60 |
| Var 3 | 112 | TTCTTTTCACCAGTGAGACGGGCAACAGCTGATTGCCCTTCACCGCCTGGCCCTGAGAGA | 60 |
| Var 4 | 113 | TCTGTCCATCACGCAAATTAACCGTTGTAGCAATACTTCTTTGATTAGTAATAACATCAC | 60 |
| Var 5 | 114 | ATTCGACAACTCGTATTAAATCCTTTGCCCGAACGTTATTAATTTTAAAAGTTTGAGTAA | 60 |
| Var 6 | 115 | TGGGTTATATAACTATATGTAAATGCTGATGCAAATCCAATCGCAAGACAAAGAACGCGA | 60 |
| Var 7 | 116 | GTTTTAGCGAACCTCCCGACTTGCGGGAGGTTTTGAAGCCTTAAATCAAGATTAGTTGCT | 60 |
| Var 8 | 117 | TCAACCGATTGAGGGAGGGAAGGTAAATATTGACGGAAATTATTCATTAAAGGTGAATTA | 60 |
| Var 9 | 118 | GTATTAAGAGGCTGAGACTCCTCAAGAGAAGGATTAGGATTAGCGGGGTTTTGCTCAGTA | 60 |
| Var 10 | 119 | AGCGAAAGACAGCATCGGAACGAGGGTAGCAACGGCTACAGAGGCTTTGAGGACTAAAGA | 60 |
| Var 11 | 120 | TAGGAATACCACATTCAACTAATGCAGATACATAACGCCAAAAGGAATTACGAGGCATAG | 60 |
| Var 12 | 121 | ATTTTCATTTGGGGCGCGAGCTGAAAAGGTGGCATCAATTCTACTAATAGTAGTAGCATT | 60 |
| *Detector sequences* | | | |
| D1 | 122 | ACCGTTGTAGCAATACTTCTTTGATTAGTAATAACATCAC<u>TTCAGATTGAAGGGC</u> | 55 |
| D2 | 123 | <u>CATGAGACCGTGTCCT</u>CAACCGATTGAGGGAGGGAAGGTAAATATTGACGGAAAT | 55 |
| *Filler sequences* | | | |
| F1 | 124 | TCTGTCCATCACGCAAATTA | 20 |
| F2 | 125 | TATTCATTAAAGGTGAATTA | 20 |

Key Nucleotide Sequences (Symmetric)

TABLE 6

Key Nucleotide Sequences (Symmetric).

| # | SEQ ID NO: | Sequence | Length |
|---|---|---|---|
| K30 | 126 | GGACACGGTCTCATGGCCCTTCAATCTGAA | 30 |
| K28 | 127 | GACACGGTCTCATGGCCCTTCAATCTGA | 28 |
| K26 | 128 | ACACGGTCTCATGGCCCTTCAATCTG | 26 |

TABLE 6-continued

Key Nucleotide Sequences (Symmetric).

| # | SEQ ID NO: | Sequence | Length |
|---|---|---|---|
| K24 | 129 | CACGGTCTCATGGCCCTTCAATCT | 24 |
| K22 | 130 | ACGGTCTCATGGCCCTTCAATC | 22 |
| K20 | 131 | CGGTCTCATGGCCCTTCAAT | 20 |

TABLE 7

Key Oligonucleotide Sequences (Asymmetric)

| # | SEQ ID NO: | Sequence | Length |
|---|---|---|---|
| K30/15-15 | 132 | GGACACGGTCTCATG GCCCTTCAATCTGAA | 30 |
| K29/15-14 | 133 | GGACACGGTCTCATG GCCCTTCAATCTGA | 29 |
| K28/15-13 | 134 | GGACACGGTCTCATG GCCCTTCAATCTG | 28 |
| K27/15-12 | 135 | GGACACGGTCTCATG GCCCTTCAATCT | 27 |
| K26/15-11 | 136 | GGACACGGTCTCATG GCCCTTCAATC | 26 |
| K25/15-10 | 137 | GGACACGGTCTCATG GCCCTTCAAT | 25 |
| K24/15-9 | 138 | GGACACGGTCTCATG GCCCTTCAA | 24 |
| K24/15-8 | 139 | GGACACGGTCTCATG GCCCTTCA | 23 |
| K24/15-7 | 140 | GGACACGGTCTCATG GCCCTTC | 22 |
| K24/15-6 | 141 | GGACACGGTCTCATG GCCCTT | 21 |
| K24/15-5 | 142 | GGACACGGTCTCATG GCCCT | 20 |

TABLE 8

Sequence-specificity Analysis: Switch A

| # | SEQ ID NO: | Sequence | Length |
|---|---|---|---|
| D1 | 143 | ACCGTTGTAGCAATACTTCTTTGATTAGTAATAACATCACTTCAGATTGAAGGGC | 55 |
| D2 | 144 | CATGAGACCGTGTCCTCAACCGATTGAGGGAGGGAAGGTAAATATTGACGGAAAT | 55 |
| F1 | 145 | TCTGTCCATCACGCAAATTA | 20 |
| F2 | 146 | TATTCATTAAAGGTGAATTA | 20 |
| Key A | 147 | ACGGTCTCATGGCCCTTCAATC | 22 |

TABLE 9

Sequencce-specificity Analysis: Switch B

| # | SEQ ID NO: | Sequence | Length |
|---|---|---|---|
| D1-B | 148 | ACCGTTGTAGCAATACTTCTTTGATTAGTAATAACATCACCACAAATTCGG | 51 |
| D2-B | 149 | TTCTACAGGGTATCAACCGATTGAGGGAGGGAAGGTAAATATTGACGGAAAT | 52 |

TABLE 9-continued

Sequencce-specificity Analysis: Switch B

| # | SEQ ID NO: | Sequence | Length |
|---|---|---|---|
| F1 | 150 | TCTGTCCATCACGCAAATTA | 20 |
| F2 | 151 | TATTCATTAAAGGTGAATTA | 20 |
| Key B | 152 | TACCCTGTAGAACCGAATTTGTG | 23 |

TABLE 10

UV Melting Studies

| # | SEQ ID NO: | Sequence | Length |
|---|---|---|---|
| det-1 | 153 | TTCAGATTGAAGGGC | 15 |
| det-2 | 154 | CATGAGACCGTGTCC | 15 |
| scaffold 1 | 155 | ATTTCCGTCAATATTTACCTTCCCTCCCTCAATCGGTTGA | 40 |
| scaffold 2 | 156 | GTGATGTTATTACTAATCAAAGAAGTATTGCTACAACGGT | 40 |
| det-1-40 (D1) | 157 | ACCGTTGTAGCAATACTTCTTTGATTAGTAATAACATCACTTCAGATTGAAGGGC | 55 |
| det2-40 (D2) | 158 | CATGAGACCGTGTCCTCAACCGATTGAGGGAGGGAAGGTAAATATTGACGGAAAT | 55 |
| det1-30 | 159 | CAATACTTCTTTGATTAGTAATAACATCACTTCAGATTGAAGGGC | 45 |
| det2-30 | 160 | CATGAGACCGTGTCCTCAACCGATTGAGGGAGGGAAGGTAAATAT | 45 |

TABLE 11

Latch Sequences

Components of 15 mer latch, with experimental results shown herein

| Sequence | Name | SEQ ID |
|---|---|---|
| GTCGTTCGCTTCTCTATGTGTCTTCCGGCCC | Bridge_15 | 170 |
| TCAGTTGGCAAATCAACAGTTGAAAGGAATTAGGGCCGGAAGACACA | Anchor_VarD_15 | 171 |
| AGAGAAGCGAACGACATGGGTTATATAACTATATGTAAATGCTGA | Anchor_Var6_15 | 172 |

Componenets of Amine latch, with experimental results shown herein

| Sequence | Name | SEQ ID |
|---|---|---|
| TCAGTTGGCAAATCAACAGTTGAAAGGAA\iAmMC6T\\iSp9\\iAmMC6T\TTTT\3AmMC6T\ | Anchor_VarD_amine | 173 |
| \5AmMC6\\iAmMC6T\TTTT\iAmMC6T\\iSp9\\iAmMC6T\GGGTTATATAACTATATGTAAATGCTGA | Anchor_Var6_amine | 174 |

EXAMPLE REFERENCES

[1] N. C. Seeman, Nature 2003, 421, 427-431
[2] M. R. Jones, N. C. Seeman, C. A. Mirkin, Science 2015, 347, 1260901.
[3] E. Winfree, F. Liu, L. A. Wenzler, N. C. Seeman, Nature 1998, 394, 539-544.
[4] J. Zheng, J. J. Birktoft, Y. Chen, T. Wang, R. Sha, P. E. Constantinou, S. L. Ginell, C. Mao, N. C. Seeman, Nature 2009, 461, 74-77
[5] R. Sha, J. J. Birktoft, N. Nguyen, A. R. Chandrasekaran, J. Zheng, X. Zhao, C. Mao, N. C. Seeman, Nano Lett. 2013, 13, 793-797
[6] D. A. Rusling, A. R. Chandrasekaran, Y. P. Ohayon, T. Brown, K. R. Fox, R. Sha, C. Mao, N. C. Seeman, Angew. Chem. Int. Ed. 2014, 53, 3979-3982.
[7] P. W. K. Rothemund, Nature 2006, 440, 297-302
[8] S. M. Douglas, H. Dietz, T. Liedl, B. Högberg, F. Graf, W. M. Shih, Nature 2009, 459, 414-418.
[9] E. S. Andersen, M. Dong, M. M. Nielsen, K. Jahn, R. Subramani, W. Mamdouh, M. M. Golas, B. Sander, H. Stark, C. L. Oliveira, J. S. Pedersen, V. Birkedal, F. Besenbacher, K. V. Gothelf, J. Kjems, Self-assembly of a nanoscale DNA box with a controllable lid. Nature 2009, 459, 73-76.

[10] A. Idili, A. Vallde-Bélisle, F. Ricci, J. Am. Chem. Soc. 2014, 136, 5836-5839.

[11] S. M. Douglas, I. Bachelet, G. M. Church, Science 2012, 335, 831-834

[12] S. Modi, M. G. Swetha, D. Goswami, G. D. Gupta, S. Mayor, Y. Krishnan, Nature Nanotech. 2009, 4, 325-330

[13] E. S. Andersen, M. Dong, M. M. Nielsen, K. Jahn, R. Subramani, W. Mamdouh, M. M. Golas, B. Sander, H. Stark, C. L. Oliveira, et al. Nature 2009, 459, 73-76.

[14] K. Halvorsen, D. Schaak, W. P. Wong, Nanotechnology 2011, 22, 494005

[15] M. A. Koussa, K. Halvorsen, A. Ward, W. P. Wong, Nat. Methods, 2015, 12, 123-126.

[16] J. M. Butler, Forensic DNA Typing: Biology, Technology, and Genetics of STR Markers (2nd Edition), Elsevier Academic Press, New York, 2005, p. 688.

[17] N. L. Rosi, C. A. Mirkin, Chem. Rev., 2005, 105, 1547-1562.

[18] H. Pei, N. Lu, Y. Wen, S. Song, Y. Liu, H. Yan, C. Fan, Adv. Mater., 2010, 22, 4754-4758.

[19] R. Elghanian, J. J. Storhoff, R. C. Mucic, R. L. Letsinger, C. A. Mirkin, Science 1997, 277, 1078-1081.

[20] K. Halvorsen, P. F. Agris, Anal. Biochem. 2014, 465, 127-133.

[21] M. A. Koussa, M. Sotomayor, W. P. Wong, Protocol for sortase-mediated construction of DNA-protein hybrids and functional nanostructures. Methods 2014, 67, 134-141.

[22] J. L. Mergny, L. Lacroix, Analysis of thermal melting curves. Oligonucleotides 2003, 13, 515-37.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for stabilizing a nanoswitch in a looped conformation, comprising providing a nucleic acid-based nanoswitch, conjugated to a first binding partner and a second binding partner, wherein the first binding partner is bound (i) directly to the second binding partner or (ii) to an analyte bound to the second binding partner, in a first binding interaction, and the nanoswitch thereby adopts a looped conformation, and contacting the nucleic acid-based nanoswitch in the looped conformation with a latch nucleic acid to form a second binding interaction in the nanoswitch, thereby stabilizing the nanoswitch in the looped conformation without affecting loop size, wherein the nucleic acid-based nanoswitch comprises a scaffold nucleic acid hybridized to a plurality of oligonucleotides, wherein the plurality of oligonucleotides comprises a first oligonucleotide conjugated to the first binding partner, a second oligonucleotide conjugated to the second binding partner, a third oligonucleotide partially hybridized to the scaffold nucleic acid and comprising a 3' overhang, a fourth oligonucleotide partially hybridized to the scaffold nucleic acid and comprising a 5' overhang that is not complementary to the 3' overhang, wherein the 3' and 5' overhangs each comprise at least 7 nucleotides that are fully complementary to the latch nucleic acid, wherein the second binding interaction (a) comprises the latch nucleic acid hybridized to the 3' overhang of the third oligonucleotide and the 5' overhang of the fourth oligonucleotide and (b) occurs as a result of the first binding interaction, and wherein the latch nucleic acid does not directly hybridize to the scaffold nucleic acid.

2. The method of claim 1, wherein the second binding interaction further comprises a covalent bond.

3. The method of claim 1, wherein the second binding interaction is triggered by heating, change in solution conditions, change in concentration or presence of ions or atoms in solution.

4. The method of claim 1, wherein the first binding partner is directly bound to the second binding partner.

5. The method of claim 1, wherein the first binding partner is bound to an analyte bound to the second binding partner.

6. The method of claim 1, wherein the second binding interaction may be disrupted through strand displacement.

7. The method of claim 1, wherein the third oligonucleotide is upstream of the first oligonucleotide and the fourth oligonucleotide is downstream of the second oligonucleotide.

8. The method of claim 1, wherein the third oligonucleotide is proximal to and downstream of the first oligonucleotide and the fourth oligonucleotide is proximal to and upstream of the second oligonucleotide.

9. The method of claim 6, wherein the 3' and 5' overhangs each comprise at least 10 nucleotides that are fully complementary to the latch nucleic acid.

* * * * *

UNITED STATES PATENT AND TRADEMARK OFFICE
CERTIFICATE OF CORRECTION

PATENT NO. : 12,077,807 B2
APPLICATION NO. : 15/738982
DATED : September 3, 2024
INVENTOR(S) : Arun Richard Chandrasekaran et al.

It is certified that error appears in the above-identified patent and that said Letters Patent is hereby corrected as shown below:

In the Claims

At Column 112, Lines 43-45, the text:
"9. The method of claim 6, wherein the 3' and 5' overhangs each comprise at least 10 nucleotides that are fully complementary to the latch nucleic acid."

Should read:
-- 9. The method of claim 1, wherein the 3' and 5' overhangs each comprise at least 10 nucleotides that are fully complementary to the latch nucleic acid. --

Signed and Sealed this
Nineteenth Day of August, 2025

Coke Morgan Stewart
*Acting Director of the United States Patent and Trademark Office*

SEQUENCE LISTING

```
<160> NUMBER OF SEQ ID NOS: 183

<210> SEQ ID NO 1
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 1
agagcataaa gctaaatcgg ttgtaccaaa aacattatga ccctgtaata cttttgcggg      60

<210> SEQ ID NO 2
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 2
agaagccttt atttcaacgc aaggataaaa attttagaa ccctcatata ttttaaatgc       60

<210> SEQ ID NO 3
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 3
aatgcctgag taatgtgtag gtaaagattc aaaagggtga gaaaggccgg agacagtcaa      60

<210> SEQ ID NO 4
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 4
atcaccatca atatgatatt caaccgttct agctgataaa ttaatgccgg agagggtagc      60

<210> SEQ ID NO 5
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 5 tattttgag agatctacaa aggctatcag gtcattgcct gagagtctgg agcaaacaag       60

<210> SEQ ID NO 6
<211> LENGTH: 60
<212> TYPE: DNA
<213> ORGANISM: Artificial Sequence
<220> FEATURE:
<223> OTHER INFORMATION: Synthetic Polynucleotide
```

<400> SEQUENCE: 6
agaatcgatg aacggtaatc gtaaaactag catgtcaatc atatgtaccc cggttgataa    60

<210> SEQ ID NO 7
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 7
tcagaaaagc cccaaaaaca ggaagattgt ataagcaaat atttaaattg taaacgttaa    60

<210> SEQ ID NO 8
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 8
tattttgtta aaattcgcat taaattttg ttaaatcagc tcattttta accaatagga    60

<210> SEQ ID NO 9
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 9
acgccatcaa aaataattcg cgtctggcct tcctgtagcc agctttcatc aacattaaat    60

<210> SEQ ID NO 10
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 10
ggataggtca cgttggtgta gatgggcgca tcgtaaccgt gcatctgcca gtttgagggg    60

<210> SEQ ID NO 11
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 11
acgacgacag tatcggcctc aggaagatcg cactccagcc agctttccgg caccgcttct    60

<210> SEQ ID NO 12
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 12
ggtgccggaa accaggcaaa gcgccattcg ccattcaggc tgcgcaactg ttgggaaggg    60

<210> SEQ ID NO 13

```
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 13
cgatcggtgc gggcctcttc gctattacgc cagctggcga aggggatg tgctgcaagg    60

<210> SEQ ID NO 14
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 14
cgattaagtt gggtaacgcc agggttttcc cagtcacgac gttgtaaaac gacggccagt    60

<210> SEQ ID NO 15
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 15
gccaagcttg catgcctgca ggtcgactct agaggatccc cgggtaccga gctcgaattc    60

<210> SEQ ID NO 16
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 16
gtaatcatgg tcatagctgt ttcctgtgtg aaattgttat ccgctcacaa ttccacacaa    60

<210> SEQ ID NO 17
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 17
catacgagcc ggaagcataa agtgtaaagc ctggggtgcc taatgagtga gctaactcac    60

<210> SEQ ID NO 18
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 18
attaattgcg ttgcgctcac tgcccgcttt ccagtcggga aacctgtcgt gccagctgca    60

<210> SEQ ID NO 19
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 19
```
ttaatgaatc ggccaacgcg cggggagagg cggtttgcgt attgggcgcc agggtggttt    60

<210> SEQ ID NO 20
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 20
gttgcagcaa gcggtccacg ctggtttgcc ccagcaggcg aaaatcctgt ttgatggtgg    60

<210> SEQ ID NO 21
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 21
ttccgaaatc ggcaaaatcc cttataaatc aaaagaatag cccgagatag ggttgagtgt    60

<210> SEQ ID NO 22
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 22
tgttccagtt tggaacaaga gtccactatt aaagaacgtg gactccaacg tcaaagggcg    60

<210> SEQ ID NO 23
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 23
aaaaaccgtc tatcagggcg atggcccact acgtgaacca tcacccaaat caagtttttt    60

<210> SEQ ID NO 24
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 24
ggggtcgagg tgccgtaaag cactaaatcg gaaccctaaa gggagccccc gatttagagc    60

<210> SEQ ID NO 25
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 25
ttgacgggga agccggcga acgtggcgag aaaggaaggg aagaaagcga aaggagcggg    60

<210> SEQ ID NO 26
<211> LENGTH: 60
<212> TYPE: DNA

```
<213> ORGANISM: Artificial Sequence
<220> FEATURE:
<223> OTHER INFORMATION: Synthetic Polynucleotide

<400> SEQUENCE: 26
cgctagggcg ctggcaagtg tagcggtcac gctgcgcgta accaccacac ccgccgcgct    60

<210> SEQ ID NO 27
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 27
taatgcgccg ctacagggcg cgtactatgg ttgctttgac gagcacgtat aacgtgcttt    60

<210> SEQ ID NO 28
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 28
cctcgttaga atcagagcgg gagctaaaca ggaggccgat taagggatt ttagacagga     60

<210> SEQ ID NO 29
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 29
acggtacgcc agaatcctga gaagtgtttt tataatcagt gaggccaccg agtaaaagag    60

<210> SEQ ID NO 30
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 30
ttgcctgagt agaagaactc aaactatcgg ccttgctggt aatatccaga acaatattac    60

<210> SEQ ID NO 31
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 31
cgccagccat tgcaacagga aaacgctca tggaaatacc tacattttga cgctcaatcg     60

<210> SEQ ID NO 32
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 32
tctgaaatgg attatttaca ttggcagatt caccagtcac acgaccagta ataaaaggga    60
```

-continued

```
<210> SEQ ID NO 33
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 33
cattctggcc aacagagata gaacccttct gacctgaaag cgtaagaata cgtggcacag    60

<210> SEQ ID NO 34
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 34
acaatatttt tgaatggcta ttagtcttta atgcgcgaac tgatagccct aaaacatcgc    60

<210> SEQ ID NO 35
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 35
cattaaaaat accgaacgaa ccaccagcag aagataaaac agaggtgagg cggtcagtat    60

<210> SEQ ID NO 36
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 36
taacaccgcc tgcaacagtg ccacgctgag agccagcagc aaatgaaaaa tctaaagcat    60

<210> SEQ ID NO 37
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 37
caccttgctg aacctcaaat atcaaaccct caatcaatat ctggtcagtt ggcaaatcaa    60

<210> SEQ ID NO 38
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 38
cagttgaaag gaattgagga aggttatcta aaatatcttt aggagcacta acaactaata    60

<210> SEQ ID NO 39
<211> LENGTH: 60
<212> TYPE: DNA
<213> ORGANISM: Artificial Sequence
<220> FEATURE:
```

<223> OTHER INFORMATION: Synthetic Polynucleotide

<400> SEQUENCE: 39
gattagagcc gtcaatagat aatacatttg aggatttaga agtattagac tttacaaaca    60

<210> SEQ ID NO 40
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 40
cattatcatt ttgcggaaca aagaaaccac cagaaggagc ggaattatca tcatattcct    60

<210> SEQ ID NO 41
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 41
gattatcaga tgatggcaat tcatcaatat aatcctgatt gtttggatta tacttctgaa    60

<210> SEQ ID NO 42
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 42
taatggaagg gttagaacct accatatcaa aattatttgc acgtaaaaca gaaataaaga    60

<210> SEQ ID NO 43
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 43
aattgcgtag attttcaggt ttaacgtcag atgaatatac agtaacagta cctttacat    60

<210> SEQ ID NO 44
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 44
cgggagaaac aataacggat tcgcctgatt gctttgaata ccaagttaca aaatcgcgca    60

<210> SEQ ID NO 45
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 45
gaggcgaatt attcatttca attacctgag caaaagaaga tgatgaaaca aacatcaaga    60

```
<210> SEQ ID NO 46
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 46
aaacaaaatt aattacattt aacaatttca tttgaattac cttttttaat ggaaacagta    60

<210> SEQ ID NO 47
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 47
cataaatcaa tatatgtgag tgaataacct tgcttctgta aatcgtcgct attaattaat    60

<210> SEQ ID NO 48
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 48
tttcccttag aatccttgaa aacatagcga tagcttagat taagacgctg agaagagtca    60

<210> SEQ ID NO 49
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 49
atagtgaatt tatcaaaatc ataggtctga gagactacct ttttaacctc cggcttaggt    60

<210> SEQ ID NO 50
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 50
gaaaactttt tcaaatatat tttagttaat ttcatcttct gacctaaatt taatggtttg    60

<210> SEQ ID NO 51
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 51
aaataccgac cgtgtgataa ataaggcgtt aaataagaat aaacaccgga atcataatta    60

<210> SEQ ID NO 52
<211> LENGTH: 60
<212> TYPE: DNA
<213> ORGANISM: Artificial Sequence
<220> FEATURE:
<223> OTHER INFORMATION: Synthetic Polynucleotide
```

<400> SEQUENCE: 52
ctagaaaaag cctgtttagt atcatatgcg ttatacaaat tcttaccagt ataaagccaa    60

<210> SEQ ID NO 53
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 53
cgctcaacag tagggcttaa ttgagaatcg ccatatttaa caacgccaac atgtaattta    60

<210> SEQ ID NO 54
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 54
ggcagaggca ttttcgagcc agtaataaga gaatataaag taccgacaaa aggtaaagta    60

<210> SEQ ID NO 55
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 55
attctgtcca gacgacgaca ataaacaaca tgttcagcta atgcagaacg cgcctgttta    60

<210> SEQ ID NO 56
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 56
tcaacaatag ataagtcctg aacaagaaaa ataatatccc atcctaattt acgagcatgt    60

<210> SEQ ID NO 57
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 57
agaaaccaat caataatcgg ctgtctttcc ttatcattcc aagaacgggt attaaaccaa    60

<210> SEQ ID NO 58
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 58
gtaccgcact catcgagaac aagcaagccg tttttatttt catcgtagga atcattaccg    60

<210> SEQ ID NO 59
<211> LENGTH: 60

```
<212> TYPE: DNA
<213> ORGANISM: Artificial Sequence
<220> FEATURE:
<223> OTHER INFORMATION: Synthetic Polynucleotide

<400> SEQUENCE: 59
cgcccaatag caagcaaatc agatatagaa ggcttatccg gtattctaag aacgcgaggc    60

<210> SEQ ID NO 60
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 60
attttgcacc cagctacaat tttatcctga atcttaccaa cgctaacgag cgtctttcca    60

<210> SEQ ID NO 61
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 61
gagcctaatt tgccagttac aaaataaaca gccatattat ttatcccaat ccaaataaga    60

<210> SEQ ID NO 62
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 62
aacgattttt tgtttaacgt caaaaatgaa aatagcagcc tttacagaga gaataacata    60

<210> SEQ ID NO 63
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 63
aaaacaggga agcgcattag acgggagaat taactgaaca ccctgaacaa agtcagaggg    60

<210> SEQ ID NO 64
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 64
taattgagcg ctaatatcag agagataacc cacaagaatt gagttaagcc caataataag    60

<210> SEQ ID NO 65
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 65
```
agcaagaaac aatgaaatag caatagctat cttaccgaag ccctttttaa gaaaagtaag    60

<210> SEQ ID NO 66
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 66
cagatagccg aacaaagtta ccagaaggaa accgaggaaa cgcaataata acggaatacc    60

<210> SEQ ID NO 67
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 67
caaaagaact ggcatgatta agactcctta ttacgcagta tgttagcaaa cgtagaaaat    60

<210> SEQ ID NO 68
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 68
acatacataa aggtggcaac atataaaaga aacgcaaaga caccacggaa taagtttatt    60

<210> SEQ ID NO 69
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 69
ttgtcacaat caatagaaaa ttcatatggt ttaccagcgc caaagacaaa agggcgacat    60

<210> SEQ ID NO 70
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 70
tcaccgtcac cgacttgagc catttgggaa ttagagccag caaaatcacc agtagcacca    60

<210> SEQ ID NO 71
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 71
ttaccattag caaggccgga aacgtcacca atgaaaccat cgatagcagc accgtaatca    60

<210> SEQ ID NO 72
<211> LENGTH: 60
<212> TYPE: DNA
<213> ORGANISM: Artificial Sequence

```
<220> FEATURE:
<223> OTHER INFORMATION: Synthetic Polynucleotide

<400> SEQUENCE: 72
gtagcgacag aatcaagttt gcctttagcg tcagactgta gcgcgttttc atcggcattt    60

<210> SEQ ID NO 73
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 73
tcggtcatag ccccttatt agcgtttgcc atcttttcat aatcaaaatc accggaacca    60

<210> SEQ ID NO 74
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 74
gagccaccac cggaaccgcc tccctcagag ccgccaccct cagaaccgcc accctcagag    60

<210> SEQ ID NO 75
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 75
ccaccaccct cagagccgcc accagaacca ccaccagagc cgccgccagc attgacagga    60

<210> SEQ ID NO 76
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 76
ggttgaggca ggtcagacga ttggccttga tattcacaaa caaataaatc ctcattaaag    60

<210> SEQ ID NO 77
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 77
ccagaatgga aagcgcagtc tctgaattta ccgttccagt aagcgtcata catggctttt    60

<210> SEQ ID NO 78
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 78
gatgatacag gagtgtactg gtaataagtt ttaacggggt cagtgccttg agtaacagtg    60
```

<210> SEQ ID NO 79
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 79
cccgtataaa cagttaatgc cccctgccta tttcggaacc tattattctg aaacatgaaa    60

<210> SEQ ID NO 80
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 80
ccaggcggat aagtgccgtc gagagggttg atataagtat agcccggaat aggtgtatca    60

<210> SEQ ID NO 81
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 81
ccgtactcag gaggtttagt accgccaccc tcagaaccgc caccctcaga accgccaccc    60

<210> SEQ ID NO 82
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 82
tcagagccac caccctcatt ttcagggata gcaagcccaa taggaaccca tgtaccgtaa    60

<210> SEQ ID NO 83
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 83
cactgagttt cgtcaccagt acaaactaca acgcctgtag cattccacag acagccctca    60

<210> SEQ ID NO 84
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 84
tagttagcgt aacgatctaa agttttgtcg tctttccaga cgttagtaaa tgaattttct    60

<210> SEQ ID NO 85
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 85
gtatgggatt tgctaaaca actttcaaca gtttcagcgg agtgagaata gaaaggaaca    60

<210> SEQ ID NO 86
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 86
actaaaggaa ttgcgaataa taatttttc acgttgaaaa tctccaaaaa aaaggctcca    60

<210> SEQ ID NO 87
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 87
aaaggagcct ttaattgtat cggtttatca gcttgctttc gaggtgaatt tcttaaacag    60

<210> SEQ ID NO 88
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 88
cttgataccg atagttgcgc cgacaatgac aacaaccatc gcccacgcat aaccgatata    60

<210> SEQ ID NO 89
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 89
ttcggtcgct gaggcttgca gggagttaaa ggccgctttt gcgggatcgt caccctcagc    60

<210> SEQ ID NO 90
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 90 cttttttcatg aggaagtttc cattaaacgg gtaaaatacg taatgccact acgaaggcac    60

<210> SEQ ID NO 91
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 91
caacctaaaa cgaaagaggc aaaagaatac actaaaacac tcatctttga cccccagcga    60

<210> SEQ ID NO 92

<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 92
ttataccaag cgcgaaacaa agtacaacgg agatttgtat catcgcctga taaattgtgt    60

<210> SEQ ID NO 93
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 93
cgaaatccgc gacctgctcc atgttactta gccggaacga ggcgcagacg gtcaatcata    60

<210> SEQ ID NO 94
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 94
agggaaccga actgaccaac tttgaaagag gacagatgaa cggtgtacag accaggcgca    60

<210> SEQ ID NO 95
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 95
taggctggct gaccttcatc aagagtaatc ttgacaagaa ccggatattc attacccaaa    60

<210> SEQ ID NO 96
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 96
tcaacgtaac aaagctgctc attcagtgaa taaggcttgc cctgacgaga aacaccagaa    60

<210> SEQ ID NO 97
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 97
cgagtagtaa attgggcttg agatggttta atttcaactt taatcattgt gaattacctt    60

<210> SEQ ID NO 98
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 98

```
atgcgatttt aagaactggc tcattatacc agtcaggacg ttgggaagaa aaatctacgt    60
```

<210> SEQ ID NO 99
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 99

```
taataaaacg aactaacgga acaacattat tacaggtaga aagattcatc agttgagatt    60
```

<210> SEQ ID NO 100
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 100

```
taagagcaac actatcataa ccctcgttta ccagacgacg ataaaaacca aaatagcgag    60
```

<210> SEQ ID NO 101
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 101

```
aggcttttgc aaaagaagtt ttgccagagg gggtaatagt aaaatgttta gactggatag    60
```

<210> SEQ ID NO 102
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 102

```
cgtccaatac tgcggaatcg tcataaatat tcattgaatc cccctcaaat gctttaaaca    60
```

<210> SEQ ID NO 103
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 103

```
gttcagaaaa cgagaatgac cataaatcaa aaatcaggtc tttaccctga ctattatagt    60
```

<210> SEQ ID NO 104
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 104

```
cagaagcaaa gcggattgca tcaaaaagat taagaggaag cccgaaagac ttcaaatatc    60
```

<210> SEQ ID NO 105
<211> LENGTH: 60
<212> TYPE: DNA

```
<213> ORGANISM: Artificial Sequence
<220> FEATURE:
<223> OTHER INFORMATION: Synthetic Polynucleotide

<400> SEQUENCE: 105
gcgttttaat tcgagcttca aagcgaacca gaccggaagc aaactccaac aggtcaggat    60

<210> SEQ ID NO 106
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 106
tagagagtac ctttaattgc tcctttgat aagaggtcat ttttgcggat ggcttagagc    60

<210> SEQ ID NO 107
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 107
ttaattgctg aatataatgc tgtagctcaa catgttttaa atatgcaact aaagtacggt    60

<210> SEQ ID NO 108
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 108
gtctggaagt ttcattccat ataacagttg attcccaatt ctgcgaacga gtagatttag    60

<210> SEQ ID NO 109
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 109
tttgaccatt agatacattt cgcaaatggt caataacctg tttagctat                49

<210> SEQ ID NO 110
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 110
aacatccaat aaatcataca ggcaaggcaa agaattagca aaattaagca ataaagcctc    60

<210> SEQ ID NO 111
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 111
gtgagcgagt aacaacccgt cggattctcc gtgggaacaa acggcggatt gaccgtaatg    60
```

<210> SEQ ID NO 112
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 112
ttcttttcac cagtgagacg ggcaacagct gattgccctt caccgcctgg ccctgagaga    60

<210> SEQ ID NO 113
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 113
tctgtccatc acgcaaatta accgttgtag caatacttct tgattagta ataacatcac     60

<210> SEQ ID NO 114
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 114
attcgacaac tcgtattaaa tcctttgccc gaacgttatt aattttaaaa gtttgagtaa    60

<210> SEQ ID NO 115
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 115
tgggttatat aactatatgt aaatgctgat gcaaatccaa tcgcaagaca aagaacgcga    60

<210> SEQ ID NO 116
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 116
gttttagcga acctcccgac ttgcgggagg ttttgaagcc ttaaatcaag attagttgct    60

<210> SEQ ID NO 117
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 117
tcaaccgatt gagggaggga aggtaaatat tgacggaaat tattcattaa aggtgaatta    60

<210> SEQ ID NO 118
<211> LENGTH: 60
<212> TYPE: DNA
<213> ORGANISM: Artificial Sequence
<220> FEATURE:

<223> OTHER INFORMATION: Synthetic Polynucleotide

<400> SEQUENCE: 118
gtattaagag gctgagactc ctcaagagaa ggattaggat tagcggggtt ttgctcagta    60

<210> SEQ ID NO 119
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 119
agcgaaagac agcatcggaa cgagggtagc aacggctaca gaggctttga ggactaaaga    60

<210> SEQ ID NO 120
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 120
taggaatacc acattcaact aatgcagata cataacgcca aaaggaatta cgaggcatag    60

<210> SEQ ID NO 121
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 121
attttcattt ggggcgcgag ctgaaaaggt ggcatcaatt ctactaatag tagtagcatt    60

<210> SEQ ID NO 122
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 122
accgttgtag caatacttct ttgattagta ataacatcac ttcagattga agggc    55

<210> SEQ ID NO 123
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 123
catgagaccg tgtcctcaac cgattgaggg agggaaggta aatattgacg gaaat    55

<210> SEQ ID NO 124
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 124
tctgtccatc acgcaaatta    20

```
<210> SEQ ID NO 125
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 125
tattcattaa aggtgaatta                                              20

<210> SEQ ID NO 126
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 126
ggacacggtc tcatggccct tcaatctgaa                                   30

<210> SEQ ID NO 127
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 127
gacacggtct catggccctt caatctga                                     28

<210> SEQ ID NO 128
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 128
acacggtctc atggcccttc aatctg                                       26

<210> SEQ ID NO 129
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 129
cacggtctca tggcccttca atct                                         24

<210> SEQ ID NO 130
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 130
acggtctcat ggcccttcaa tc                                           22

<210> SEQ ID NO 131
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 131
cggtctcatg gcccttcaat                                                     20

<210> SEQ ID NO 132
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 132
ggacacggtc tcatggccct tcaatctgaa                                          30

<210> SEQ ID NO 133
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 133
ggacacggtc tcatggccct tcaatctga                                           29

<210> SEQ ID NO 134
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 134
ggacacggtc tcatggccct tcaatctg                                            28

<210> SEQ ID NO 135
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 135
ggacacggtc tcatggccct tcaatct                                             27

<210> SEQ ID NO 136
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 136
ggacacggtc tcatggccct tcaatc                                              26

<210> SEQ ID NO 137
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 137
ggacacggtc tcatggccct tcaat                                               25

<210> SEQ ID NO 138
<211> LENGTH: 24
```

```
<212> TYPE: DNA
<213> ORGANISM: Artificial Sequence
<220> FEATURE:
<223> OTHER INFORMATION: Synthetic Polynucleotide

<400> SEQUENCE: 138
ggacacggtc tcatggccct tcaa                                          24

<210> SEQ ID NO 139
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 139
ggacacggtc tcatggccct tca                                           23

<210> SEQ ID NO 140
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 140
ggacacggtc tcatggccct tc                                            22

<210> SEQ ID NO 141
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 141
ggacacggtc tcatggccct t                                             21

<210> SEQ ID NO 142
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 142
ggacacggtc tcatggccct                                               20

<210> SEQ ID NO 143
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 143
accgttgtag caatacttct ttgattagta ataacatcac ttcagattga agggc        55

<210> SEQ ID NO 144
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 144
```
catgagaccg tgtcctcaac cgattgaggg agggaaggta aatattgacg gaaat    55

<210> SEQ ID NO 145
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 145
tctgtccatc acgcaaatta    20

<210> SEQ ID NO 146
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 146
tattcattaa aggtgaatta    20

<210> SEQ ID NO 147
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 147
acggtctcat ggcccttcaa tc    22

<210> SEQ ID NO 148
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 148
accgttgtag caatacttct ttgattagta ataacatcac cacaaattcg g    51

<210> SEQ ID NO 149
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 149
ttctacaggg tatcaaccga ttgagggagg gaaggtaaat attgacggaa at    52

<210> SEQ ID NO 150
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 150
tctgtccatc acgcaaatta    20

<210> SEQ ID NO 151
<211> LENGTH: 20
<212> TYPE: DNA
<213> ORGANISM: Artificial Sequence

```
<220> FEATURE:
<223> OTHER INFORMATION: Synthetic Polynucleotide

<400> SEQUENCE: 151
tattcattaa aggtgaatta                                          20

<210> SEQ ID NO 152
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 152
taccctgtag aaccgaattt gtg                                      23

<210> SEQ ID NO 153
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 153
ttcagattga agggc                                               15

<210> SEQ ID NO 154
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 154
catgagaccg tgtcc                                               15

<210> SEQ ID NO 155
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 155
atttccgtca atatttacct tccctccctc aatcggttga                    40

<210> SEQ ID NO 156
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 156
gtgatgttat tactaatcaa agaagtattg ctacaacggt                    40

<210> SEQ ID NO 157
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 157
accgttgtag caatacttct ttgattagta ataacatcac ttcagattga agggc   55
```

```
<210> SEQ ID NO 158
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 158
catgagaccg tgtcctcaac cgattgaggg agggaaggta aatattgacg gaaat         55

<210> SEQ ID NO 159
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 159
caatacttct tgattagta ataacatcac ttcagattga agggc               45

<210> SEQ ID NO 160
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 160
catgagaccg tgtcctcaac cgattgaggg agggaaggta aatat              45

<210> SEQ ID NO 161
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(7)
<223> OTHER INFORMATION: Modified with isoacyl

<400> SEQUENCE: 161

Leu Pro Glu Thr Gly Gly Ser
1               5

<210> SEQ ID NO 162
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 162

Leu Pro Glu Thr Gly Gly Ser
1               5

<210> SEQ ID NO 163
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 163
gcctcgtctc gcctcgtctc                                           20
```

```
<210> SEQ ID NO 164
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 164
tttcatttcg tctatccgaa aagcggatag acg                            33

<210> SEQ ID NO 165
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 165
caatacttct tgattagta ataacatcac tttcatttcg tctatccgaa aagcggatag    60
acg                                                            63

<210> SEQ ID NO 166
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 166
cgtctatccg cttttgcatc acgtcaaatg aaa                            33

<210> SEQ ID NO 167
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 167
cgtctatccg cttttgcatc acgtcaaatg aaatcaaccg attgagggag ggaaggtaaa    60
tat                                                            63

<210> SEQ ID NO 168
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 168
tttcatttga cgtgatgcaa aagcggatag acggatcgat c                   41

<210> SEQ ID NO 169
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 169
gatcgatccg tctatccgct tttgcatcac gtcaaatgaa a                   41

<210> SEQ ID NO 170
<211> LENGTH: 31
<212> TYPE: DNA
```

```
<213> ORGANISM: Artificial Sequence
<220> FEATURE:
<223> OTHER INFORMATION: Synthetic Polynucleotide

<400> SEQUENCE: 170
gtcgttcgct tctctatgtg tcttccggcc c                            31

<210> SEQ ID NO 171
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 171
tcagttggca aatcaacagt tgaaaggaat tagggccgga agacaca          47

<210> SEQ ID NO 172
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 172
agagaagcga acgacatggg ttatataact atatgtaaat gctga            45

<210> SEQ ID NO 173
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (29)..(29)
<223> OTHER INFORMATION: Modified with
      \iAmMC6T\\iSp9\\iAmMC6T\TTTT\3AmMC6T\

<400> SEQUENCE: 173
tcagttggca aatcaacagt tgaaaggaa                              29

<210> SEQ ID NO 174
<211> LENGTH: 28
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with
      \5AmMC6\\iAmMC6T\TTTT\iAmMC6T\\iSp9\\iAmMC6T\

<400> SEQUENCE: 174
gggttatata actatatgta aatgctga                                28

<210> SEQ ID NO 175
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 175
ugagguagua gguuguauag uu                                      22
```

```
<210> SEQ ID NO 176
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 176
ugagguagua gguugugugg uu                                              22

<210> SEQ ID NO 177
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 177
ugagguagua gguuguaugg uu                                              22

<210> SEQ ID NO 178
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 178
agagguagua gguugcauag uu                                              22

<210> SEQ ID NO 179
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 179
ugagguagga gguuguauag uu                                              22

<210> SEQ ID NO 180
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 180
ugagguagua gauuguauag uu                                              22

<210> SEQ ID NO 181
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 181
ugagguagua guuuguacag uu                                              22

<210> SEQ ID NO 182
<211> LENGTH: 22
<212> TYPE: RNA
<213> ORGANISM: Artificial Sequence
<220> FEATURE:
<223> OTHER INFORMATION: Synthetic Polynucleotide
```

```
<400> SEQUENCE: 182
ugagguagua guuugugcug uu                                        22

<210> SEQ ID NO 183
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 183
ugagguaguu guuuguacag uu                                        22
```